United States Patent
Wilcox et al.

(10) Patent No.: US 11,672,553 B2
(45) Date of Patent: Jun. 13, 2023

(54) METHOD AND APPARATUS FOR TREATMENT OF INTRACRANIAL HEMORRHAGES

(71) Applicant: EKOS CORPORATION, Bothell, WA (US)

(72) Inventors: Robert L. Wilcox, Bothell, WA (US); Ronald L. Haas, Kirkland, WA (US)

(73) Assignee: EKOS Corporation, Bothell, WA (US)

(*) Notice: Subject to any disclaimer, the term of this patent is extended or adjusted under 35 U.S.C. 154(b) by 541 days.

(21) Appl. No.: 16/803,971

(22) Filed: Feb. 27, 2020

(65) Prior Publication Data
US 2020/0197659 A1  Jun. 25, 2020

Related U.S. Application Data

(63) Continuation of application No. 13/726,105, filed on Dec. 22, 2012, now abandoned, which is a
(Continued)

(51) Int. Cl.
*A61B 17/22* (2006.01)
*A61M 25/00* (2006.01)
(Continued)

(52) U.S. Cl.
CPC ......... *A61B 17/2202* (2013.01); *A61M 25/00* (2013.01); *A61M 25/003* (2013.01);
(Continued)

(58) Field of Classification Search
CPC ............... A61B 17/2202; A61B 18/24; A61B 2017/00084; A61B 2017/00561;
(Continued)

(56) References Cited

U.S. PATENT DOCUMENTS 2,961,382 A   11/1960 Singher et al.
3,352,303 A   11/1967 Delaney
(Continued)

FOREIGN PATENT DOCUMENTS

AU   634470 B2   2/1993
CA   1083040 A   8/1980
(Continued)

OTHER PUBLICATIONS

"Photophoresis Apparatus in Treatment of a Cutis T Cell Lymphadenoma," Science (Japan Edition), Oct. 1988, pp. 65-73.
(Continued)

*Primary Examiner* — Brandy S Lee
(74) *Attorney, Agent, or Firm* — Seager, Tufte & Wickhem, LLP

(57) ABSTRACT

An ultrasound catheter with fluid delivery lumens, fluid evacuation lumens and a light source is used for the treatment of intracerebral hemorrhages. After the catheter is inserted into a blood clot in the brain, a lytic drug can be delivered to the blood clot via the fluid delivery lumens while applying ultrasonic energy to the treatment site. As the blood clot is dissolved, the liquefied blood clot can be removed by evacuation through the fluid evacuation lumens.

19 Claims, 17 Drawing Sheets

Related U.S. Application Data continuation of application No. 12/143,470, filed on Jun. 20, 2008, now Pat. No. 9,044,568.

(60) Provisional application No. 61/032,741, filed on Feb. 29, 2008, provisional application No. 60/945,846, filed on Jun. 22, 2007.

(51) Int. Cl.

| | |
|---|---|
| A61B 18/24 | (2006.01) |
| A61B 17/00 | (2006.01) |
| A61B 17/12 | (2006.01) |
| A61B 90/30 | (2016.01) |
| A61B 90/00 | (2016.01) |
| A61M 1/00 | (2006.01) |

(52) U.S. Cl.
CPC ..... *A61B 18/24* (2013.01); *A61B 2017/00084* (2013.01); *A61B 2017/00561* (2013.01); *A61B 2017/12004* (2013.01); *A61B 2090/064* (2016.02); *A61B 2090/306* (2016.02); *A61B 2090/309* (2016.02); *A61B 2217/005* (2013.01); *A61B 2217/007* (2013.01); *A61M 1/85* (2021.05); *A61M 25/007* (2013.01); *A61M 25/0032* (2013.01); *A61M 2025/0002* (2013.01); *A61M 2205/058* (2013.01)

(58) Field of Classification Search
CPC .... A61B 2017/12004; A61B 2090/064; A61B 2090/306; A61B 2090/309; A61B 2217/005; A61B 2217/007; A61M 1/85; A61M 2025/0002; A61M 2205/058; A61M 25/00; A61M 25/0032; A61M 25/007; A61M 25/003
See application file for complete search history.

(56) References Cited

U.S. PATENT DOCUMENTS

| | | | |
|---|---|---|---|
| 3,430,625 A | 3/1969 | McLeod, Jr. |
| 3,433,226 A | 3/1969 | Boyd |
| 3,437,851 A | 4/1969 | Cady |
| 3,443,226 A | 5/1969 | Knight |
| 3,565,062 A | 2/1971 | Kuris |
| 3,635,213 A | 1/1972 | Lahay |
| 3,794,910 A | 2/1974 | Ninke et al. |
| 3,827,115 A | 8/1974 | Bom |
| 3,861,391 A | 1/1975 | Antonevich et al. |
| 3,902,083 A | 8/1975 | Zoltan |
| D238,905 S | 2/1976 | Sokol et al. |
| 3,938,502 A | 2/1976 | Bom |
| 3,941,122 A | 3/1976 | Jones |
| 3,976,987 A | 8/1976 | Anger |
| 4,006,743 A | 2/1977 | Kowarski |
| 4,027,659 A | 6/1977 | Slingluff |
| 4,040,414 A | 8/1977 | Suroff |
| D247,251 S | 2/1978 | Napoli |
| 4,192,294 A | 3/1980 | Vasilevsky et al. |
| 4,265,251 A | 5/1981 | Tickner |
| 4,309,989 A | 1/1982 | Fahim |
| 4,312,361 A | 1/1982 | Nicholson et al. |
| 4,319,580 A | 3/1982 | Colley et al. |
| D264,128 S | 4/1982 | Barnes et al. |
| 4,354,502 A | 10/1982 | Colley et al. |
| 4,381,004 A | 4/1983 | Babb |
| 4,457,748 A | 7/1984 | Lallin et al. |
| 4,466,442 A | 8/1984 | Hilmann et al. |
| 4,512,762 A | 4/1985 | Spears |
| 4,531,943 A | 7/1985 | Van Tassel et al. |
| 4,549,533 A | 10/1985 | Cain et al. |
| 4,557,723 A | 12/1985 | Sibalis |
| 4,573,470 A | 3/1986 | Samson et al. |
| 4,582,067 A | 4/1986 | Silverstein et al. |
| 4,587,975 A | 5/1986 | Salo et al. |
| 4,605,399 A | 8/1986 | Weston et al. |
| 4,639,735 A | 1/1987 | Yamamoto et al. |
| 4,640,689 A | 2/1987 | Slibalis |
| 4,646,754 A | 3/1987 | Seale |
| 4,657,543 A | 4/1987 | Langer et al. |
| 4,657,756 A | 4/1987 | Rasor et al. |
| 4,682,596 A | 7/1987 | Bales et al. |
| 4,692,139 A | 9/1987 | Stiles |
| 4,697,595 A | 10/1987 | Breyer et al. |
| 4,698,058 A | 10/1987 | Greenfeld et al. |
| 4,699,150 A | 10/1987 | Kawabuchi et al. |
| 4,702,732 A | 10/1987 | Powers et al. |
| 4,708,716 A | 11/1987 | Sibalis |
| 4,709,698 A | 12/1987 | Johnston et al. |
| 4,710,192 A | 12/1987 | Liotta et al. |
| 4,717,379 A | 1/1988 | Ekholmer |
| 4,729,384 A | 3/1988 | Bazenet |
| 4,739,768 A | 4/1988 | Engelson |
| D296,240 S | 6/1988 | Albright et al. |
| 4,750,902 A | 6/1988 | Wuchinich et al. |
| 4,754,752 A | 7/1988 | Ginsburg et al. |
| 4,762,915 A | 8/1988 | Kung et al. |
| 4,767,402 A | 8/1988 | Kost et al. |
| 4,769,017 A | 9/1988 | Fath et al. |
| 4,770,185 A | 9/1988 | Silverstein et al. |
| 4,772,594 A | 9/1988 | Hashimoto et al. |
| 4,774,958 A | 10/1988 | Feinstein |
| 4,780,212 A | 10/1988 | Kost et al. |
| 4,781,677 A | 11/1988 | Wilcox |
| 4,787,883 A | 11/1988 | Kroyer |
| 4,795,439 A | 1/1989 | Guest |
| 4,797,285 A | 1/1989 | Barenholz et al. |
| 4,808,153 A | 2/1989 | Parisi |
| 4,820,260 A | 4/1989 | Hayden |
| 4,821,740 A | 4/1989 | Tachibana et al. |
| 4,841,977 A | 6/1989 | Griffith et al. |
| 4,844,882 A | 7/1989 | Widder et al. |
| 4,855,064 A | 8/1989 | Schlein |
| 4,870,953 A | 10/1989 | Michael et al. |
| 4,877,031 A | 10/1989 | Conway et al. |
| 4,883,457 A | 11/1989 | Sibalis |
| 4,900,540 A | 2/1990 | Ryan et al. |
| 4,917,088 A | 4/1990 | Crittenden |
| 4,917,102 A | 4/1990 | Miller et al. |
| 4,920,954 A | 5/1990 | Mliger et al. |
| 4,921,478 A | 5/1990 | Solano et al. |
| 4,924,863 A | 5/1990 | Sterzer |
| 4,933,843 A | 6/1990 | Scheller et al. |
| 4,936,281 A | 6/1990 | Stasz |
| 4,947,852 A | 8/1990 | Nassi et al. |
| 4,948,587 A | 8/1990 | Kost et al. |
| 4,951,677 A | 8/1990 | Crowley et al. |
| 4,953,565 A | 9/1990 | Tachibana et al. |
| 4,955,863 A | 9/1990 | Walker et al. |
| 4,960,109 A | 10/1990 | Lele |
| 4,969,470 A | 11/1990 | Mohl et al. |
| 4,971,991 A | 11/1990 | Umemura et al. |
| 4,992,257 A | 2/1991 | Bonnett et al. |
| 4,995,865 A | 2/1991 | Gahara et al. |
| 5,007,438 A | 4/1991 | Tachibana et al. |
| 5,007,898 A | 4/1991 | Rosenbluth et al. |
| 5,021,044 A | 6/1991 | Sharkawy |
| 5,026,387 A | 6/1991 | Thomas |
| 5,040,537 A | 8/1991 | Katakura |
| 5,053,008 A | 10/1991 | Bajaj |
| 5,053,044 A | 10/1991 | Mueller et al. |
| 5,058,570 A | 10/1991 | Idemoto et al. |
| 5,059,851 A | 10/1991 | Corl et al. |
| 5,069,664 A | 12/1991 | Guess et al. |
| 5,076,276 A | 12/1991 | Sakurai et al. |
| 5,081,993 A | 1/1992 | Kitney et al. |
| 5,085,662 A | 2/1992 | Willard |
| 5,088,499 A | 2/1992 | Unger |
| 5,095,910 A | 3/1992 | Powers |
| 5,108,369 A | 4/1992 | Ganguly et al. |
| 5,115,805 A | 5/1992 | Bommannan et al. |
| 5,117,831 A | 6/1992 | Jang et al. |
| 5,121,749 A | 6/1992 | Nassi et al. |

(56) References Cited

U.S. PATENT DOCUMENTS

| | | |
|---|---|---|
| 5,125,410 A | 6/1992 | Misono et al. |
| 5,129,883 A | 7/1992 | Black |
| 5,149,319 A | 9/1992 | Unger |
| 5,150,705 A | 9/1992 | Stinson |
| D330,424 S | 10/1992 | Davis et al. |
| 5,156,050 A | 10/1992 | Schmid |
| 5,158,071 A | 10/1992 | Umemura et al. |
| 5,163,421 A | 11/1992 | Bernstein et al. |
| 5,163,436 A | 11/1992 | Saitoh et al. |
| 5,178,620 A | 1/1993 | Eggers et al. |
| 5,181,920 A | 1/1993 | Mueller et al. |
| 5,185,071 A | 2/1993 | Serwer et al. |
| 5,190,766 A | 3/1993 | Ishihara |
| 5,195,520 A | 3/1993 | Schlief et al. |
| 5,197,946 A | 3/1993 | Tachibana |
| 5,203,337 A | 4/1993 | Feldman |
| 5,207,214 A | 5/1993 | Romano |
| 5,209,720 A | 5/1993 | Unger |
| 5,215,680 A | 6/1993 | D'arrigo |
| 5,216,130 A | 6/1993 | Line et al. |
| 5,226,421 A | 7/1993 | Frisbie et al. |
| 5,250,034 A | 10/1993 | Appling et al. |
| 5,261,291 A | 11/1993 | Schoch et al. |
| 5,267,954 A | 12/1993 | Nita |
| 5,267,985 A | 12/1993 | Shimada et al. |
| 5,269,291 A | 12/1993 | Carter |
| 5,269,297 A | 12/1993 | Weng et al. |
| 5,271,406 A | 12/1993 | Ganguly et al. |
| 5,277,913 A | 1/1994 | Thompson et al. |
| 5,279,543 A | 1/1994 | Glikfeld et al. |
| 5,279,546 A | 1/1994 | Mische et al. |
| 5,282,785 A | 2/1994 | Shapland et al. |
| 5,286,254 A | 2/1994 | Shapland et al. |
| 5,289,831 A | 3/1994 | Bosley |
| 5,291,887 A | 3/1994 | Stanley et al. |
| 5,295,484 A | 3/1994 | Marcus et al. |
| 5,295,958 A | 3/1994 | Shturman |
| 5,304,115 A | 4/1994 | Pflueger et al. |
| 5,307,816 A | 5/1994 | Hashimoto et al. |
| 5,312,328 A | 5/1994 | Nita et al. |
| 5,313,949 A | 5/1994 | Yock |
| 5,315,998 A | 5/1994 | Tachibana et al. |
| 5,318,014 A | 6/1994 | Carter |
| 5,323,769 A | 6/1994 | Bommannan et al. |
| 5,324,225 A | 6/1994 | Satoh et al. |
| 5,324,255 A | 6/1994 | Passafaro et al. |
| 5,326,342 A | 7/1994 | Pflueger et al. |
| 5,327,891 A | 7/1994 | Rammler |
| 5,328,470 A | 7/1994 | Nabel et al. |
| 5,342,292 A | 8/1994 | Nita et al. |
| 5,342,608 A | 8/1994 | Moriya et al. |
| 5,344,395 A | 9/1994 | Whalen et al. |
| 5,344,435 A | 9/1994 | Turner et al. |
| 5,345,940 A | 9/1994 | Seward et al. |
| 5,348,481 A | 9/1994 | Ortiz |
| 5,351,693 A | 10/1994 | Taimisto et al. |
| 5,353,798 A | 10/1994 | Sieben |
| 5,354,279 A | 10/1994 | Hoefung |
| 5,362,309 A | 11/1994 | Carter |
| 5,363,853 A | 11/1994 | Lieber et al. |
| 5,364,344 A | 11/1994 | Beattie et al. |
| 5,368,036 A | 11/1994 | Tanaka et al. |
| 5,368,557 A | 11/1994 | Nita et al. |
| 5,368,558 A | 11/1994 | Nita |
| 5,370,675 A | 12/1994 | Edwards et al. |
| 5,372,138 A | 12/1994 | Crowley et al. |
| 5,378,230 A | 1/1995 | Mahurkar |
| 5,380,273 A | 1/1995 | Dubrul et al. |
| 5,385,148 A | 1/1995 | Lesh et al. |
| 5,390,678 A | 2/1995 | Gesswein et al. |
| 5,397,293 A | 3/1995 | Alliger et al. |
| 5,397,301 A | 3/1995 | Pflueger et al. |
| 5,399,158 A | 3/1995 | Lauer et al. |
| 5,401,237 A | 3/1995 | Tachibana et al. |
| 5,403,323 A | 4/1995 | Smith |
| 5,405,322 A | 4/1995 | Lennox et al. |
| 5,409,458 A | 4/1995 | Khairkhahan et al. |
| 5,415,636 A | 5/1995 | Forman |
| 5,419,763 A | 5/1995 | Hildabrand |
| 5,421,338 A | 6/1995 | Crowley et al. |
| 5,423,797 A | 6/1995 | Adrian et al. |
| 5,431,663 A | 7/1995 | Carter |
| 5,440,914 A | 8/1995 | Tachibana et al. |
| 5,445,155 A | 8/1995 | Sieben |
| 5,447,509 A | 9/1995 | Mills et al. |
| 5,447,510 A | 9/1995 | Jensen |
| 5,453,575 A | 9/1995 | O'donnell et al. |
| 5,454,782 A | 10/1995 | Perkins |
| 5,454,795 A | 10/1995 | Samson |
| 5,456,259 A | 10/1995 | Barlow et al. |
| 5,456,726 A | 10/1995 | Kawabata et al. |
| 5,458,568 A | 10/1995 | Racchini et al. |
| 5,461,708 A | 10/1995 | Kahn |
| 5,462,523 A | 10/1995 | Samson et al. |
| 5,465,726 A | 11/1995 | Dickinson et al. |
| 5,474,530 A | 12/1995 | Passafaro et al. |
| 5,474,531 A | 12/1995 | Carter |
| 5,489,279 A | 2/1996 | Meserol |
| 5,496,294 A | 3/1996 | Hergenrother et al. |
| 5,498,236 A | 3/1996 | Dubrul et al. |
| 5,498,238 A | 3/1996 | Shapland et al. |
| 5,509,896 A | 4/1996 | Carter |
| 5,514,092 A | 5/1996 | Forman et al. |
| 5,520,189 A | 5/1996 | Malinowski et al. |
| 5,523,058 A | 6/1996 | Umemura et al. |
| 5,524,624 A | 6/1996 | Tepper et al. |
| 5,531,715 A | 7/1996 | Engelson et al. |
| 5,533,986 A | 7/1996 | Mottola et al. |
| 5,542,917 A | 8/1996 | Nita et al. |
| 5,542,935 A | 8/1996 | Unger et al. |
| 5,558,092 A | 9/1996 | Unger et al. |
| 5,558,642 A | 9/1996 | Schweich, Jr. et al. |
| 5,560,362 A | 10/1996 | Sliwa et al. |
| 5,562,608 A | 10/1996 | Sekins et al. |
| 5,567,687 A | 10/1996 | Magda et al. |
| 5,569,197 A | 10/1996 | Helmus et al. |
| 5,569,198 A | 10/1996 | Racchini |
| 5,580,575 A | 12/1996 | Unger et al. |
| 5,582,586 A | 12/1996 | Tachibana et al. |
| 5,585,112 A | 12/1996 | Unger et al. |
| 5,586,982 A | 12/1996 | Abela |
| 5,588,432 A | 12/1996 | Crowley |
| 5,588,962 A | 12/1996 | Nicholas et al. |
| 5,594,136 A | 1/1997 | Sessler et al. |
| 5,599,326 A | 2/1997 | Carter |
| 5,599,923 A | 2/1997 | Sessler et al. |
| 5,603,327 A | 2/1997 | Eberle et al. |
| 5,603,694 A | 2/1997 | Brown et al. |
| 5,606,974 A | 3/1997 | Castellano et al. |
| 5,609,574 A | 3/1997 | Kaplan et al. |
| 5,616,342 A | 4/1997 | Lyons |
| 5,617,851 A | 4/1997 | Lipkovker |
| 5,618,275 A | 4/1997 | Bock |
| 5,620,409 A | 4/1997 | Venuto et al. |
| 5,620,479 A | 4/1997 | Diederich |
| 5,624,382 A | 4/1997 | Oppelt et al. |
| 5,628,728 A | 5/1997 | Tachibana et al. |
| 5,628,730 A | 5/1997 | Shapland et al. |
| 5,630,837 A | 5/1997 | Crowley |
| 5,632,970 A | 5/1997 | Sessler et al. |
| D380,543 S | 7/1997 | Piontek et al. |
| 5,648,098 A | 7/1997 | Porter |
| 5,656,016 A | 8/1997 | Ogden |
| 5,660,180 A | 8/1997 | Malinowski et al. |
| 5,660,909 A | 8/1997 | Tachibana et al. |
| 5,663,327 A | 9/1997 | Tambo et al. |
| 5,665,076 A | 9/1997 | Roth et al. |
| 5,681,296 A | 10/1997 | Ishida |
| 5,688,364 A | 11/1997 | Sato |
| 5,694,936 A | 12/1997 | Fujimoto et al. |
| 5,695,460 A | 12/1997 | Siegel et al. |
| 5,697,897 A | 12/1997 | Buchholtz et al. |
| 5,707,608 A | 1/1998 | Liu |
| 5,713,831 A | 2/1998 | Olsson |

(56) References Cited

U.S. PATENT DOCUMENTS

| | | |
|---|---|---|
| 5,713,848 A | 2/1998 | Dubrul et al. |
| 5,715,825 A | 2/1998 | Crowley |
| 5,718,921 A | 2/1998 | Mathiowitz et al. |
| 5,720,710 A | 2/1998 | Tachibana et al. |
| 5,724,976 A | 3/1998 | Mine et al. |
| 5,725,494 A | 3/1998 | Brisken |
| 5,728,062 A | 3/1998 | Brisken |
| 5,733,315 A | 3/1998 | Burdette et al. |
| 5,733,572 A | 3/1998 | Unger et al. |
| 5,735,811 A | 4/1998 | Brisken |
| 5,752,930 A | 5/1998 | Rise et al. |
| 5,766,902 A | 6/1998 | Craig et al. |
| 5,770,222 A | 6/1998 | Unger et al. |
| 5,772,627 A | 6/1998 | Acosta et al. |
| 5,772,632 A | 6/1998 | Forman |
| 5,775,338 A | 7/1998 | Hastings |
| 5,776,429 A | 7/1998 | Unger et al. |
| 5,779,644 A | 7/1998 | Eberle et al. |
| 5,779,673 A | 7/1998 | Roth et al. |
| 5,782,811 A | 7/1998 | Samson et al. |
| 5,800,421 A | 9/1998 | Lemelson |
| 5,807,395 A | 9/1998 | Mulier et al. |
| 5,817,021 A | 10/1998 | Reichenberger |
| 5,817,048 A | 10/1998 | Lawandy |
| 5,823,962 A | 10/1998 | Schaetzle et al. |
| 5,824,005 A | 10/1998 | Motamed et al. |
| 5,827,203 A | 10/1998 | Nita |
| 5,827,313 A | 10/1998 | Ream |
| 5,827,529 A | 10/1998 | Ono et al. |
| 5,834,880 A | 11/1998 | Venkataramani et al. |
| 5,836,440 A | 11/1998 | Mindich |
| 5,836,896 A | 11/1998 | Rosenschein |
| 5,836,940 A | 11/1998 | Gregory |
| 5,840,031 A | 11/1998 | Crowley |
| 5,842,994 A | 12/1998 | Tenhoff et al. |
| 5,843,109 A | 12/1998 | Mehta et al. |
| 5,846,218 A | 12/1998 | Brisken et al. |
| 5,846,517 A | 12/1998 | Unger |
| 5,849,727 A | 12/1998 | Porter et al. |
| 5,876,345 A | 3/1999 | Eaton et al. |
| 5,876,989 A | 3/1999 | Berg et al. |
| 5,895,356 A | 4/1999 | Andrus et al. |
| 5,895,358 A | 4/1999 | Becker et al. |
| 5,895,398 A | 4/1999 | Wensel et al. |
| 5,897,503 A | 4/1999 | Lyon et al. |
| 5,908,445 A | 6/1999 | Whayne et al. |
| 5,916,192 A | 6/1999 | Nita et al. |
| 5,922,687 A | 7/1999 | Mann et al. |
| 5,925,016 A | 7/1999 | Chornenky et al. |
| 5,928,186 A | 7/1999 | Homsma et al. |
| 5,931,805 A | 8/1999 | Brisken |
| 5,934,284 A | 8/1999 | Plaia et al. |
| 5,935,124 A | 8/1999 | Klumb et al. |
| 5,938,595 A | 8/1999 | Glass et al. |
| 5,941,068 A | 8/1999 | Brown et al. |
| 5,941,868 A | 8/1999 | Kaplan et al. |
| 5,941,896 A | 8/1999 | Kerr |
| 5,951,494 A | 9/1999 | Wang et al. |
| 5,957,851 A | 9/1999 | Hossack |
| 5,957,882 A | 9/1999 | Nita et al. |
| 5,957,941 A | 9/1999 | Ream |
| 5,971,949 A | 10/1999 | Levin et al. |
| 5,976,120 A | 11/1999 | Chow et al. |
| 5,984,882 A | 11/1999 | Rosenschein et al. |
| 5,997,497 A | 12/1999 | Nita et al. |
| 6,001,069 A | 12/1999 | Tachibana et al. |
| 6,004,069 A | 12/1999 | Sudbury |
| 6,004,269 A | 12/1999 | Crowley et al. |
| 6,007,514 A | 12/1999 | Nita |
| 6,024,703 A | 2/2000 | Zanelli et al. |
| 6,024,718 A | 2/2000 | Chen et al. |
| 6,027,515 A | 2/2000 | Cimino |
| 6,030,374 A | 2/2000 | McDaniel |
| 6,033,397 A | 3/2000 | Laufer et al. |
| 6,044,845 A | 4/2000 | Lewis |
| 6,053,868 A | 4/2000 | Geistert et al. |
| 6,059,731 A | 5/2000 | Seward et al. |
| 6,063,069 A | 5/2000 | Cragg et al. |
| 6,066,123 A | 5/2000 | Liking et al. |
| 6,068,857 A | 5/2000 | Weitschies et al. |
| 6,078,830 A | 6/2000 | Levin et al. |
| D427,574 S | 7/2000 | Sawada et al. |
| 6,086,573 A | 7/2000 | Siegel et al. |
| 6,088,613 A | 7/2000 | Unger |
| 6,089,573 A | 7/2000 | Udagawa |
| 6,096,000 A | 8/2000 | Tachibana et al. |
| 6,096,070 A | 8/2000 | Ragheb et al. |
| 6,110,098 A | 8/2000 | Renirie et al. |
| 6,110,314 A | 8/2000 | Nix et al. |
| 6,113,546 A | 9/2000 | Suorsa et al. |
| 6,113,558 A | 9/2000 | Rosenschein et al. |
| 6,113,570 A | 9/2000 | Siegel et al. |
| 6,117,101 A | 9/2000 | Diederich et al. |
| 6,117,858 A | 9/2000 | Porter et al. |
| 6,120,454 A | 9/2000 | Suorsa et al. |
| RE36,939 E | 10/2000 | Tachibana et al. |
| 6,135,971 A | 10/2000 | Hutchinson et al. |
| 6,135,976 A | 10/2000 | Tachibana et al. |
| 6,136,792 A | 10/2000 | Henderson |
| 6,143,013 A | 11/2000 | Samson et al. |
| 6,144,869 A | 11/2000 | Berner et al. |
| 6,149,596 A | 11/2000 | Bancroft |
| 6,149,599 A | 11/2000 | Schlesinger et al. |
| 6,176,842 B1 | 1/2001 | Tachibana et al. |
| 6,190,315 B1 | 2/2001 | Kost et al. |
| 6,190,355 B1 | 2/2001 | Hastings |
| 6,196,973 B1 | 3/2001 | Lazenby et al. |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman et al. |
| 6,235,024 B1 | 5/2001 | Tu |
| 6,238,347 B1 | 5/2001 | Nix et al. |
| 6,241,703 B1 | 6/2001 | Levin et al. |
| 6,245,747 B1 | 6/2001 | Porter et al. |
| 6,261,246 B1 | 7/2001 | Pantages et al. |
| 6,270,460 B1 | 8/2001 | McCartan et al. |
| 6,277,077 B1 | 8/2001 | Brisken et al. |
| 6,283,920 B1 | 9/2001 | Eberle et al. |
| 6,287,271 B1 | 9/2001 | Dubrul et al. |
| 6,295,990 B1 | 10/2001 | Lewis et al. |
| 6,296,610 B1 | 10/2001 | Schneider et al. |
| 6,296,619 B1 | 10/2001 | Brisken et al. |
| 6,298,264 B1 | 10/2001 | Zhong et al. |
| 6,299,597 B1 | 10/2001 | Buscemi et al. |
| 6,309,370 B1 | 10/2001 | Haim et al. |
| 6,312,402 B1 | 11/2001 | Hansmann |
| 6,319,220 B1 | 11/2001 | Bylsma |
| 6,322,513 B1 | 11/2001 | Schregel |
| 6,346,098 B1 | 2/2002 | Yock et al. |
| 6,356,776 B1 | 3/2002 | Berner et al. |
| 6,361,500 B1 | 3/2002 | Masters |
| 6,361,554 B1 | 3/2002 | Brisken |
| 6,366,719 B1 | 4/2002 | Heath et al. |
| 6,368,315 B1 | 4/2002 | Gillis et al. |
| 6,372,498 B2 | 4/2002 | Newman et al. |
| 6,379,320 B1 | 4/2002 | Lafon et al. |
| 6,387,035 B1 | 5/2002 | Jung et al. |
| 6,387,052 B1 | 5/2002 | Quinn et al. |
| 6,391,042 B1 | 5/2002 | Cimino |
| 6,394,956 B1 | 5/2002 | Chandrasekaran et al. |
| 6,394,997 B1 | 5/2002 | Lemelson |
| 6,398,772 B1 | 6/2002 | Bond et al. |
| 6,398,792 B1 | 6/2002 | O'Connor |
| 6,416,740 B1 | 7/2002 | Unger |
| 6,423,026 B1 | 7/2002 | Gesswein et al. |
| 6,425,853 B1 | 7/2002 | Edwards |
| 6,433,464 B2 | 8/2002 | Jones |
| 6,435,189 B1 | 8/2002 | Lewis et al. |
| 6,437,487 B1 | 8/2002 | Mohr et al. |
| 6,454,737 B1 | 9/2002 | Nita et al. |
| 6,454,757 B1 | 9/2002 | Nita et al. |

(56) References Cited

U.S. PATENT DOCUMENTS

| | | |
|---|---|---|
| 6,456,863 B1 | 9/2002 | Levin et al. |
| 6,461,296 B1 | 10/2002 | Desai |
| 6,461,314 B1 | 10/2002 | Pant et al. |
| 6,461,383 B1 | 10/2002 | Gesswein et al. |
| 6,461,586 B1 | 10/2002 | Unger |
| 6,464,680 B1 | 10/2002 | Brisken et al. |
| 6,471,683 B2 | 10/2002 | Drasler et al. |
| 6,478,765 B2 | 11/2002 | Siegel et al. |
| 6,485,430 B1 | 11/2002 | Quinn et al. |
| 6,485,853 B1 | 11/2002 | Pettit et al. |
| 6,493,731 B1 | 12/2002 | Jones et al. |
| 6,494,891 B1 | 12/2002 | Cornish et al. |
| 6,503,202 B1 | 1/2003 | Hossack et al. |
| 6,506,584 B1 | 1/2003 | Chandler et al. |
| 6,508,775 B2 | 1/2003 | McKenzie et al. |
| 6,508,816 B2 | 1/2003 | Shadduck |
| 6,511,478 B1 | 1/2003 | Burnside et al. |
| 6,524,251 B2 | 2/2003 | Rabiner et al. |
| 6,524,271 B2 | 2/2003 | Brisken et al. |
| 6,524,300 B2 | 2/2003 | Meglin |
| 6,527,759 B1 | 3/2003 | Tachibana et al. |
| 6,527,761 B1 | 3/2003 | Soltesz et al. |
| 6,537,224 B2 | 3/2003 | Mauchamp et al. |
| 6,537,306 B1 | 3/2003 | Burdette et al. |
| 6,542,767 B1 | 4/2003 | McNichols et al. |
| 6,544,259 B1 | 4/2003 | Tsaliovich |
| 6,548,047 B1 | 4/2003 | Unger |
| 6,551,337 B1 | 4/2003 | Rabiner et al. |
| 6,558,366 B1 | 5/2003 | Drasler et al. |
| 6,560,837 B1 | 5/2003 | Hodjat et al. |
| 6,561,998 B1 | 5/2003 | Roth et al. |
| 6,562,021 B1 | 5/2003 | Derbin et al. |
| 6,565,552 B1 | 5/2003 | Barbut |
| 6,575,922 B1 | 6/2003 | Fearnside et al. |
| 6,575,956 B1 | 6/2003 | Brisken et al. |
| 6,579,277 B1 | 6/2003 | Rabiner et al. |
| 6,579,279 B1 | 6/2003 | Rabiner et al. |
| 6,582,392 B1 | 6/2003 | Bennett et al. |
| 6,585,678 B1 | 7/2003 | Tachibana et al. |
| 6,585,763 B1 | 7/2003 | Keilman et al. |
| 6,589,182 B1 | 7/2003 | Loftman et al. |
| 6,589,253 B1 | 7/2003 | Cornish et al. |
| 6,594,514 B2 | 7/2003 | Berner et al. |
| 6,599,288 B2 | 7/2003 | Maguire et al. |
| 6,605,084 B2 | 8/2003 | Acker et al. |
| 6,607,502 B1 | 8/2003 | Maguire et al. |
| 6,623,444 B2 | 9/2003 | Babaev |
| 6,635,017 B1 | 10/2003 | Moehring et al. |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,536 B2 | 11/2003 | Mathews et al. |
| 6,652,547 B2 | 11/2003 | Rabiner et al. |
| 6,652,581 B1 | 11/2003 | Ding |
| 6,660,013 B2 | 12/2003 | Rabiner et al. |
| 6,663,613 B1 | 12/2003 | Evans et al. |
| 6,676,626 B1 | 1/2004 | Bennett et al. |
| 6,680,301 B2 | 1/2004 | Berg et al. |
| 6,682,502 B2 | 1/2004 | Bond et al. |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,699,269 B2 | 3/2004 | Khanna |
| 6,711,953 B2 | 3/2004 | Hayashi et al. |
| 6,723,063 B1 | 4/2004 | Zhang et al. |
| 6,723,064 B2 | 4/2004 | Babaev |
| 6,726,698 B2 | 4/2004 | Cimino |
| 6,730,048 B1 | 5/2004 | Hare et al. |
| 6,733,450 B1 | 5/2004 | Alexandrov et al. |
| 6,733,451 B2 | 5/2004 | Rabiner et al. |
| 6,733,515 B1 | 5/2004 | Edwards et al. |
| 6,740,040 B1 | 5/2004 | Mandrusov et al. |
| 6,758,857 B2 | 7/2004 | Cioanta et al. |
| 6,764,860 B2 | 7/2004 | Lee |
| 6,767,345 B2 | 7/2004 | St. Germain et al. |
| 6,794,369 B2 | 9/2004 | Newman et al. |
| 6,796,992 B2 | 9/2004 | Barbut |
| 6,797,293 B2 | 9/2004 | Shin et al. |
| 6,824,515 B2 | 11/2004 | Suorsa et al. |
| 6,824,575 B1 | 11/2004 | Otomo et al. |
| 6,830,577 B2 | 12/2004 | Nash et al. |
| 6,849,062 B2 | 2/2005 | Kantor |
| 6,850,790 B2 | 2/2005 | Berner et al. |
| 6,855,123 B2 | 2/2005 | Nita |
| 6,866,670 B2 | 3/2005 | Rabiner et al. |
| 6,896,659 B2 | 5/2005 | Conston et al. |
| 6,905,505 B2 | 6/2005 | Nash et al. |
| 6,908,448 B2 | 6/2005 | Redding |
| 6,913,581 B2 | 7/2005 | Corl et al. |
| 6,921,371 B2 | 7/2005 | Wilson |
| 6,929,632 B2 | 8/2005 | Nita et al. |
| 6,929,633 B2 | 8/2005 | Evans et al. |
| 6,942,620 B2 | 9/2005 | Nita et al. |
| 6,942,677 B2 | 9/2005 | Nita et al. |
| 6,945,937 B2 | 9/2005 | Culp et al. |
| 6,958,040 B2 | 10/2005 | Oliver et al. |
| 6,958,059 B2 | 10/2005 | Zadno-Azizi |
| 6,979,293 B2 | 12/2005 | Hansmann et al. |
| 6,985,771 B2 | 1/2006 | Fischell et al. |
| 7,025,425 B2 | 4/2006 | Kovatchev et al. |
| 7,077,820 B1 | 7/2006 | Kadziauskas et al. |
| D526,655 S | 8/2006 | McDougall et al. |
| 7,084,118 B2 | 8/2006 | Armstrong et al. |
| 7,089,063 B2 | 8/2006 | Lesh et al. |
| 7,137,963 B2 | 11/2006 | Nita et al. |
| 7,141,044 B2 | 11/2006 | Gentsler |
| D534,654 S | 1/2007 | Hayamizu |
| 7,166,098 B1 | 1/2007 | Steward et al. |
| 7,174,199 B2 | 2/2007 | Berner et al. |
| 7,178,109 B2 | 2/2007 | Hewson et al. |
| 7,186,246 B2 | 3/2007 | Bennett et al. |
| 7,220,233 B2 | 5/2007 | Nita et al. |
| 7,220,239 B2 | 5/2007 | Wilson et al. |
| 7,235,063 B2 | 6/2007 | D'Antonio et al. |
| 7,264,597 B2 | 9/2007 | Cathignol |
| D555,165 S | 11/2007 | Myers et al. |
| 7,300,414 B1 | 11/2007 | Holland et al. |
| 7,308,303 B2 | 12/2007 | Whitehurst et al. |
| 7,309,334 B2 | 12/2007 | von Hoffmann |
| 7,335,180 B2 | 2/2008 | Nita et al. |
| D564,094 S | 3/2008 | Hayashi |
| D564,661 S | 3/2008 | Hayashi |
| 7,341,569 B2 | 3/2008 | Soltani et al. |
| 7,344,509 B2 | 3/2008 | Hynynen et al. |
| 7,384,407 B2 | 6/2008 | Rodriguez et al. |
| D574,961 S | 8/2008 | Kitahara et al. |
| 7,413,556 B2 | 8/2008 | Zhang et al. |
| 7,416,535 B1 | 8/2008 | Kenny |
| D578,543 S | 10/2008 | Ulm et al. |
| 7,440,798 B2 | 10/2008 | Redding, Jr. |
| 7,503,895 B2 | 3/2009 | Rabiner et al. |
| D592,754 S | 5/2009 | Koike et al. |
| D593,117 S | 5/2009 | Lettau |
| 7,540,852 B2 | 6/2009 | Nita et al. |
| 7,567,016 B2 | 7/2009 | Lu et al. |
| 7,604,608 B2 | 10/2009 | Nita et al. |
| 7,613,516 B2 | 11/2009 | Cohen et al. |
| 7,613,664 B2 | 11/2009 | Riezler et al. |
| 7,615,030 B2 | 11/2009 | Murphy et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,715,908 B2 | 5/2010 | Moran et al. |
| 7,717,853 B2 | 5/2010 | Nita |
| D617,332 S | 6/2010 | Loken et al. |
| 7,727,178 B2 | 6/2010 | Wilson et al. |
| 7,758,509 B2 | 7/2010 | Angelsen et al. |
| D622,841 S | 8/2010 | Bierman |
| 7,771,372 B2 | 8/2010 | Wilson |
| 7,774,933 B2 | 8/2010 | Wilson et al. |
| 7,789,830 B2 | 9/2010 | Ishida et al. |
| 7,818,854 B2 | 10/2010 | Wilson |
| 7,828,754 B2 | 11/2010 | Furuhata et al. |

(56) References Cited

U.S. PATENT DOCUMENTS

| | | |
|---|---|---|
| 7,828,762 B2 | 11/2010 | Wilson et al. |
| D630,727 S | 1/2011 | Petrovic et al. |
| 7,862,576 B2 | 1/2011 | Gurm |
| 7,874,985 B2 | 1/2011 | Kovatchev et al. |
| 7,901,359 B2 | 3/2011 | Mandrusov et al. |
| 7,914,509 B2 | 3/2011 | Bennett et al. |
| D637,287 S | 5/2011 | Mudd et al. |
| 7,976,483 B2 | 7/2011 | Bennett et al. |
| D643,117 S | 8/2011 | Onuma |
| D644,649 S | 9/2011 | Fullington et al. |
| 8,012,092 B2 | 9/2011 | Powers et al. |
| 8,062,566 B2 | 11/2011 | Nita et al. |
| D651,212 S | 12/2011 | Bakhreiba et al. |
| 8,123,789 B2 | 2/2012 | Khanna |
| 8,152,753 B2 | 4/2012 | Nita et al. |
| D658,667 S | 5/2012 | Cho et al. |
| D659,151 S | 5/2012 | Loken et al. |
| 8,167,831 B2 | 5/2012 | Wilson et al. |
| 8,192,363 B2 | 6/2012 | Soltani et al. |
| 8,192,391 B2 | 6/2012 | Soltani et al. |
| D664,257 S | 7/2012 | Patil |
| 8,226,629 B1 | 7/2012 | Keilman et al. |
| D664,985 S | 8/2012 | Tanghe et al. |
| 8,298,147 B2 | 10/2012 | Huennekens et al. |
| D670,714 S | 11/2012 | Majeed et al. |
| D670,716 S | 11/2012 | Majeed et al. |
| D670,725 S | 11/2012 | Mori et al. |
| D671,552 S | 11/2012 | Mori et al. |
| D676,562 S | 2/2013 | Marzynski |
| 8,366,620 B2 | 2/2013 | Nita |
| D685,815 S | 7/2013 | Bork et al. |
| D692,907 S | 11/2013 | Schuller et al. |
| D694,774 S | 12/2013 | Schuller et al. |
| D698,925 S | 2/2014 | Marzynski |
| D700,343 S | 2/2014 | Liu |
| 8,690,818 B2 | 4/2014 | Bennett et al. |
| 8,696,612 B2 | 4/2014 | Wilson et al. |
| 8,740,835 B2 | 6/2014 | Soltani et al. |
| 8,762,880 B2 | 6/2014 | Dukhon et al. |
| D709,515 S | 7/2014 | Elston et al. |
| 8,764,700 B2 | 7/2014 | Zhang et al. |
| 8,771,186 B2 | 7/2014 | Kinsley et al. |
| D711,001 S | 8/2014 | Boudier |
| D714,339 S | 9/2014 | Hendrickson et al. |
| 8,819,928 B2 | 9/2014 | Nix et al. |
| D714,948 S | 10/2014 | Vaccarella |
| 8,852,166 B1 | 10/2014 | Keilman et al. |
| D725,784 S | 3/2015 | Xia et al. |
| D733,178 S | 6/2015 | Omiya |
| 9,044,568 B2 | 6/2015 | Wilcox et al. |
| 9,050,123 B2 | 6/2015 | Krause et al. |
| D733,720 S | 7/2015 | Mueller et al. |
| D733,738 S | 7/2015 | Omiya |
| D734,475 S | 7/2015 | Ross |
| 9,107,590 B2 | 8/2015 | Hansmann et al. |
| D741,351 S | 10/2015 | Kito et al. |
| D741,871 S | 10/2015 | Chung et al. |
| 9,192,566 B2 | 11/2015 | Soltani et al. |
| D748,124 S | 1/2016 | Jeon |
| D755,818 S | 5/2016 | Seo et al. |
| D758,397 S | 6/2016 | Lee |
| D763,298 S | 8/2016 | Hoang et al. |
| 9,415,242 B2 | 8/2016 | Wilson et al. |
| D767,583 S | 9/2016 | Xiong |
| D767,584 S | 9/2016 | Xiong |
| D772,252 S | 11/2016 | Myers et al. |
| D773,491 S | 12/2016 | Ahdritz et al. |
| D776,688 S | 1/2017 | Gamel |
| D779,539 S | 2/2017 | Lee et al. |
| 9,579,494 B2 | 2/2017 | Kersten et al. |
| D782,496 S | 3/2017 | Contreras et al. |
| D783,028 S | 4/2017 | Lee et al. |
| D788,145 S | 5/2017 | Sullivan et al. |
| D794,662 S | 8/2017 | Genstler et al. |
| D797,918 S | 9/2017 | Genstler et al. |
| 9,849,273 B2 | 12/2017 | Soltani et al. |
| D812,075 S | 3/2018 | Fukagawa |
| 9,943,675 B1 | 4/2018 | Keilman et al. |
| D819,807 S | 6/2018 | Genstler et al. |
| 10,080,878 B2 | 9/2018 | Wilson et al. |
| D831,058 S | 10/2018 | Genstler et al. |
| 10,092,742 B2 | 10/2018 | Genstler et al. |
| 10,182,833 B2 | 1/2019 | Soltani et al. |
| 10,188,410 B2 | 1/2019 | Soltani et al. |
| 10,232,196 B2 | 3/2019 | Soltani et al. |
| 2001/0000791 A1 | 5/2001 | Suorsa et al. |
| 2001/0003790 A1 | 6/2001 | Ben-haim et al. |
| 2001/0007666 A1 | 7/2001 | Hoffman et al. |
| 2001/0007861 A1 | 7/2001 | Newman et al. |
| 2001/0007940 A1 | 7/2001 | Tu et al. |
| 2001/0014775 A1 | 8/2001 | Koger et al. |
| 2001/0025190 A1 | 9/2001 | Weber et al. |
| 2001/0037106 A1 | 11/2001 | Shadduck |
| 2001/0039419 A1 | 11/2001 | Francischelli et al. |
| 2001/0041842 A1 | 11/2001 | Eberle et al. |
| 2001/0041880 A1 | 11/2001 | Brisken et al. |
| 2001/0053384 A1 | 12/2001 | Greenleaf et al. |
| 2002/0000763 A1 | 1/2002 | Jones |
| 2002/0018472 A1 | 2/2002 | Rinne et al. |
| 2002/0019644 A1 | 2/2002 | Hastings et al. |
| 2002/0022833 A1 | 2/2002 | Maguire et al. |
| 2002/0032394 A1 | 3/2002 | Brisken et al. |
| 2002/0040184 A1 | 4/2002 | Brown et al. |
| 2002/0041898 A1 | 4/2002 | Unger et al. |
| 2002/0045890 A1 | 4/2002 | Celliers et al. |
| 2002/0052620 A1 | 5/2002 | Barbut |
| 2002/0055731 A1 | 5/2002 | Atala et al. |
| 2002/0068717 A1 | 6/2002 | Borrelli |
| 2002/0068869 A1 | 6/2002 | Brisken et al. |
| 2002/0077550 A1 | 6/2002 | Rabiner et al. |
| 2002/0082238 A1 | 6/2002 | Newman et al. |
| 2002/0087083 A1 | 7/2002 | Nix et al. |
| 2002/0099292 A1 | 7/2002 | Brisken et al. |
| 2002/0123787 A1 | 9/2002 | Weiss |
| 2002/0133081 A1 | 9/2002 | Ackerman et al. |
| 2002/0133111 A1 | 9/2002 | Shadduck |
| 2002/0150901 A1 | 10/2002 | Murphy et al. |
| 2002/0151792 A1 | 10/2002 | Conston et al. |
| 2002/0173028 A1 | 11/2002 | Kapeller-Libermann et al. |
| 2002/0188276 A1 | 12/2002 | Evans et al. |
| 2002/0193708 A1 | 12/2002 | Thompson et al. |
| 2002/0198526 A1 | 12/2002 | Shaolian et al. |
| 2003/0013986 A1 | 1/2003 | Saadat |
| 2003/0023261 A1 | 1/2003 | Tomaschko et al. |
| 2003/0028173 A1 | 2/2003 | Forsberg |
| 2003/0036705 A1 | 2/2003 | Hare et al. |
| 2003/0040501 A1 | 2/2003 | Newman et al. |
| 2003/0050662 A1 | 3/2003 | Don Michael |
| 2003/0065263 A1 | 4/2003 | Hare et al. |
| 2003/0069525 A1 | 4/2003 | Brisken et al. |
| 2003/0082649 A1 | 5/2003 | Weich et al. |
| 2003/0083608 A1 | 5/2003 | Evans et al. |
| 2003/0083698 A1 | 5/2003 | Whitehurst et al. |
| 2003/0088187 A1 | 5/2003 | Saadat et al. |
| 2003/0092667 A1 | 5/2003 | Tachibana et al. |
| 2003/0109812 A1 | 6/2003 | Corl et al. |
| 2003/0114761 A1 | 6/2003 | Brown |
| 2003/0135262 A1 | 7/2003 | Dretler et al. |
| 2003/0139774 A1 | 7/2003 | Epstein et al. |
| 2003/0153833 A1 | 8/2003 | Bennett et al. |
| 2003/0157024 A1 | 8/2003 | Tachibana et al. |
| 2003/0163147 A1 | 8/2003 | Rabiner et al. |
| 2003/0167023 A1 | 9/2003 | Bennett et al. |
| 2003/0187320 A1 | 10/2003 | Freyman |
| 2003/0191446 A1 | 10/2003 | Tachibana et al. |
| 2003/0199831 A1 | 10/2003 | Morris et al. |
| 2003/0216681 A1 | 11/2003 | Zhang et al. |
| 2003/0220568 A1 | 11/2003 | Hansmann et al. |
| 2003/0233085 A1 | 12/2003 | Giammarusti |
| 2003/0236539 A1 | 12/2003 | Rabiner et al. |
| 2004/0001809 A1 | 1/2004 | Brisken et al. |
| 2004/0010290 A1 | 1/2004 | Schroeppel et al. |
| 2004/0015061 A1 | 1/2004 | Currier et al. |
| 2004/0015122 A1 | 1/2004 | Zhang et al. |

(56) References Cited

U.S. PATENT DOCUMENTS

| | | |
|---|---|---|
| 2004/0015138 A1 | 1/2004 | Currier et al. |
| 2004/0019318 A1 | 1/2004 | Wilson et al. |
| 2004/0024347 A1 | 2/2004 | Wilson et al. |
| 2004/0024393 A1 | 2/2004 | Nita et al. |
| 2004/0039311 A1 | 2/2004 | Nita et al. |
| 2004/0039329 A1 | 2/2004 | Ueberle |
| 2004/0049148 A1 | 3/2004 | Rodriguez et al. |
| 2004/0054351 A1 | 3/2004 | Deniega et al. |
| 2004/0059313 A1 | 3/2004 | Tachibana et al. |
| 2004/0068189 A1 | 4/2004 | Wilson et al. |
| 2004/0077976 A1 | 4/2004 | Wilson |
| 2004/0082857 A1 | 4/2004 | Schonenberger et al. |
| 2004/0097996 A1 | 5/2004 | Rabiner et al. |
| 2004/0106847 A1 | 6/2004 | Benderev |
| 2004/0111195 A1 | 6/2004 | Vries et al. |
| 2004/0122354 A1 | 6/2004 | Semba |
| 2004/0133232 A1 | 7/2004 | Rosenbluth et al. |
| 2004/0138570 A1 | 7/2004 | Nita et al. |
| 2004/0162571 A1 | 8/2004 | Rabiner et al. |
| 2004/0171970 A1 | 9/2004 | Schleuniger et al. |
| 2004/0171981 A1 | 9/2004 | Rabiner et al. |
| 2004/0199228 A1 | 10/2004 | Wilson |
| 2004/0210134 A1 | 10/2004 | Hynynen et al. |
| 2004/0220514 A1 | 11/2004 | Cafferata |
| 2004/0220544 A1 | 11/2004 | Heruth et al. |
| 2004/0225318 A1 | 11/2004 | Eidenschink et al. |
| 2004/0229830 A1 | 11/2004 | Tachibana et al. |
| 2004/0230116 A1 | 11/2004 | Cowan et al. |
| 2004/0236350 A1 | 11/2004 | Lewis et al. |
| 2004/0243062 A1 | 12/2004 | Henry |
| 2004/0254506 A1 | 12/2004 | Cathignol |
| 2004/0255957 A1 | 12/2004 | Cafferata |
| 2004/0265393 A1 | 12/2004 | Unger et al. |
| 2005/0010112 A1 | 1/2005 | Bennett et al. |
| 2005/0021063 A1 | 1/2005 | Hall et al. |
| 2005/0027247 A1 | 2/2005 | Carrison et al. |
| 2005/0038340 A1 | 2/2005 | Vaezy et al. |
| 2005/0043629 A1 | 2/2005 | Rabiner et al. |
| 2005/0043726 A1 | 2/2005 | McHale et al. |
| 2005/0043753 A1 | 2/2005 | Rabiner et al. |
| 2005/0054971 A1 | 3/2005 | Steen et al. |
| 2005/0065461 A1 | 3/2005 | Redding |
| 2005/0090818 A1 | 4/2005 | Pike et al. |
| 2005/0096669 A1 | 5/2005 | Rabiner et al. |
| 2005/0113688 A1 | 5/2005 | Nita et al. |
| 2005/0119679 A1 | 6/2005 | Rabiner et al. |
| 2005/0124877 A1 | 6/2005 | Nita et al. |
| 2005/0137520 A1 | 6/2005 | Rule et al. |
| 2005/0177212 A1 | 8/2005 | Njemanze |
| 2005/0187513 A1 | 8/2005 | Rabiner et al. |
| 2005/0187514 A1 | 8/2005 | Rabiner et al. |
| 2005/0192556 A1 | 9/2005 | Soltani et al. |
| 2005/0192558 A1 | 9/2005 | Bernard et al. |
| 2005/0197619 A1 | 9/2005 | Rule et al. |
| 2005/0209578 A1 | 9/2005 | Christian Evans et al. |
| 2005/0215942 A1 | 9/2005 | Abrahamson et al. |
| 2005/0215946 A1 | 9/2005 | Hansmann et al. |
| 2005/0216044 A1 | 9/2005 | Hong |
| 2005/0249667 A1 | 11/2005 | Tuszynski et al. |
| 2005/0256410 A1 | 11/2005 | Rabiner et al. |
| 2005/0277869 A1 | 12/2005 | Boukhny |
| 2005/0278633 A1 | 12/2005 | Kemp |
| 2005/0288695 A1 | 12/2005 | Jenson et al. |
| 2006/0069303 A1 | 3/2006 | Couvillon |
| 2006/0078555 A1 | 4/2006 | Hanley et al. |
| 2006/0094947 A1 | 5/2006 | Kovatchev et al. |
| 2006/0106308 A1 | 5/2006 | Hansmann et al. |
| 2006/0106375 A1 | 5/2006 | Werneth et al. |
| 2006/0116610 A1 | 6/2006 | Hare et al. |
| 2006/0142783 A1 | 6/2006 | Lewis et al. |
| 2006/0173387 A1 | 8/2006 | Hansmann et al. |
| 2006/0184070 A1 | 8/2006 | Hansmann et al. |
| 2006/0241462 A1 | 10/2006 | Chou et al. |
| 2006/0241524 A1 | 10/2006 | Lee et al. |
| 2006/0264758 A1 | 11/2006 | Hossack et al. |
| 2006/0264809 A1 | 11/2006 | Hansmann et al. |
| 2007/0005051 A1 | 1/2007 | Kampa |
| 2007/0005121 A1 | 1/2007 | Khanna |
| 2007/0016040 A1 | 1/2007 | Nita |
| 2007/0016041 A1 | 1/2007 | Nita |
| 2007/0037119 A1 | 2/2007 | Pal et al. |
| 2007/0038100 A1 | 2/2007 | Nita |
| 2007/0038158 A1 | 2/2007 | Nita et al. |
| 2007/0066900 A1 | 3/2007 | O'keeffe |
| 2007/0066978 A1 | 3/2007 | Schafer et al. |
| 2007/0083100 A1 | 4/2007 | Schulz-Stubner |
| 2007/0083120 A1 | 4/2007 | Cain et al. |
| 2007/0106203 A1 | 5/2007 | Wilson et al. |
| 2007/0112268 A1 | 5/2007 | Zhang et al. |
| 2007/0112296 A1 | 5/2007 | Wilson et al. |
| 2007/0123652 A1 | 5/2007 | Chu et al. |
| 2007/0129652 A1 | 6/2007 | Nita |
| 2007/0129761 A1 | 6/2007 | Demarais et al. |
| 2007/0142721 A1 | 6/2007 | Berner et al. |
| 2007/0149917 A1 | 6/2007 | Bennett et al. |
| 2007/0207194 A1 | 9/2007 | Grayburn et al. |
| 2007/0225619 A1 | 9/2007 | Rabiner et al. |
| 2007/0239027 A1 | 10/2007 | Nita |
| 2007/0249969 A1 | 10/2007 | Shields |
| 2007/0255252 A1 | 11/2007 | Mehta |
| 2007/0265560 A1 | 11/2007 | Soltani et al. |
| 2008/0045865 A1 | 2/2008 | Kislev |
| 2008/0065014 A1 | 3/2008 | Von Oepen et al. |
| 2008/0103417 A1 | 5/2008 | Soltani et al. |
| 2008/0109029 A1 | 5/2008 | Gurm |
| 2008/0115064 A1 | 5/2008 | Roach et al. |
| 2008/0146918 A1 | 6/2008 | Magnin et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Unger et al. |
| 2008/0208109 A1 | 8/2008 | Soltani et al. |
| 2008/0221506 A1 | 9/2008 | Rodriguez et al. |
| 2008/0228526 A1 | 9/2008 | Locke et al. |
| 2008/0235872 A1 | 10/2008 | Newkirk et al. |
| 2008/0249501 A1 | 10/2008 | Yamasaki |
| 2008/0262350 A1 | 10/2008 | Unger |
| 2008/0274097 A1 | 11/2008 | Tachibana et al. |
| 2008/0290114 A1 | 11/2008 | Cabuz et al. |
| 2008/0306499 A1 | 12/2008 | Katoh et al. |
| 2008/0312536 A1 | 12/2008 | Dala-Krishna |
| 2008/0315720 A1 | 12/2008 | Ma et al. |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0073455 A1 | 3/2009 | Onimura |
| 2009/0079415 A1 | 3/2009 | Amada |
| 2009/0099482 A1 | 4/2009 | Furuhata et al. |
| 2009/0105597 A1 | 4/2009 | Abraham |
| 2009/0105633 A1 | 4/2009 | Tachibana et al. |
| 2009/0112150 A1 | 4/2009 | Unger et al. |
| 2009/0187137 A1 | 7/2009 | Volz et al. |
| 2009/0209900 A1 | 8/2009 | Carmeli et al. |
| 2009/0216246 A1 | 8/2009 | Nita et al. |
| 2009/0221902 A1 | 9/2009 | Myhr |
| 2010/0010393 A1 | 1/2010 | Duffy et al. |
| 2010/0022920 A1 | 1/2010 | Nita et al. |
| 2010/0022944 A1 | 1/2010 | Wilcox |
| 2010/0023036 A1 | 1/2010 | Nita et al. |
| 2010/0023037 A1 | 1/2010 | Nita et al. |
| 2010/0049209 A1 | 2/2010 | Nita et al. |
| 2010/0063413 A1 | 3/2010 | Volz |
| 2010/0063414 A1 | 3/2010 | Volz |
| 2010/0081934 A1 | 4/2010 | Soltani et al. |
| 2010/0125193 A1 | 5/2010 | Zadicario |
| 2010/0143325 A1 | 6/2010 | Gurewich |
| 2010/0160779 A1 | 6/2010 | Browning et al. |
| 2010/0160780 A1 | 6/2010 | Swan et al. |
| 2010/0196348 A1 | 8/2010 | Armstrong et al. |
| 2010/0204582 A1 | 8/2010 | Lu |
| 2010/0204642 A1 | 8/2010 | Wilson et al. |
| 2010/0210940 A1 | 8/2010 | Bradley et al. |
| 2010/0217276 A1 | 8/2010 | Garrison et al. |

(56) References Cited

U.S. PATENT DOCUMENTS

| | | |
|---|---|---|
| 2010/0222715 A1 | 9/2010 | Nita |
| 2010/0256616 A1 | 10/2010 | Katoh et al. |
| 2010/0262215 A1 | 10/2010 | Gertner |
| 2010/0280505 A1 | 11/2010 | Mattiuzzi et al. |
| 2010/0292685 A1 | 11/2010 | Katoh et al. |
| 2010/0317952 A1 | 12/2010 | Budiman et al. |
| 2010/0331645 A1 | 12/2010 | Simpson et al. |
| 2010/0332142 A1 | 12/2010 | Shadforth et al. |
| 2011/0004105 A1 | 1/2011 | Soltani et al. |
| 2011/0009720 A1 | 1/2011 | Kunjan et al. |
| 2011/0009739 A1 | 1/2011 | Phillips et al. |
| 2011/0034791 A1 | 2/2011 | Moerman |
| 2011/0160621 A1 | 6/2011 | Nita |
| 2011/0200578 A1 | 8/2011 | Hanley et al. |
| 2011/0201974 A1 | 8/2011 | Soltani et al. |
| 2011/0264031 A1 | 10/2011 | Soltani et al. |
| 2011/0288449 A1 | 11/2011 | Schenkengel |
| 2011/0300078 A1 | 12/2011 | Borden et al. |
| 2011/0301506 A1 | 12/2011 | Volz |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1* | 3/2012 | Soltani ............ A61M 5/158 601/2 |
| 2012/0069285 A1 | 3/2012 | Koma et al. |
| 2012/0078140 A1 | 3/2012 | Nita |
| 2012/0089082 A1 | 4/2012 | Zhang et al. |
| 2012/0095389 A1 | 4/2012 | Bennett et al. |
| 2012/0123273 A1 | 5/2012 | Okuno et al. |
| 2012/0172795 A1 | 7/2012 | Sandhu et al. |
| 2012/0172858 A1 | 7/2012 | Harrison et al. |
| 2012/0179073 A1 | 7/2012 | Nita |
| 2012/0197277 A1 | 8/2012 | Stinis |
| 2012/0209116 A1 | 8/2012 | Hossack et al. |
| 2012/0253237 A1 | 10/2012 | Wilson et al. |
| 2012/0265123 A1 | 10/2012 | Khanna |
| 2012/0271203 A1 | 10/2012 | Soltani et al. |
| 2012/0271223 A1 | 10/2012 | Khanna |
| 2012/0289889 A1 | 11/2012 | Genstler et al. |
| 2012/0330141 A1 | 12/2012 | Brown et al. |
| 2012/0330144 A1 | 12/2012 | Brown et al. |
| 2012/0330196 A1 | 12/2012 | Nita |
| 2013/0073306 A1 | 3/2013 | Shlain et al. |
| 2013/0204166 A1 | 8/2013 | Villanueva et al. |
| 2013/0211316 A1 | 8/2013 | Wilcox et al. |
| 2013/0216593 A1 | 8/2013 | Borden et al. |
| 2013/0289398 A1 | 10/2013 | Borden et al. |
| 2013/0331738 A1 | 12/2013 | Borrelli |
| 2014/0046313 A1 | 2/2014 | Pederson et al. |
| 2014/0128734 A1 | 5/2014 | Genstler et al. |
| 2014/0155814 A1 | 6/2014 | Bennett et al. |
| 2014/0210631 A1 | 7/2014 | Zavis |
| 2014/0226901 A1 | 8/2014 | Spracklen et al. |
| 2014/0236005 A1 | 8/2014 | Chen et al. |
| 2014/0236118 A1 | 8/2014 | Unser et al. |
| 2014/0249453 A1 | 9/2014 | Wilson et al. |
| 2014/0276367 A1 | 9/2014 | Kersten et al. |
| 2014/0316329 A1 | 10/2014 | Soltani et al. |
| 2014/0343483 A1 | 11/2014 | Zhang et al. |
| 2015/0095807 A1 | 4/2015 | Duncker et al. |
| 2015/0173673 A1 | 6/2015 | Toth et al. |
| 2015/0178044 A1 | 6/2015 | Ehlen et al. |
| 2016/0030725 A1 | 2/2016 | Kersten et al. |
| 2016/0082243 A1 | 3/2016 | Genstler et al. |
| 2016/0262777 A1 | 9/2016 | Stigall et al. |
| 2016/0361528 A1 | 12/2016 | Kanz et al. |
| 2017/0007815 A1 | 1/2017 | Wilson et al. |
| 2017/0182302 A1 | 6/2017 | Kersten et al. |
| 2018/0206867 A1 | 7/2018 | Allen |
| 2019/0091458 A1 | 3/2019 | Wilson et al. |
| 2019/0099591 A1 | 4/2019 | Genstler et al. |
| 2019/0216477 A1 | 7/2019 | Soltani et al. |
| 2019/0223894 A1 | 7/2019 | Soltani et al. |
| 2019/0223895 A1 | 7/2019 | Volz |
| 2019/0269944 A1 | 9/2019 | Soltani et al. |

FOREIGN PATENT DOCUMENTS

| | | |
|---|---|---|
| CN | 1193267 A | 9/1998 |
| CN | 1309331 A | 8/2001 |
| CN | 301040544 S | 10/2009 |
| CN | 301877182 S | 4/2012 |
| DE | 3919592 A1 | 2/1990 |
| DE | 4005743 A1 | 8/1991 |
| EP | 0108658 A1 | 5/1984 |
| EP | 0122624 A2 | 10/1984 |
| EP | 0189329 A2 | 7/1986 |
| EP | 0224934 A2 | 6/1987 |
| EP | 0278074 A2 | 8/1988 |
| EP | 0327490 A1 | 8/1989 |
| EP | 0338971 A1 | 10/1989 |
| EP | 0495531 A1 | 7/1992 |
| EP | 0504881 A2 | 9/1992 |
| EP | 0520486 A2 | 12/1992 |
| EP | 0529675 A2 | 3/1993 |
| EP | 0586875 A1 | 3/1994 |
| EP | 0617913 A1 | 10/1994 |
| EP | 0625360 A1 | 11/1994 |
| EP | 0629382 A1 | 12/1994 |
| EP | 0634189 A2 | 1/1995 |
| EP | 0668052 A2 | 8/1995 |
| EP | 0670147 A1 | 9/1995 |
| EP | 0732106 A2 | 9/1996 |
| EP | 0744189 A1 | 11/1996 |
| EP | 0746245 A2 | 12/1996 |
| EP | 0788774 A1 | 8/1997 |
| EP | 1090658 A1 | 4/2001 |
| EP | 1103281 A2 | 5/2001 |
| EP | 1145731 A2 | 10/2001 |
| EP | 1252885 A2 | 10/2002 |
| EP | 1453425 A2 | 9/2004 |
| EP | 1463454 A1 | 10/2004 |
| EP | 1647232 A2 | 4/2006 |
| EP | 2015846 A2 | 1/2009 |
| EP | 2170181 A1 | 4/2010 |
| EP | 2231024 A1 | 9/2010 |
| EP | 2448636 A1 | 5/2012 |
| EP | 2494932 A2 | 9/2012 |
| EP | 2608730 A2 | 7/2013 |
| EP | 2727544 A1 | 5/2014 |
| GB | 1577551 A | 10/1980 |
| JP | 5211591 A | 9/1977 |
| JP | 5856869 A | 4/1983 |
| JP | 5963783 A | 4/1984 |
| JP | 59108378 A | 6/1984 |
| JP | 51244079 A | 10/1986 |
| JP | 02180275 A | 7/1990 |
| JP | 03063041 A | 3/1991 |
| JP | 03170172 A | 7/1991 |
| JP | 03176077 A | 7/1991 |
| JP | 03221421 A | 9/1991 |
| JP | 06233779 A | 8/1994 |
| JP | 08243168 A | 9/1996 |
| JP | 2001228601 A | 8/2001 |
| JP | 2001340336 A | 12/2001 |
| JP | 2002501402 A | 1/2002 |
| JP | 2002136537 A | 5/2002 |
| JP | 2002519095 A | 7/2002 |
| JP | 2003509152 A | 3/2003 |
| JP | 2005512630 A | 5/2005 |
| JP | 2006055649 A | 3/2006 |
| JP | 2006510449 A | 3/2006 |
| JP | 2007520281 A | 7/2007 |
| JP | 2009508630 A | 3/2009 |
| JP | D1456367 S | 11/2012 |
| SU | 614788 A1 | 7/1978 |
| SU | 654254 A2 | 3/1979 |
| SU | 931191 A1 | 5/1982 |
| SU | 1003853 A1 | 3/1983 |
| SU | 1103863 A1 | 7/1984 |
| SU | 1146059 A1 | 3/1985 |

(56) References Cited

FOREIGN PATENT DOCUMENTS

| | | |
|---|---|---|
| SU | 1648497 A1 | 5/1991 |
| WO | 80001365 A1 | 7/1980 |
| WO | 08002365 A1 | 11/1980 |
| WO | 89004142 A1 | 5/1989 |
| WO | 89005159 A1 | 6/1989 |
| WO | 89005160 A1 | 6/1989 |
| WO | 89006978 A1 | 8/1989 |
| WO | 90001300 A1 | 2/1990 |
| WO | 90001971 A1 | 3/1990 |
| WO | 91003264 A1 | 3/1991 |
| WO | 91009629 A1 | 7/1991 |
| WO | 91012772 A1 | 9/1991 |
| WO | 91019529 A1 | 12/1991 |
| WO | 92000113 A1 | 1/1992 |
| WO | 92007622 A1 | 5/1992 |
| WO | 93008738 A1 | 5/1993 |
| WO | 94005361 A1 | 3/1994 |
| WO | 94005368 A1 | 3/1994 |
| WO | 94017734 A1 | 8/1994 |
| WO | 94028873 A1 | 12/1994 |
| WO | 95001751 A1 | 1/1995 |
| WO | 95005866 A1 | 3/1995 |
| WO | 95009572 A1 | 4/1995 |
| WO | 95010233 A1 | 4/1995 |
| WO | 95015118 A1 | 6/1995 |
| WO | 9526777 A1 | 10/1995 |
| WO | 9527443 A1 | 10/1995 |
| WO | 9604955 A2 | 2/1996 |
| WO | 9607432 A1 | 3/1996 |
| WO | 9615815 A1 | 5/1996 |
| WO | 9627341 A1 | 9/1996 |
| WO | 9629935 A1 | 10/1996 |
| WO | 9635469 A1 | 11/1996 |
| WO | 9636286 A1 | 11/1996 |
| WO | 9639079 A1 | 12/1996 |
| WO | 9707735 A1 | 3/1997 |
| WO | 9719644 A1 | 6/1997 |
| WO | 9719645 A1 | 6/1997 |
| WO | 9721462 A1 | 6/1997 |
| WO | 9727808 A1 | 8/1997 |
| WO | 9740679 A1 | 11/1997 |
| WO | 9809571 A1 | 3/1998 |
| WO | 9811826 A1 | 3/1998 |
| WO | 9818391 A1 | 5/1998 |
| WO | 9829055 A2 | 7/1998 |
| WO | 9840016 A2 | 9/1998 |
| WO | 9848711 A1 | 11/1998 |
| WO | 9856462 A1 | 12/1998 |
| WO | 9858699 A1 | 12/1998 |
| WO | 9916360 A1 | 4/1999 |
| WO | 9925385 A1 | 5/1999 |
| WO | 9932184 A1 | 7/1999 |
| WO | 9933500 A2 | 7/1999 |
| WO | 9933550 A1 | 7/1999 |
| WO | 9934858 A1 | 7/1999 |
| WO | 9939647 A1 | 8/1999 |
| WO | 9939738 A1 | 8/1999 |
| WO | 9942039 A1 | 8/1999 |
| WO | 99044512 A1 | 9/1999 |
| WO | 00000095 A1 | 1/2000 |
| WO | 00012004 A1 | 3/2000 |
| WO | 00018468 A1 | 4/2000 |
| WO | 00038580 A1 | 7/2000 |
| WO | 00069341 A1 | 11/2000 |
| WO | 01013357 A1 | 2/2001 |
| WO | 0121081 A1 | 3/2001 |
| WO | 01054754 A1 | 8/2001 |
| WO | 01074255 A1 | 10/2001 |
| WO | 01087174 A1 | 11/2001 |
| WO | 01095788 A2 | 12/2001 |
| WO | 0213678 A2 | 2/2002 |
| WO | 0215803 A1 | 2/2002 |
| WO | 0215804 A1 | 2/2002 |
| WO | 03007649 A2 | 1/2003 |
| WO | 03051208 A1 | 6/2003 |
| WO | 03099382 A1 | 12/2003 |
| WO | 2004058045 A2 | 7/2004 |
| WO | 2005027756 A1 | 3/2005 |
| WO | 2005072391 A2 | 8/2005 |
| WO | 2005072409 A2 | 8/2005 |
| WO | 2005079415 A2 | 9/2005 |
| WO | 2005084552 A1 | 9/2005 |
| WO | 2005084553 A1 | 9/2005 |
| WO | 2006110773 A2 | 10/2006 |
| WO | 2007127176 A2 | 11/2007 |
| WO | 2008052186 A2 | 5/2008 |
| WO | 2008086372 A1 | 7/2008 |
| WO | 2009002881 A1 | 12/2008 |
| WO | 2009018472 A1 | 2/2009 |
| WO | 2009079415 A1 | 6/2009 |
| WO | 2010003130 A2 | 1/2010 |
| WO | 2011003031 A1 | 1/2011 |
| WO | 2011011539 A1 | 1/2011 |
| WO | 2012027722 A2 | 3/2012 |
| WO | 2014159274 A1 | 10/2014 |
| WO | 2015074036 A2 | 5/2015 |
| WO | 2016201136 A1 | 12/2016 |

OTHER PUBLICATIONS

Porter et al. "Interaction of Diagnostic Ultrasound with Synthetic Olionucleotide-Labeled Perfluorcarbon-Exposed Sonicated Dextrose Albumin Microbubbles," J Ultrasound Med, 15:557-584, 1996.

Porter et al., Thrombolytic Enhancement With Perfluorocarbom-Exposed Sonicated Dextrose Albumin Microbubbles, Nov. 1996.

Prat et al., "In Vivo Effects of Cavitation Alone or in Combination with Chemotherapy in a Peritoneal Carcinomatosis in the Rat," 1993, vol. 68, pp. 13-17.

Price et al.; Delivery of Colloidal Particles and Red Blood Cells to Tissue Through Microvessel Ruptures Created By Targeted Microbubble Destruction With Ultrasound, Sep. 29, 1998.

Rohde et al., "Intraventricular Recombinant Tissue Plasminogen Activator for Lysis of Intraventricular Haemorrhage", Journal of Neurology and Neurosurgery Psychiatry, 1995, vol. 58, pp. 447-451.

Romano et al., Latest Developments in Gene Transfer Technology: Achievements, Perspectives, and Controversies over Therapeutice Applications, (Stem Cells 18: 19-39, 2000).

Rosenschein et al., "Experimental Ultrasonic Angioplasty: Disruption of Atherosclerotic Plaques and Thrombi in Vitro and Arterial Recanalization in Vivo," Journal of the American College of Cardiology, Mar. 1, 1990, vol. 15, No. 3, pp. 711-717.

Saletes et al., "Acoustic Cavitation Generated by BiFrequency Excitation" University De Lyon, Dec. 2009.

Saletes et al., "Cavitation par Excitation Acoustique Bifréquentielle: Application á la Thrombolyse Ultrsonore," N" d'ordre 311, Universite de Lyon, Dec. 7, 2009, pp. 110.

Saletes et al., "Efficacité d'une Excitation Bifréquentielle en Thrombolyse Purement Ultrsonore," 10éme Congrés Français d'Acoustique, Universite de Lyon, Apr. 12-16, 2010.

Schäfer et al., "Influence of Ultrasound Operating Parameters on Ultrasound-Induced Thrombolysis In Vitro," Ultrasound in Medicine and Biology, vol. 31, No. 6, Mar. 2005, pp. 841-847.

Schaller et al., "Stereotactic Puncture and Lysis of Spontaneous Intracerebral Hemorrhage Using Recombinant Tissue-Plasminogen Activator", Neurosurgery, Feb. 1995, vol. 36, No. 2, pp. 328-335.

Somia et al., "Gene Therapy: Trials and Tribulations," Nature Reviews Genetics, 2000, vol. 1, pp. 91-99.

Tachibana K.; Albumin Microbubble Echo-Contrast Materials as an Enhancer for Ultrasound Accelerated Thrombolysis, Sep. 1, 1995.

Tachibana, "Enhancement of Fibrinolysis with Ultrasound Energy", JVIR, vol. 3, No. 2, May 1992, pp. 299-303.

Teernstra et al., "Stereotactic Treatment of Intracerebral Hematoma by Means of a Plasminogen Activator. A Multicenter Randomized Controlled Trial (SICHPA", Stroke, Journal of the American Heart Association, Mar. 20, 2003, pp. 968-974.

(56) References Cited

OTHER PUBLICATIONS

Tsetis et al., "Potential Benefits From Heating The High-Dose Rtpa Boluses Used in Catheter-Directed Thrombolysis for Acute/Subacute Lower Limb Ischemia", Journal of Endovascular Therapy, 2003, vol. 10, pp. 739-744.
Tsurumi, et al. "Direct Intramuscular Gene Transfer of Naked DNA Encoding Vascular Endothelial Growth Factor Augments Collateral Development and Tissue Perfusion," Circulation, 1996; 94: 3281-3290.
Unger et al., "Ultrasound Enhances Gene Expression of Liposomal Transfection," Investigative Radiology, vol. 32, No. 12, pp. 723-727, 1997.
Unger et al., "Acoustically Active Liposheres Containing Paclitaxel," vol. 11, No. 12, 1992.
Vandenburg et al., "Myocardial Risk Area and Peak Gray Level Measurement by Contrast Echocardiography Effect of Microbubble Size and Concentration, Injection Rate, and Coronary Vasodilation," American Heart Journal, Apr. 1988, vol. 115, No. 4, pp. 733-739.
Verma et al., "Gene Therapy—Promises, Problems and Prospects," Nature, 1997, vol. 389, pp. 239-242.
Wheatly et al., "Contrast Agents for Diagnostic Ultrasound: Development and Evaluation of Polymer-Coated Microbubbles," Biomaterials, Nov. 1990, vol. 11, No. 19, pp. 713-717.
Wu, Yunqiu et al., "Binding as Lysing of Blood Clots Using MRX-408," Investigative Radiology, Dec. 1998, vol. 33, No. 12, pp. 880-885.
Wyber et al., "The Use of Sonication for the Efficient Delivery of Plasmid DNA into Cells," Pharmaceutical Research, vol. 14, No. 6, pp. 750-756.
Yumita et al., "Synergistic Effect of Ultrasound and Hematoporphyrin on Sarcoma 180", Japanese Journal of Cancer Research, vol. 81, No. 3, Mar. 1990, pp. 304-308.
European Search Report in Application No. 12002917.8, dated Dec. 19, 2012.
Official Communication in European Application No. 12002917.8, dated Oct. 2, 2013.
International Search Report and Written Opinion in Application No. PCT/US2008/067783, dated Nov. 17, 2008.
Abbas, "Development of a Low Cost Shock Pressure Sensor", Thesis, Ohio University, College of Engineering and technology, Mar. 1988, pp. 149.
Akdemir et al., "Treatment of Severe Intraventricular Hemorrhage by Intraventricular Infusion of Urokinase", Neurosurgical Review, 1995, vol. 18, No. 2, pp. 95-100.
Akhtar, "Anti-HIV Therapy With Antisense Oligonucleotides and Ribozymes: Realistic Approaches or Expensive Myths?" Antimicrob Chemother, 1996, vol. 2, pp. 159-165.
Anderson, "Human Gene Therapy," Nature, 1998, vol. 392, pp. 25-30.
Butler, "Production of Microbubbles for Use as Echo Contrast Agents", Journal of Clinical Ultrasound, Jun. 1986, vol. 14, pp. 408-412.
Bleeker et al., "On the Application of Ultrasonic Contrast Agents for Blood Flowmetry and Assessment of Cardiac Perfusion", Journal of Ultrasound in Medicine, Aug. 1990, vol. 9, No. 8, pp. 461-471.
Branch, Andrea D., "A Good Antisense Molecule is Hard to Find", Trends in Biochem Science 23, Feb. 1998, pp. 45-50.
Bao et al. "Transfection of a Reporter Plasmid into Cultured Cells by Sonoporation In Vitro," Ultrasound in Medicine and Biology Journal, 1997, vol. 23, No. 6, pp. 953-959.
Broderick et al., "Guidelines for the Management of Spontaneous Intracerebral Hemorrhage: A Statement for Healthcare Professionals From a Special Writing Group of the Stroke Council, American Heart Association", Stroke, Journal of the American Heart Association, 1999, pp. 905-915.
Tachibana et al., "Liver tissue damage by ultrasound in combination with the photosensitizing drug, Photofrin II," Cancer Letters, vol. 78, (1-3), 1994, pp. 177-181.
Tachibana et al., "Enhancement of Cell killing of HL-60 cells by ultrasound in the presence of the photosensitizing drug Photofrin II," Cancer Letters, vol. 72, 1993, pp. 195-199.
Chamsuddin et al., "Catheter-directed Thrombolysis with the Endowave System in the Treatment of Acute Massive Pulmonary Embolism: A Retrospective Multicenter Case Series," Journal of Vascular and Interventional Radiology, Mar. 2008, vol. 19, No. 3, pp. 372-376.
U.S. Appl. No. 10/291,890, filed Nov. 7, 2002.
Crooke, Basic Principles of Antisense Therapeutics, Springer-Verlag, Eds, New York, 1998, pp. 1 and 4.
Deinsberger et al., "Stereotactic Aspiration and Fibrinolysis of Spontaneous Supratentorial Intracerebral Hematomas versus Conservative Treatment: A Matched-Pair Study", Zentralblatt für Neurochirurgie, Dec. 18, 2003, vol. 64, No. 4, pp. 145-150.
"EkoSonic® MACH4e", EKOS Advertisement, Venous Times, Issue 6, dated Jan. 2010, p. 3.
Fechmeier et al. "Transfection of Mammalian Cells with Plasid DNA by Scrape Loading and Sonication Loading," Proc. Natl. Acad. Sci. USA, Dec. 1987, vol. 84, pp. 8463-8467.
Feinstein et al., "Two-dimensional Contrast Echocardiography. I. In Vitro Development and Quantitative Analysis of Echo Contrast Agents", Journal of the American College of Cardiology, Jan. 1984, vol. 3, No. 1, pp. 14-20.
Feldman et al. "Optimal Techniques for Arterial Gene Transfer," Cardiovascular Research, 1997, vol. 35, pp. 391-404.
Findlay et al., "Lysis of Intraventricular Hematoma with Tissue Plasminogen Activator", Journal of Neurosurgery, 1991, vol. 74, pp. 803-807.
Frémont et al., "Prognostic Value of Echocardiographic Right/Left Ventricular End-Diastolic Diameter Ratio in Patients With Acute Pulmonary Embolism: Results From a Monocenter Registry of 1,416 Patients", Chest, Feb. 2008, vol. 133, No. 2, pp. 358-362.
Gilles et al., "Cavitation Generated by Amplitude Modulated HIFU: Investigations on the Inertial Cavitation Threshold," AIP Conference Proceedings: 6th Int. Symposium on Theraputic Ultrasound, May 21, 2007, vol. 911, pp. 171-177.
Greenleaf, William J. et al.; Arlifical Cavitation Nuclei Significantly Enhance Acoustically Induced Cell Transfection. vol. 24, No. 4 pp. 587-595, 1998.
Ho et al. "Antisense Oigonucleoties and Therapeutics for Malignant Diseases," Seminars in Drug Discovery 24, 1997, vol. 2, pp. 187-202.
Holland et al., "Thresholds for Transient Cavitation Produced by Pulsed Ultrasound in a Controlled Nuclei Environment", The Journal of the Acoustical Society of America, Nov. 1990, vol. 88, No. 5, pp. 2059-2069.
Hynynen et al.; "Small Cylindrical Ultrasound Sources for Induction of Hyperthermia Via Body Cavities or Interstitial Implants", Arizona Cancer Center and Department of Radiation Oncology, University of Arizona Health Sciences Center; vol. 9, No. 2, 1993, pp. 263-274.
Jaff et al., "Management of Massive and Submassive Pulmonary Embolism, Iliofemoral Deep Vein Thrombosis, and Chronic Thromboembolic Pulmonary Hypertension: A Scientific Statement From the American Heart Association", Challenging Forms of Venous Thromboembolic Disease, Circulation, 2011, vol. 123, pp. 1788-1830.
Japanese Journal of Cancer Research, vol. 81, No. 3, Mar. 1990, pp. 304-308.
Jeffers, R.J. et al.; Evaluation of the Effect of Cavitation Activity on Drug-Ultrasound Synergisms, 1993.
Jeffers, Russel et al.; Dimethylformamide as an Enhancer of Cavitation-Induced Cell Lysis In Vitro, vol. 97, No. 1, Jan. 1995.
Keller et al., "Automated Production and Analysis of Echo Contrast Agents", Journal of Ultrasound in Medicine, Sep. 1986, vol. 5, pp. 493-498.
Kim et al. "Ultra-sound Mediated Transfection of Mammalian Cells," Human Gene Therapy, Jul. 10, 1996, vol. 7, pp. 1339-1346.
Kim, Timothy F., "Microbubbles Show Promise for Enhancing Ultrasound Signal, Image, Other Applications", The Journal of the American Medical Association, Mar. 1989, vol. 281, No. 11, p. 1542.

(56) References Cited

OTHER PUBLICATIONS

Kotnis et al. "Optimisation of Gene Transfer into Vascular Endothelial Cells Using Electroporation," Eur J. Vasc Surg, 1995, vol. 9, pp. 71-79.

Kucher et al., "Randomized, Controlled Trial of Ultrasound-Assisted Catheter-Directed Thrombolysis for Acute Intermediate-Risk Pulmonary Embolism", Ultrasound Thrombolysis for Pulmonary Embolism, Circulation, 2014, vol. 129, pp. 479-486.

Lang et al., "Contrast Ultrasonography of the Kidney: a New Method for Evaluation of Renal Perfusion in Vivo", Circulation, 1987, vol. 75, No. 1, pp. 229-234.

Lee et al.; "Arrays of Multielement Ultrasound Applicators For Interstitial Hyperthermia"; IEEE Transactions on biomedical Engineering; vol. 46, No. 7, Jul. 1999, pp. 880-890.

Leong et al., "Polyanhydrides for Controlled Release of Bioactive Agents", Biomaterials, Sep. 1986, vol. 7, pp. 364-371.

Lin et al., "Comparison of Percutaneous Ultrasound-Accelerated Thrombolysis versus Catheter-Directed Thrombolysis in Patients with Acute Massive Pulmonary Embolism," Vascular, 2009, vol. 17, No. 3, pp. S137-S147.

Matsumoto et al., "CT-Guided Stereotaxic Evacuation of Hypertensive Intracerebral Hematomas", Journal of Neurosurgery, Sep. 1984, vol. 61, No. 3, pp. 440-448.

Mayfrank et al., "Fibrinolytic Treatment of Intraventricular Haemorrhage Preceding Surgical Repair of Ruptured Aneurysms and Arteriovenous Malformations", British Journal of Neurosurgery, 1999, vol. 13, No. 2, pp. 128-131.

Maywald et al., "Experience With Atraumatic Vascular Diagnosis With The Aid of the Ultrasonic Doppler Technique", Electromedica, 1976, vol. 2 pp. 43-48.

Meltzer et al., "The Source of Ultrasound Contrast Effect", Journal of Clinical Ultrasound, Apr. 1980, vol. 8, No. 2, pp. 121-127.

Meyer et al., "Fibrinolysis for Patients with Intermediate-Risk Pulmonary Embolism", N. Engl, J. Med., 2014, vol. 340, pp. 1402-1411.

Miller, Douglas L. et al.; Sonoporation of Cultured Cells in the Rotation Tube Exposure System, vol. 25, No. 1, 1999.

Mohadjer et al., "CT-Guided Stereotactic Fibrinolysis of Spontaneous and Hypertensive Cerebellar Hemorrhage: Long-Term Results", Journal of Neurosurgery, Aug. 1990, vol. 73, No. 2, pp. 217-222.

Niizuma et al., "CT-Guided Stereotactic Aspiration of Intracerebral Hematoma—Result of a Hematoma-Lysis Method Using Urokinase", Applied Neurophysiology, Proceedings of the Ninth Meeting of the World Society, Jul. 4-7, 1985, pp. 4.

Niizuma et al., "Results of Stereotactic Aspiration in 175 Cases of Putaminal Hemorrhage", Neurosurgery, Jun. 1989, vol. 24, No. 6, pp. 814-819.

Orkin et al., Report and Recommendations of the Panel to Assess the NIH Investment in Research on Gene Therapy, Dec. 7, 1995, pp. 1-38.

Pang et al., "Lysis of Intraventricular Blood Clot with Urokinase in a Canine Model: Part 1", Neurosurgery, 1986, vol. 19, No. 4, pp. 540-546.

\* cited by examiner

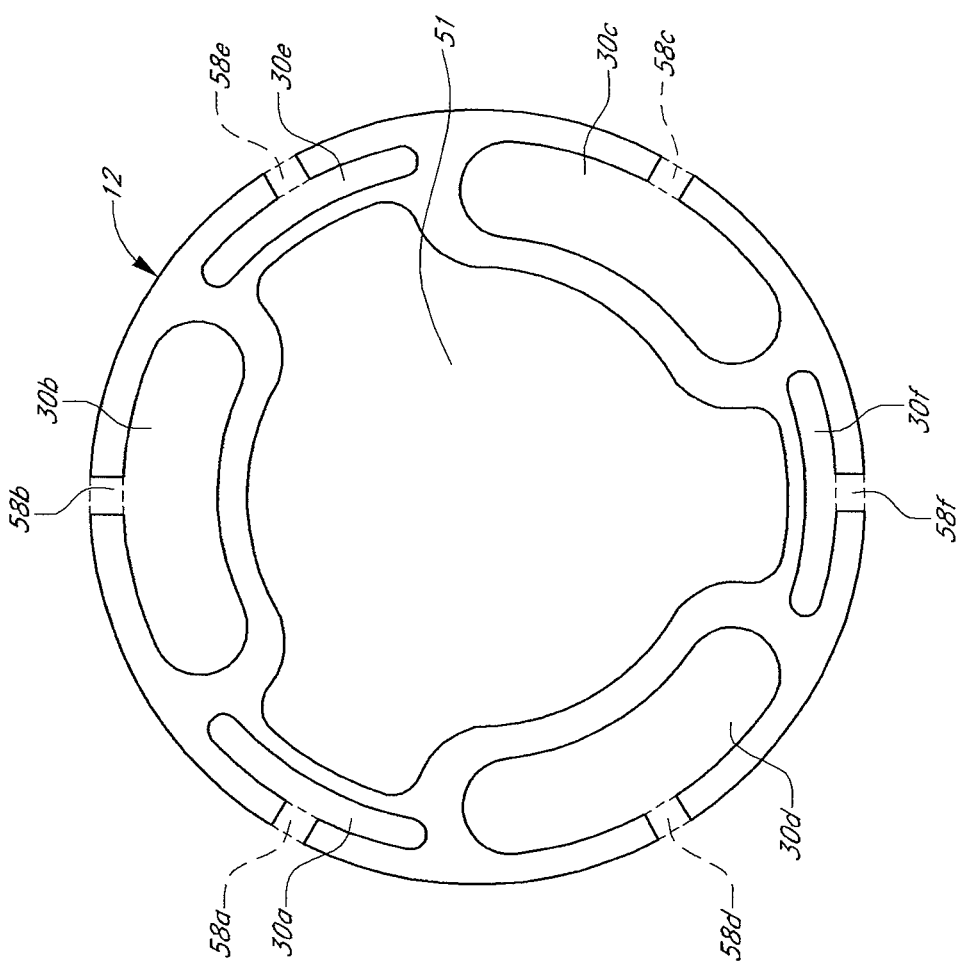

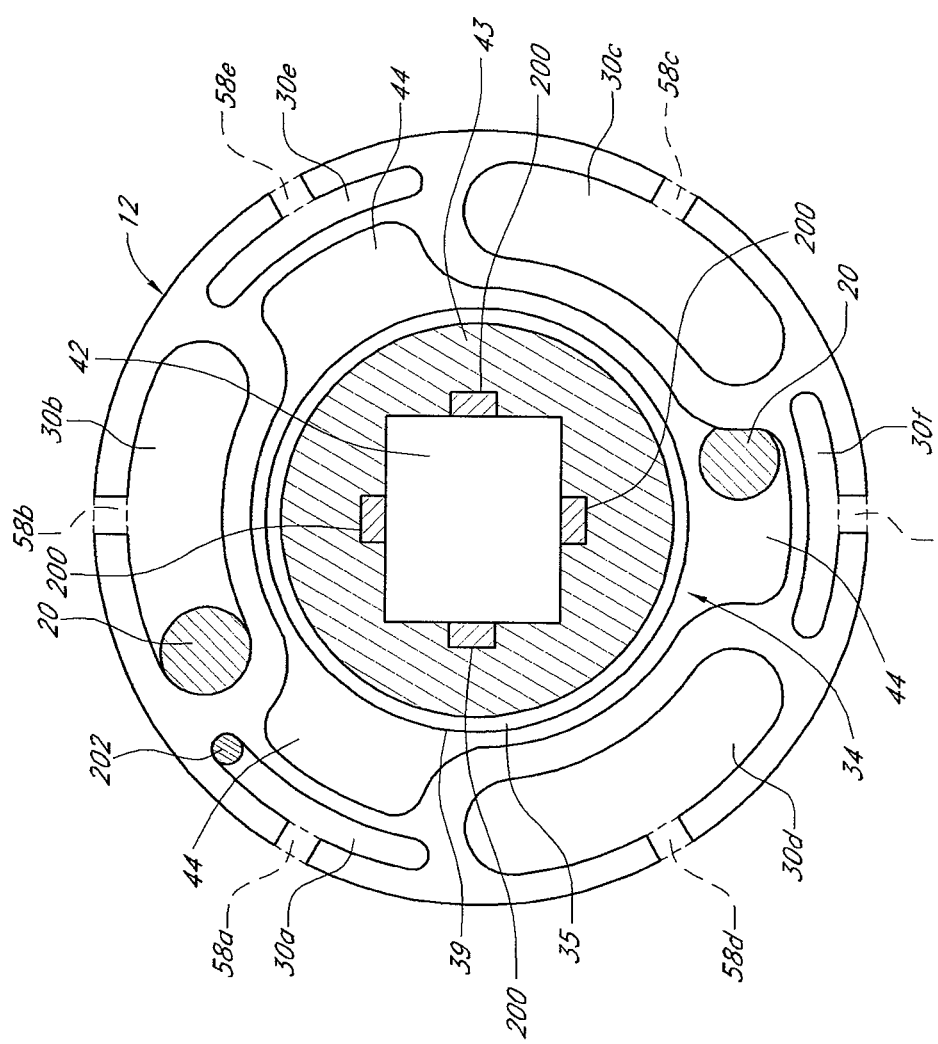

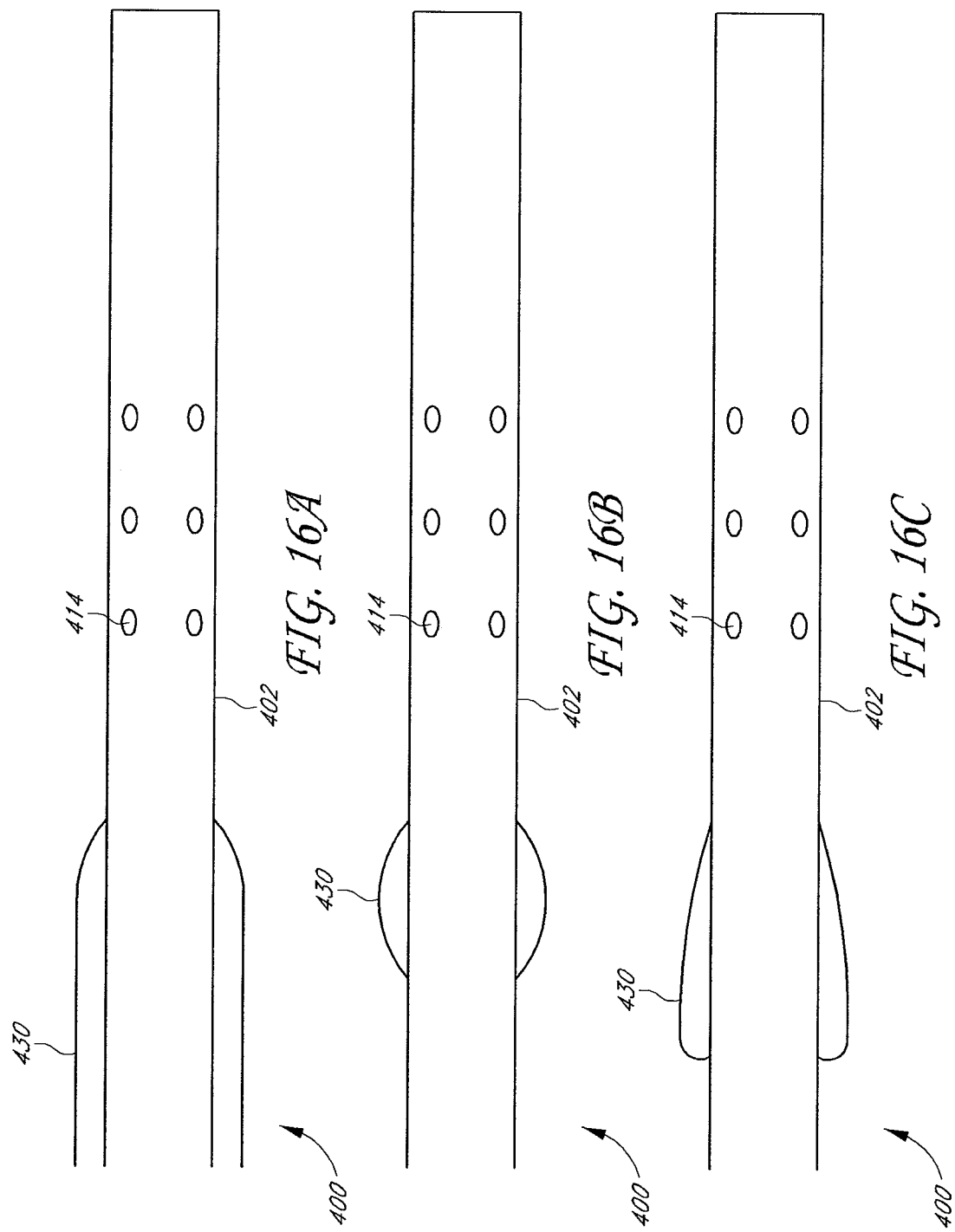

METHOD AND APPARATUS FOR TREATMENT OF INTRACRANIAL HEMORRHAGES

CROSS-REFERENCE TO RELATED APPLICATIONS

This is a continuation of U.S. patent application Ser. No. 13/726,105, filed Dec. 22, 2012, which is a continuation of U.S. patent application Ser. No. 12/143,470, filed Jun. 20, 2008, now U.S. Pat. No. 9,044,568, which claims the priority benefit of U.S. Provisional Application No. 61/032,741, filed Feb. 29, 2008, and U.S. Provisional Application No. 60/945,846, filed Jun. 22, 2007, the entire contents of these applications are hereby incorporated by reference herein.

BACKGROUND OF THE INVENTION

Field of the Invention

The present invention relates generally to the treatment of intracranial hemorrhages, and more specifically, to the treatment of intracranial hemorrhages using an ultrasound catheter.

Background of the Invention

Up to 70,000 Americans each year suffer a hemorrhagic stroke. Most of these occur in the basal ganglia, and a third of those include bleeding into the ventricles. Half of these victims will die within months, and a quarter of the survivors will have a second stroke within five years.

Bleeding in the brain occurs due to high blood pressure, aneurysms, and less frequently arterio-venous malformations (AVM), and increases in incidence with age. Factors including smoking, diabetes, and obesity play roles, as do amyloid deposits in the elderly.

With respect to stroke treatment, up to 7,000 cases per year involve surgical intervention. The objectives of surgical intervention generally include clipping bleeding aneurysms, removing bleeding AVMs, and removing clot volume in intracranial hemorrhages (ICH).

In certain applications, an interventional radiologist will insert Goldvalve detachable balloons, Guglielmi detachable coils, or Onyx liquid embolic to occlude AVMs and saccular aneurysm. These applications are primarily preventive (e.g., preventing a second bleed). Other methods of reducing further bleeding include using embolics and FVIIa, and/or maintaining intracranial pressure below mean arterial pressure. Medical therapy typically also includes head elevation, Tylenol for temperature reduction, paralytics to prevent coughing, intubation to prevent aspiration, Mannitol and diuretics to reduce fluid volume, and seizure preventatives.

Recently, lytics have been considered as a treatment option to remove obstruction in the ventricles and to reduce intracranial pressure. However, such lytic treatment has not been widely adopted because it is generally considered too slow to provide sufficient clinical benefits.

Accordingly, it would be desirable to provide a method and apparatus for rapidly reducing the volume of the blood clot in the patient's brain.

SUMMARY OF THE INVENTION

An embodiment of an ultrasound catheter for treatment of a blood clot resulting from an intracranial hemorrhage comprise an elongate tubular body having a distal portion, a proximal portion and a central lumen. The catheter further comprises a plurality of ultrasound radiating members positioned within the tubular body. A first fluid delivery lumen is formed within the elongate tubular body. The first fluid delivery lumen includes a first fluid delivery port located on a first region of the distal portion of the elongate tubular body and is configured to allow a fluid to flow from within the first fluid delivery lumen to the blood clot. In addition, a first fluid evacuation lumen is formed within the elongate tubular body. The first fluid evacuation lumen includes a first fluid evacuation port located on a second region of the distal portion of the elongate tubular body and is configured to allow a fluid to flow into the first fluid evacuation lumen.

In some embodiments, the ultrasound catheter further comprises a light source located with the ultrasound assembly. The ultrasound catheter can also have a second fluid delivery lumen formed within the elongate tubular body. The second fluid delivery lumen includes a second fluid delivery port located on a third region of the distal region of the elongate tubular body adjacent to the first region and is configured to allow a fluid to flow from within the second fluid delivery lumen to the blood clot.

In some embodiments, the ultrasound catheter further comprises a slidable sealing surface located on the proximal portion of the elongate tubular body.

In some embodiments, the ultrasound catheter further comprises a temperature sensor located within the distal portion of the elongate tubular body.

In some embodiments, the ultrasound catheter further comprises a pressure sensor located within the distal portion elongate tubular body. In some embodiments, the pressure sensor is located within the first fluid delivery lumen proximate the first fluid delivery port. In some embodiments, the pressure sensor is located within the first fluid evacuation lumen proximate the first fluid evacuation port.

An embodiment of a method for treating a blood clot resulting from an intracranial hemorrhage comprises positioning at least a portion of the distal portion of the elongate tubular body of the ultrasound catheter of claim 1 into the blood clot, activating the ultrasound assembly, delivering a lytic drug to the blood clot through the first fluid delivery lumen and evacuating a fluid around the distal portion of the elongate tubular body into the first fluid evacuation lumen.

In some embodiments, the method further comprises activating a light source located with the ultrasound assembly.

In some embodiments, the method further comprises sliding a slidable sealing surface located on the proximal portion of the enlongate tubular body towards the distal portion of the enlongate tubular body.

In some embodiments, the method further comprises measuring the temperature within a portion of the elongate tubular body with a temperature sensor located within the distal portion of the elongate tubular body.

In some embodiments, the method further comprises measuring the pressure within a portion of the elongate tubular body with a pressure sensor located within the distal portion of the elongate tubular body. In some embodiments, the pressure sensor is located within the first fluid delivery lumen proximate the first fluid delivery port. In some embodiments, the pressure sensor is located within the first fluid evacuation lumen proximate the first fluid evacuation port.

BRIEF DESCRIPTION OF THE DRAWINGS

Exemplary embodiments of the method and apparatus for treatment of intracranial hemorrhages are illustrated in the accompanying drawings, which are for illustrative purposes only. The drawings comprise the following figures, in which like numerals indicate like parts.

FIG. 2B is a cross-sectional view of another embodiment of the ultrasonic catheter of FIG. 1 taken along line 2-2.

FIG. 9B illustrates the energy delivery section of the inner core of FIG. 4 positioned within the energy delivery section of the tubular body of FIG. 2B.

FIGS. 16A-C are cross-sectional views along the longitudinal axis of an embodiment of an ultrasonic catheter having an occluder located proximal to the fluid delivery ports.

DETAILED DESCRIPTION OF THE PREFERRED EMBODIMENTS

Figure 1:
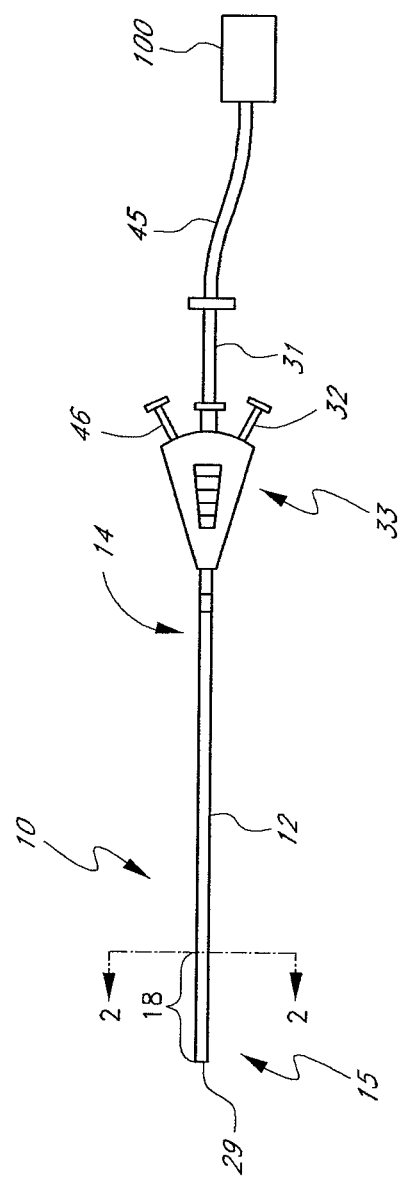
FIG. 1 is a schematic illustration of an ultrasonic catheter configured for insertion into large vessels of the human body.

As set forth above, methods and apparatuses have been developed that allow an intracranial hemorrhage and/or a subarachnoid hemorrhage to be treated using ultrasonic energy in conjunction with a therapeutic compound and/or light treatment. As used herein, the term "intracranial hemorrhage" encompasses both intracerebral hemorrhage and intraventricular hemorrhage. Although some embodiments may be disclosed with reference to intracerebral hemorrhage or intraventricular hemorrhage, the embodiments can generally be used to treat both types of intracranial hemorrhage. Disclosed herein are several exemplary embodiments of ultrasonic catheters that can be used to enhance the efficacy of therapeutic compounds at a treatment site within a patient's body. Also disclosed are exemplary methods for using such catheters. For example, as discussed in greater detail below, the ultrasonic catheters disclosed herein can be used to deliver a therapeutic compound to a blood clot in the brain, allowing at least a portion of the blood clot to be dissolved and/or removed, thereby reducing damage to brain tissue.

As used herein, the term "therapeutic compound" refers broadly, without limitation, and in addition to its ordinary meaning, to a drug, medicament, dissolution compound, genetic material or any other substance capable of effecting physiological functions. Additionally, a mixture including substances such as these is also encompassed within this definition of "therapeutic compound". Examples of therapeutic compounds include thrombolytic compounds, anti-thrombosis compounds, and other compounds used in the treatment of vascular occlusions and/or blood clots, including compounds intended to prevent or reduce clot formation, neuroprotective agents, anti-apoptotic agents, and neurotoxin scavenging agents. Exemplary therapeutic compounds include, but are not limited to, heparin, urokinase, streptokinase, tPA, rtPA, BB-10153 (manufactured by British Biotech, Oxford, UK), plasmin, IIbIIIa inhibitors, desmoteplase, caffeinol, deferoxamine, and factor VIIa.

As used herein, the terms "ultrasonic energy", "ultrasound" and "ultrasonic" refer broadly, without limitation, and in addition to their ordinary meaning, to mechanical energy transferred through longitudinal pressure or compression waves. Ultrasonic energy can be emitted as continuous or pulsed waves, depending on the parameters of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy referred to herein has a frequency between about 20 kHz and about 20 MHz. For example, in one embodiment, the ultrasonic energy has a frequency between about 500 kHz and about 20 MHz. In another embodiment, the ultrasonic energy has a frequency between about 1 MHz and about 3 MHz. In yet another embodiment, the ultrasonic energy has a frequency of about 2 MHz. In certain embodiments described herein, the average acoustic power of the ultrasonic energy is between about 0.01 watts and 300 watts. In one embodiment, the average acoustic power is about 15 watts.

As used herein, the term "ultrasound radiating member" refers broadly, without limitation, and in addition to its ordinary meaning, to any apparatus capable of producing ultrasonic energy. An ultrasonic transducer, which converts electrical energy into ultrasonic energy, is an example of an ultrasound radiating member. An exemplary ultrasonic transducer capable of generating ultrasonic energy from electrical energy is a piezoelectric ceramic oscillator. Piezoelectric ceramics typically comprise a crystalline material, such as quartz, that changes shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member. In such embodiments, a "transverse wave" can be generated along the wire. As used herein is a wave propagated along the wire in which the direction of the disturbance at each point of the medium is perpendicular to the wave vector. Some embodiments, such as embodiments incorporating a wire coupled to an ultrasound radiating member for example, are capable of generating transverse waves. See e.g., U.S. Pat. Nos. 6,866,670, 6,660,013 and 6,652,547, the entirety of which are hereby incorporated by reference herein. Other embodiments without the wire can also generate transverse waves along the body of the catheter.

In certain applications, the ultrasonic energy itself provides a therapeutic effect to the patient. Examples of such therapeutic effects include blood clot disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663.

FIG. 1 schematically illustrates an embodiment of an ultrasonic catheter 10 that can be used to treat a blood clot in the brain resulting from an intracerebral hemorrhage (ICH) and/or an intraventricular hemorrhage (IVH).

In the illustrated embodiment, the ultrasonic catheter 10 generally includes a multi-component, elongate flexible tubular body 12 having a proximal region 14 and a distal region 15. The tubular body 12 includes a flexible energy delivery section 18 located in the distal region 15. The tubular body 12 and other components of the catheter 10 can be manufactured in accordance with a variety of techniques known to an ordinarily skilled artisan. Suitable materials and dimensions can be readily selected based on the natural and anatomical dimensions of the treatment site and on the desired access site. In addition, the surface of the catheter 10 can be coated with an antimicrobial material, such as silver or a silver based compound.

In some embodiments, the tubular body 12 is between about one centimeter and about six centimeters in length. In some embodiments that are particularly suited for treating an intraventricular hemorrhage, the tubular body 12 is between about three centimeters and about six centimeters in length. In some embodiments that are particularly suited for treating an intracerebral hemorrhage, the tubular body 12 is between about one centimeter and about three centimeters in length.

In an exemplary embodiment, the tubular body proximal region 14 comprises a material that has sufficient flexibility, hoop strength, kink resistance, rigidity and structural support to push the energy delivery section 18 through an opening in the skull and then, in turn, the patient's brain tissue to a treatment site (e.g., one of the ventricles). Examples of such materials include, but are not limited to, extruded polytetrafluoroethylene ("PTFE"), polyethylenes ("PE"), polyamides and other similar materials. In certain embodiments, the tubular body proximal region 14 is reinforced by braiding, mesh or other constructions to provide increased kink resistance and ability to be pushed. For example, nickel titanium or stainless steel wires can be placed along or incorporated into the tubular body 12 to reduce kinking. Alternatively, in some embodiments, the tubular body proximal region can comprise a substantially rigid metal tube.

In one embodiment, the tubular body energy delivery section 18 can comprise a material that is thinner than the material comprising the tubular body proximal region 14. In another exemplary embodiment, the tubular body energy delivery section 18 comprises a material that has a greater acoustic transparency than the material comprising the tubular body proximal region 14. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 comprises the same material or a material of the same thickness as the proximal region 14.

In some embodiments, the distal region 15 of the catheter 10 comprises a steerable tip. The steerable tip can be constructed in a monorail configuration in which a relatively short guidewire lumen receives a guidewire. In the illustrated embodiment, the catheter 10 can be constructed using an over-the-wire design in which the guidewire is enclosed by a guidewire lumen over the entire length of the catheter 10. In some embodiments, the catheter 10 can have a lumen that is sized and shaped to receive stylet instead of or in addition to a guidewire. The stylet provides the catheter with additional column strength and can be used to guide the catheter 10 through tissue and to the blood clot, as described in more detail below. In some embodiments, the steerable tip is stiff enough to push through tissue and/or the blood clot, but also is flexible enough to be bent as the catheter 10 is steered to the blood clot. In addition, in some embodiments, the ultrasonic catheter 10 can be inserted into the lumen of and/or attached to an external ventricular drainage (EVD) catheter by, for example, a clip or hook mechanism.

Figure 2A:
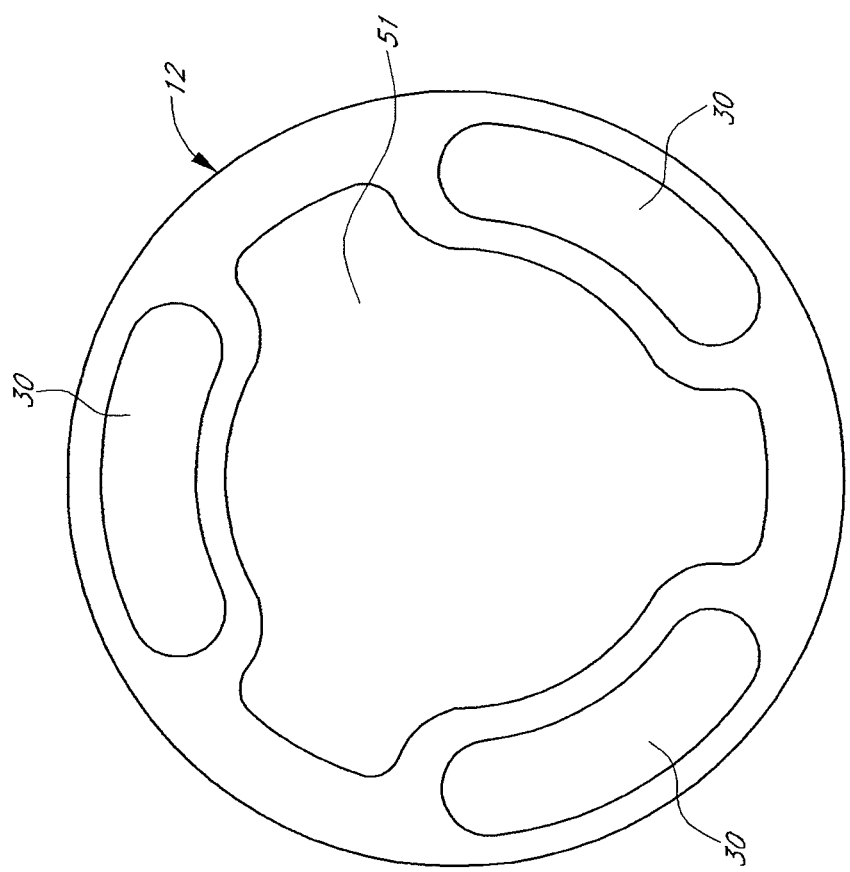
FIG. 2A is a cross-sectional view of the ultrasonic catheter of FIG. 1 taken along line 2-2.

FIG. 2A illustrates a cross section of the tubular body 12 taken along line 2-2 in FIG. 1. In the embodiment illustrated in FIG. 2A, three fluid delivery lumens 30a, 30b, 30c are incorporated into the tubular body 12. In other embodiments, more or fewer fluid delivery lumens can be incorporated into the tubular body 12. In such embodiments, the arrangement of the fluid delivery lumens 30 provides a hollow central lumen 51 passing through the tubular body 12. The cross-section of the tubular body 12, as illustrated in FIG. 2A, is substantially constant along the length of the catheter 10. Thus, in such embodiments, substantially the same cross-section is present in both the proximal region 14 and the distal region 15 of the tubular body 12, including the energy delivery section 18.

In certain embodiments, the central lumen 51 has a minimum diameter greater than about 0.030 inches. In another embodiment, the central lumen 51 has a minimum diameter greater than about 0.037 inches. Accordingly, in one embodiment of use, the tubular body 12 can be advanced over a guidewire (not shown) in order to position the body 12 within the patient. In another embodiment, the tubular body 12 is sufficiently stiff such that it can be steered directly to the target site. In an exemplary embodiment, the fluid delivery lumens 30 have dimensions of about 0.026 inches wide by about 0.0075 inches high, although other dimensions can be used in other embodiments.

In an exemplary embodiment, the central lumen 51 extends through the length of the tubular body 12. As illustrated in FIG. 1, the central lumen 51 has a distal exit port 29 and a proximal access port 31. The proximal access port 31 forms part of the backend hub 33, which is attached to the tubular body proximal region 14. In such embodiments, the backend hub also includes a cooling fluid fitting 46, which is hydraulically connected to the central lumen 51. In such embodiments, the backend hub 33 also includes a therapeutic compound inlet port 32, which is hydraulically coupled to the fluid delivery lumens 30, and which can also be hydraulically coupled to a source of therapeutic compound via a hub such as a Luer fitting.

FIG. 2B illustrates another embodiment of a cross section of the tubular body 12 taken along line 2-2 in FIG. 1. In the embodiment illustrated in FIG. 2B, six radially disposed lumens 30a-f are incorporated into the tubular body 12. Although the lumens 30a-f are not all the same size and shape in the illustrated embodiment, in other embodiments, the lumens 30a-f are substantially the same size and shape. In other embodiments, one or more lumens are sized and shaped differently than the other lumens. In other embodiments, more or fewer radially disposed lumens can be incorporated into the tubular body 12. In this embodiment, the arrangement of the radially disposed lumens 30a-f also provides a hollow central lumen 51 passing through the tubular body 12.

In some embodiments, the lumens 30a-f can be used to deliver a fluid to a treatment site and/or to evacuate a fluid from around a treatment site. As illustrated in FIG. 2B, the lumens 30a-f have ports 58a-f that allow fluids to be delivered from the lumens 30a-f and/or to be evacuated from the lumens 30a-f. These ports 58a-f can be located axially in the distal portion of the tubular body 12 and in or around the treatment portion of the tubular body 12. For example, ports 58a, corresponding to lumen 30a, can be the most proximally located ports, while ports 58b can be located just distal of ports 58a. Ports 58c can be located just distal of ports 58b, and so on such that ports 58f are the most distally located ports. In some embodiments, ports 58b-e are used to deliver fluids while the outer ports 58a and 58f are used to evacuate fluids from around the treatment site. Those of skill in the art will recognize that the number and location of the ports used for delivering fluids and for evacuating fluids can be modified, reduced or increased. In one embodiment, the catheter has at least one fluid delivery lumen and at least one evacuation lumen each with corresponding ports.

Figure 3:
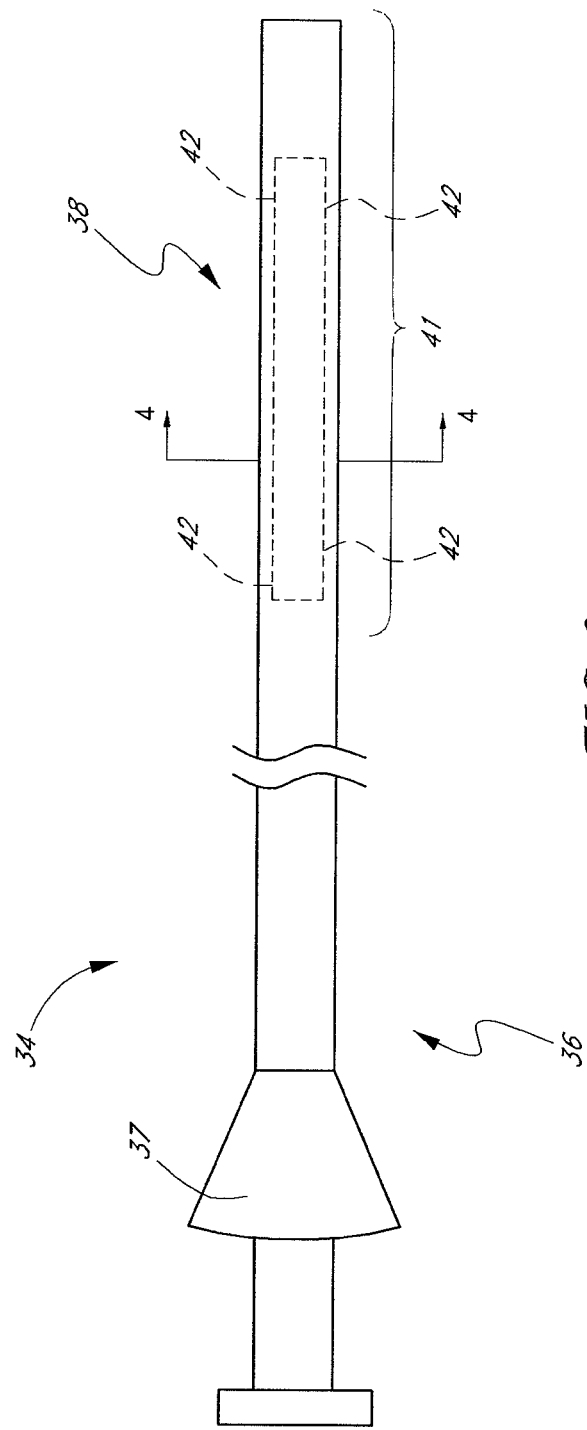
FIG. 3 is a schematic illustration of an elongate inner core configured to be positioned within the central lumen of the catheter illustrated in FIGS. 2A and 2B.

In the illustrated embodiment, the central lumen 51 is configured to receive an elongate inner core 34, an exemplary embodiment of which is illustrated in FIG. 3. In such embodiments, the elongate inner core 34 includes a proximal region 36 and a distal region 38. A proximal hub 37 is fitted on one end of the inner core proximal region 36. One or more ultrasound radiating members 40 are positioned within an inner core energy delivery section 41 that is located within the distal region 38. The ultrasound radiating members 40 form an ultrasound assembly 42, which will be described in greater detail below. In some embodiments, the inner core 34 can be slid into and/or removed from the central lumen 51 during operation. In other embodiments, the inner core 34 can be built into the catheter 10 as a non-removable component. In such an embodiment, the inner core 34 can include a guidewire lumen (not shown) and/or the catheter 10 is configured to be steerable or inserted through a guide catheter (not shown)

Figure 4:
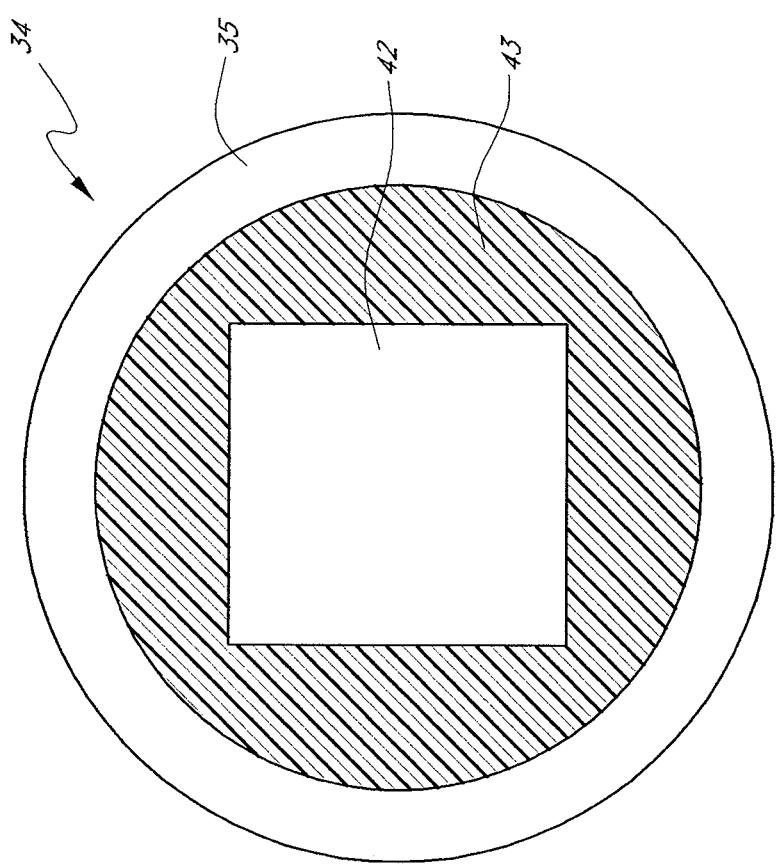
FIG. 4 is a cross-sectional view of the elongate inner core of FIG. 3 taken along line 4-4.

As shown in the cross-section illustrated in FIG. 4, which is taken along lines 4-4 in FIG. 3, in an exemplary embodiment, the inner core 34 has a cylindrical shape, with an outer diameter that permits the inner core 34 to be inserted into the central lumen 51 of the tubular body 12 via the proximal access port 31. Suitable outer diameters of the inner core 34 include, but are not limited to, between about 0.010 inches and about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 includes a cylindrical outer body 35 that houses the ultrasound assembly 42. The ultrasound assembly 42 includes wiring and ultrasound radiating members, described in greater detail in FIGS. 5 through 8, such that the ultrasonic assembly 42 is capable of radiating ultrasonic energy from the energy delivery section 41 of the inner core 34. The ultrasound assembly 42 is electrically connected to the backend hub 33, where the inner core 34 can be connected to a control system 100 via cable 45 (illustrated in FIG. 1). In an exemplary embodiment, an electrically insulating potting material 43 fills the inner core 34, surrounding the ultrasound assembly 42, thus reducing or preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
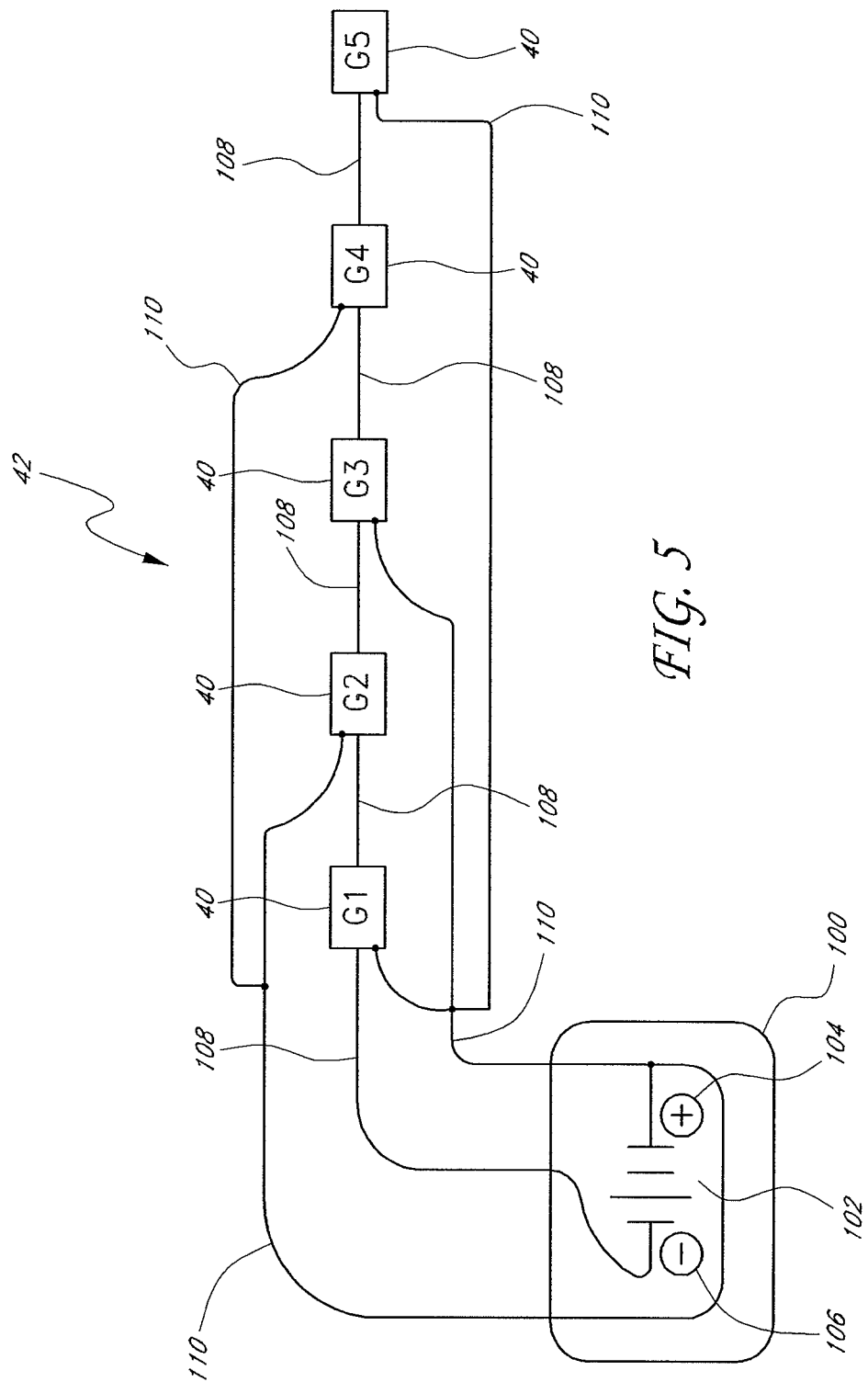
FIG. 5 is a schematic wiring diagram illustrating an exemplary technique for electrically connecting five groups of ultrasound radiating members to form an ultrasound assembly.

In an exemplary embodiment, the ultrasound assembly 42 includes a plurality of ultrasound radiating members 40 that are divided into one or more groups. Each group comprises one or more ultrasound radiating members 40. For example, FIG. 5 is a schematic wiring diagram illustrating one technique for connecting five groups of ultrasound radiating members 40 to form the ultrasound assembly 42. As illustrated in FIG. 5, the ultrasound assembly 42 comprises five groups G1, G2, G3, G4, and G5 of ultrasound radiating members 40 that are electrically connected to each other. The five groups are also electrically connected to the control system 100.

Still referring to FIG. 5, in an exemplary embodiment, the control circuitry 100 includes a voltage source 102 having a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups GIGS is connected to the positive terminal 104 via one of the lead wires 110, and to the negative terminal 106 via the common wire 108.

Although FIG. 5 is illustrated with five groups, the ultrasound assembly 42 can comprise fewer or more groups. For example, in some embodiments the ultrasound assembly 42 can comprise about one to about nine groups. In some embodiments, each group comprises an individually addressable ultrasound radiating member 40. In some embodiments, each ultrasound radiating member 40 is spaced about 0.25 centimeters to about 2 centimeters apart. In some embodiments, each ultrasound radiating member 40 is spaced about one centimeter apart. In some embodiments, the ultrasound radiating members 40 can be located between the fluid delivery and fluid evacuation ports 58. This type of arrangement helps drive the lytic drug that exits the fluid delivery port into the blood clot instead of having the drug flow along the catheter body and into the fluid evacuation port before acting on the blood clot.

Figure 6:
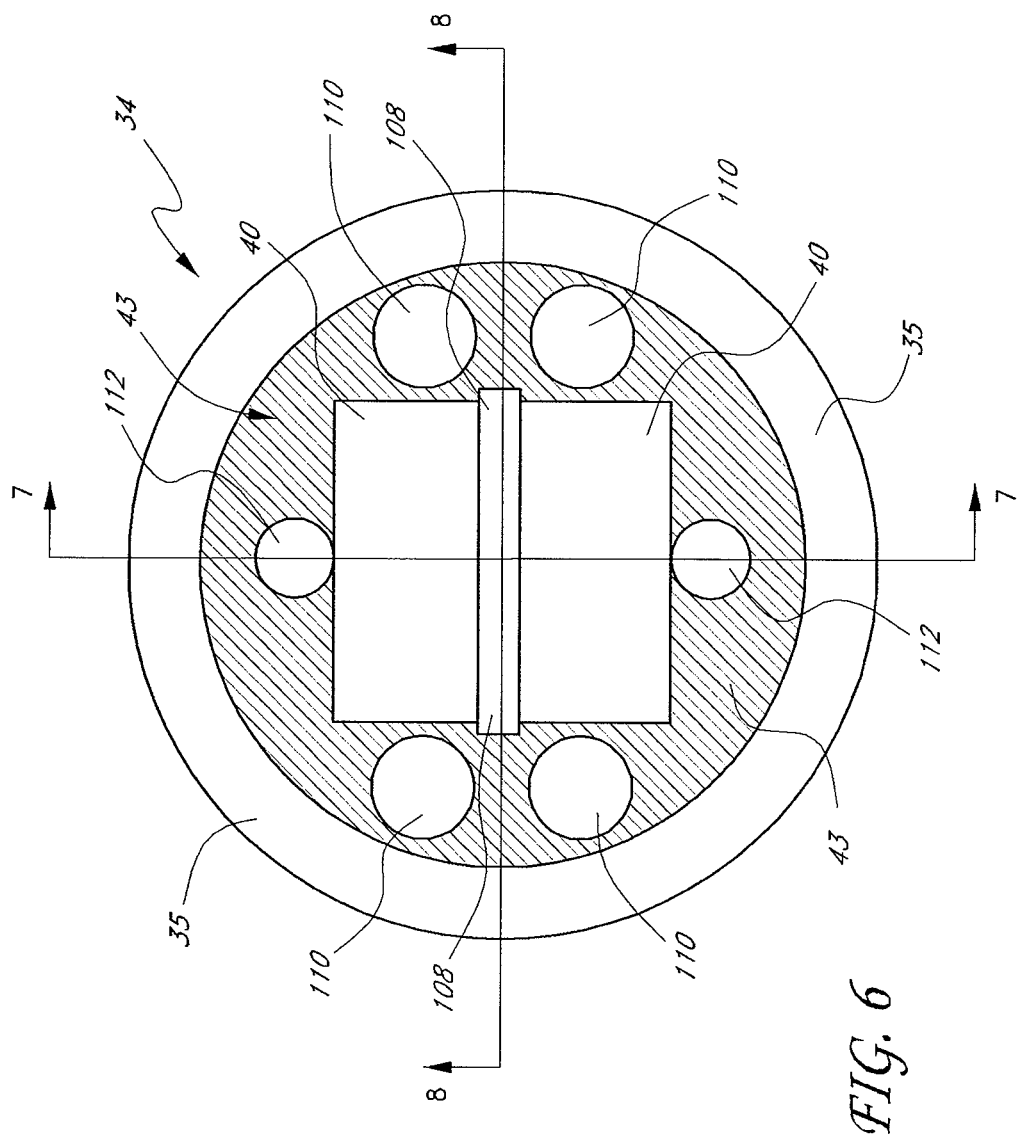
FIG. 6 is a schematic illustration of the ultrasound assembly of FIG. 5 housed within the inner core of FIG. 4.

FIG. 6 illustrates an exemplary technique for arranging the components of the ultrasound assembly 42 (as schematically illustrated in FIG. 5) into the inner core 34 (as schematically illustrated in FIG. 4). FIG. 6 is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

In the exemplary embodiment illustrated in FIG. 6, the common wire 108 includes an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. In such embodiments, lead wires 110 are separated from the other components of the ultrasound assembly 42, thus preventing interference with the operation of the ultrasound radiating members 40 as described above. For example, in an exemplary embodiment, the inner core 34 is filled with an insulating potting material 43, thus deterring unwanted electrical contact between the various components of the ultrasound assembly 42.

Figure 7:
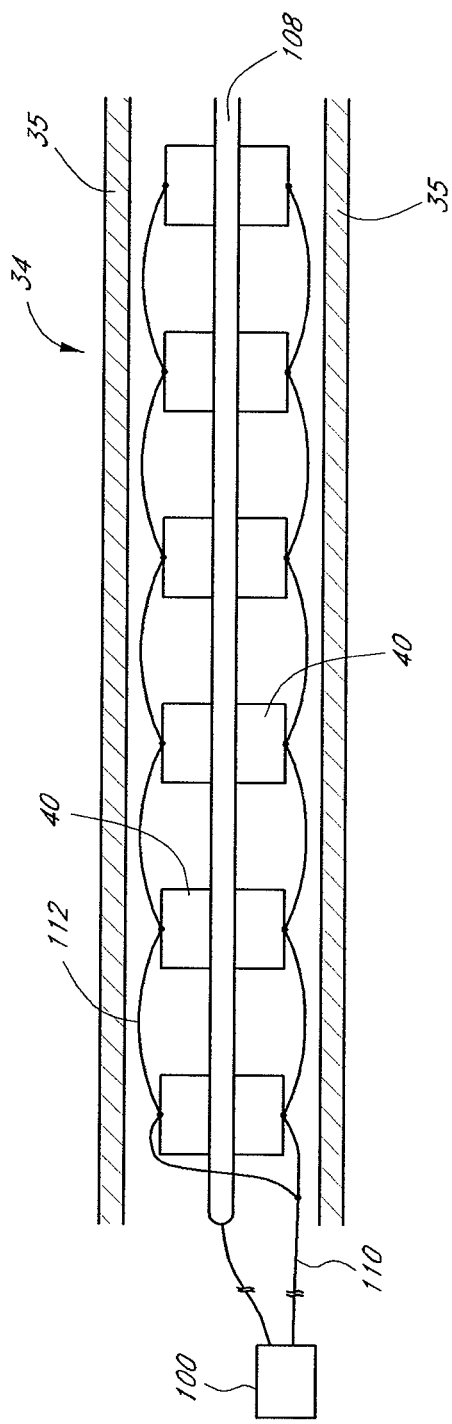
FIG. 7 is a cross-sectional view of the ultrasound assembly of FIG. 6 taken along line 7-7.
Figure 8:
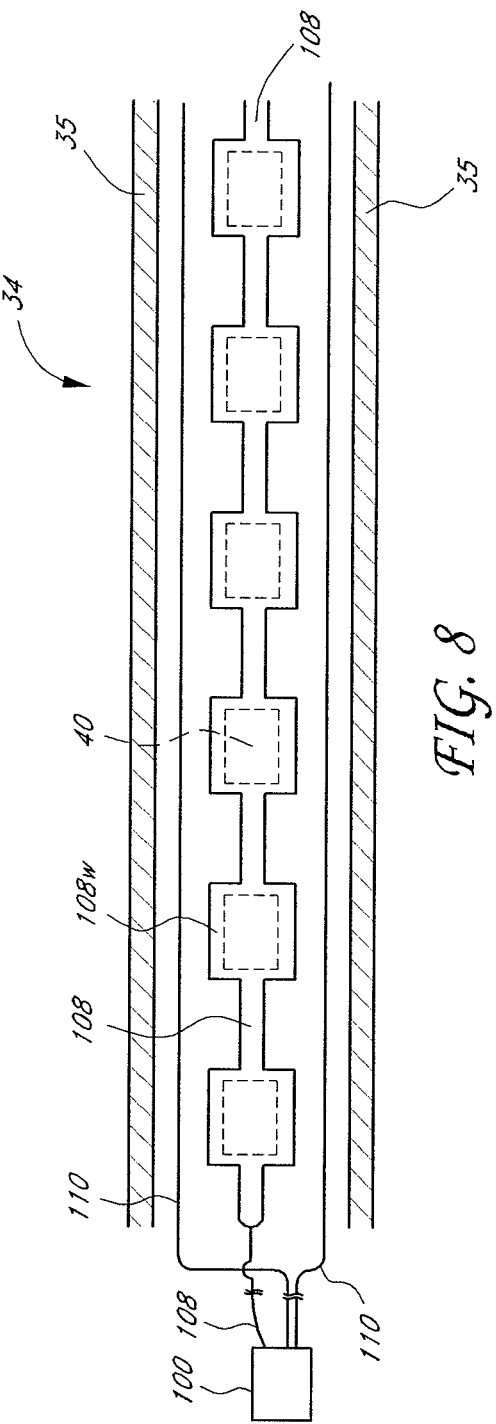
FIG. 8 is a cross-sectional view of the ultrasound assembly of FIG. 6 taken along line 8-8.

FIGS. 7 and 8 illustrate cross sectional views of the inner core 34 of FIG. 6 taken along lines 7-7 and 8-8, respectively. As illustrated in FIG. 7, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 8, the common wire 108 includes wide regions 108W upon which the ultrasound radiating members 40 can be mounted, thus reducing the likelihood that the paired ultrasound radiating members 40 will short together. In certain embodiments, outside the wide regions 108W, the common wire 108 can have a more conventional, rounded wire shape.

The embodiments described above, and illustrated in FIGS. 5 through 8, include a plurality of ultrasound radiating members grouped spatially. That is, in such embodiments, the ultrasound radiating members within a certain group are positioned adjacent to each other, such that when a single group is activated, ultrasonic energy is delivered from a certain length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the ultrasound assembly. Such modified embodiments can be advantageous in applications where a less focused, more diffuse ultrasonic energy field is to be delivered to the treatment site.

In an exemplary embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations and dimensions can be used. For example, disc-shaped ultrasound radiating members 40 or cylindrical-shaped ultrasound radiating members 40 can be used in other embodiments. In some embodiments, the disc-shaped or cylindrical-shaped ultrasound radiating members 40 can have a hole or bore along the central axis of the ultrasound radiating member 40 so that the disc-shaped ultrasound radiating member 40 looks like a washer and the cylindrical ultrasound radiating member 40 looks toroidal. In an exemplary embodiment, the common wire 108 comprises copper, and is about 0.005 inches thick, although other electrically conductive materials and other dimensions can be used in other embodiments. In an exemplary embodiment, lead wires 110 are 36 gauge electrical conductors, and positive contact wires 112 are 42 gauge electrical conductors. However, other wire gauges can be used in other embodiments.

As described above, suitable frequencies for the ultrasound radiating members 40 include, but are not limited to, from about 20 kHz to about 20 MHz. In one embodiment, the frequency is between about 500 kHz and about 20 MHz, and in another embodiment the frequency is between about 1 MHz and about 3 MHz. In yet another embodiment, the ultrasound radiating members 40 are operated with a frequency of about 2 MHz.

Figure 9A:
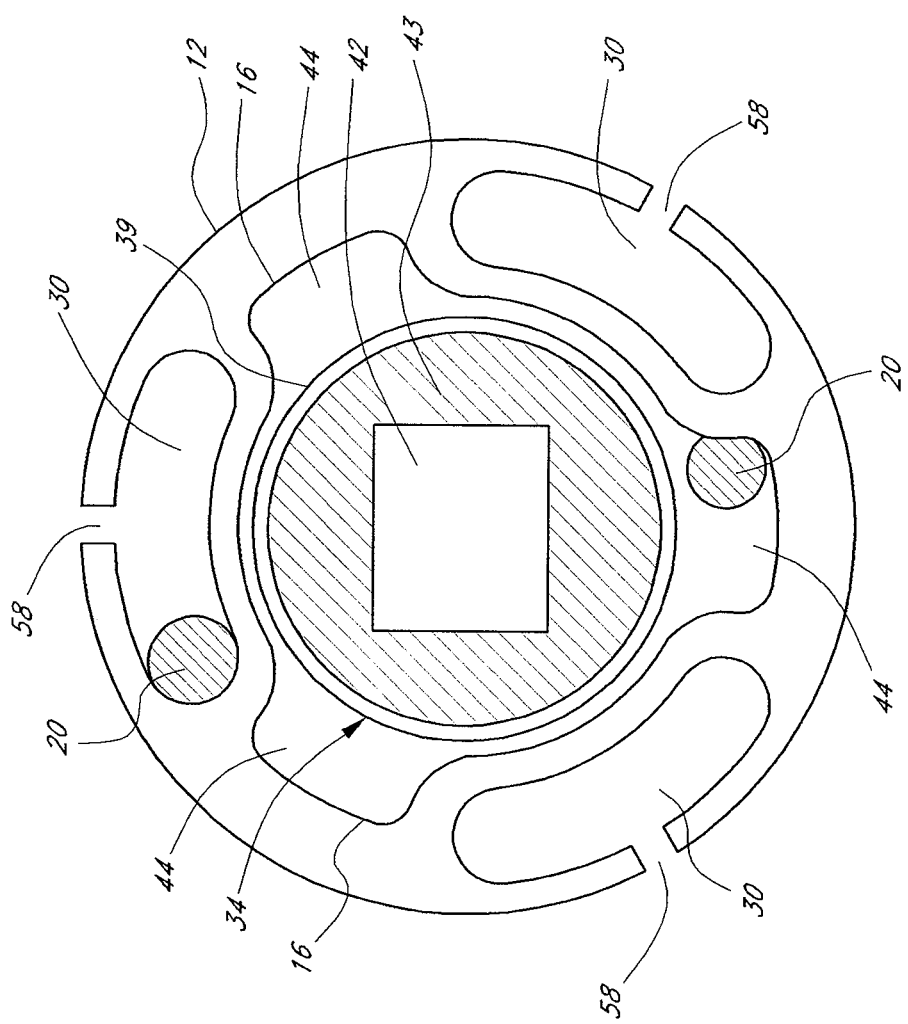
FIG. 9A illustrates the energy delivery section of the inner core of FIG. 4 positioned within the energy delivery section of the tubular body of FIG. 2A.

FIG. 9A illustrates the inner core 34 positioned within an embodiment of the tubular body 12. Details of the ultrasound assembly 42, provided in FIG. 6, are omitted for clarity. As described above, the inner core 34 can be slid within the central lumen 51 of the tubular body 12, thereby allowing the inner core energy delivery section 41 to be positioned within the tubular body energy delivery section 18. For example, in an exemplary embodiment, the materials comprising the inner core energy delivery section 41, the tubular body energy delivery section 18, and the potting material 43 all comprise materials having similar acoustic impedance, thereby minimizing ultrasonic energy losses across material interfaces.

FIG. 9A further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. A plurality of fluid delivery ports 58 can be positioned axially along the tubular body 12. Thus, a source of therapeutic compound coupled to the inlet port 32 provides a hydraulic pressure which drives the therapeutic compound through the fluid delivery lumens 30 and out the fluid delivery ports 58.

By spacing the fluid delivery lumens 30 around the circumference of the tubular body 12 substantially evenly, as illustrated in FIG. 9A, a substantially uniform flow of therapeutic compound around the circumference of the tubular body 12 can be achieved. Additionally, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters than fluid delivery ports closer to the distal region of the energy delivery section 18, thereby allowing uniform delivery of therapeutic compound in the energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to about 0.0020 inches in the distal region of the energy delivery section 18. The increase in size between adjacent fluid delivery ports 58 depends on a variety of factors, including the material comprising the tubular body 12, and on the size of the fluid delivery lumen 30. The fluid delivery ports 58 can be created in the tubular body 12 by punching, drilling, burning or ablating (such as with a laser), or by other suitable methods. Therapeutic compound flow along the length of the tubular body 12 can also be increased by increasing the density of the fluid delivery ports 58 toward the distal region of the energy delivery section.

In certain applications, a spatially nonuniform flow of therapeutic compound from the fluid delivery ports 58 to the treatment site is to be provided. In such applications, the size, location and geometry of the fluid delivery ports 58 can be selected to provide such nonuniform fluid flow.

In another embodiment, one or more of the fluid delivery lumens 30 can be used to evacuate fluid and material from the treatment site. In such an embodiment, a lumen 30 can be connected to a vacuum source (e.g., a pump).

Referring still to FIG. 9A, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flows through cooling fluid lumens 44 and out of the catheter 10 through distal exit port 29 (see FIG. 1). In other embodiments, the cooling fluid does not flow out of the catheter 10 and is instead recirculated within the catheter 10. In an exemplary embodiment, the cooling fluid lumens 44 are substantially evenly spaced around the circumference of the tubular body 12 (that is, at approximately 120 degree increments for a three-lumen configuration), thereby providing substantially uniform cooling fluid flow over the inner core 34. Such a configuration advantageously removes thermal energy from the treatment site. As will be explained below, the flow rate of the cooling fluid and the power to the ultrasound assembly 42 can be adjusted to maintain the temperature of the inner core energy delivery section 41, or of the treatment site generally, within a desired range. In another embodiment, a cooling rod made of a thermally conductive material, such as a metal like copper for example, can be used to cool the catheter by acting as a heat sink. The cooling rod can be a thick copper wire that is incorporated into the inner core 34 as part of the wiring for the circuitry. Alternatively, the cooling rod can be sized, shaped and cofigured to be inserted into a lumen in the catheter, for example the guidewire or stylet lumen or cooling lumens. The cooling rod can be used instead of or in conjunction with liquid cooling.

In another embodiment, the cooling fluid lumen 44 can be used to evacuate the treatment site. In such an embodiment, the cooling fluid lumen 44 can be connected to a vacuum source (e.g., a pump). In this manner, clot material from the treatment site can be removed to reduce pressure at the treatment site. In addition, removal of some elements of the clot material that can cause tissue damage or reduce the rate of healing, such as iron and hemoglobin for example, can help reduce further tissue damage to the brain and promote healing. Fluid can be simultaneously delivered to the clot, with for example lytics and the delivery of ultrasound energy as described herein, from a fluid delivery lumen while fluid is being removed from a fluid removal lumen in a lavage treatment. A single pump configured to provide two actions, fluid delivery and fluid removal, can be used to perform the lavage. Alternatively, two separate pumps can be used, one pump for fluid delivery and another pump for fluid removal.

In an exemplary embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, in an exemplary embodiment, the inner core outer body 35 comprises a material having the ability to transmit torque. Suitable materials for the inner core outer body 35 include, but are not limited to, polyimides, polyesters, polyurethanes, thermoplastic elastomers and braided polyimides. In other embodiments, as mentioned above, the inner core 34 can be coupled to the tubular body 12 or integrally formed with the tubular body 12 to form one part.

In an exemplary embodiment, the fluid delivery lumens 30 and the cooling fluid lumens 44 are open at the distal end of the tubular body 12, thereby allowing the therapeutic compound and the cooling fluid to pass into the patient's vasculature at the distal exit port 29. In a modified embodiment, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can be prevented from passing through the distal exit port 29 by providing the inner core 34 with a length that is less than the length of the tubular body 12. In other embodiments, a protrusion is formed within the tubular body 12 in the distal region 15, thereby preventing the inner core 34 from passing through the distal exit port 29.

In other embodiments, the catheter 10 includes an occlusion device positioned at the distal exit port 29. In such embodiments, the occlusion device has a reduced inner diameter that can accommodate a guidewire, but that is less than the inner diameter of the central lumen 51. Thus, the inner core 34 is prevented from extending past the occlusion device and out the distal exit port 29. For example, suitable inner diameters for the occlusion device include, but are not limited to, between about 0.005 inches and about 0.050 inches. In other embodiments, the occlusion device has a closed end, thus preventing cooling fluid from leaving the catheter 10, and instead recirculating to the tubular body proximal region 14. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In an exemplary embodiment, such as illustrated in FIG. 9A, the tubular body 12 includes one or more temperature sensors 20 that are positioned within the energy delivery section 18. In such embodiments, the tubular body proximal region 14 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

FIG. 9B illustrates the inner core 34 positioned within the embodiment of the tubular body 12 illustrated in FIG. 2B. This embodiment is similar to and incorporates many of the features of the embodiment described above with respect to FIG. 9A. As illustrated in FIG. 9B, the tubular body 12 has six radially disposed lumens 30a-f with corresponding ports 58a-f for fluid delivery and/or fluid evacuation. Lumens used for fluid evacuation can have multiple fluid evacuation ports to reduce the likelihood that all ports of a particular lumen will be blocked or occluded simultaneously. In some embodiments, each lumen used for fluid evacuations has three (3) or more fluid evacuation ports, while in other embodiments, each lumen has less than three (3) fluid evacuation ports. As mentioned above, in modified embodiments, the number and or orientation of the fluid delivery or evacuations and the associated ports can be modified and/or changed. The inner core 34 is disposed within the central lumen 51, resulting in the formation of three interconnected cooling fluid lumens 44 that surround the outer surface 39 of the inner core 44. The cooling fluid can be used to prevent the catheter from overheating and/or to provide localized hypothermia to portions of the brain. Alternatively, thermo-electric cooling may be used instead of cooling fluid to prevent overheating or provide localized hypothermia. In some embodiments, the cooling fluid is retained within the catheter 10. Retaining cooling fluid within the catheter 10 can be particularly advantageous in applications involving the treatment of intracerebral hemorrhages, where it is often desirable to reduce intracranial pressure.

The inner core 34 is similar to the inner core 34 described above in connection with FIGS. 3 and 4. Briefly, the inner core 34 includes a cylindrical outer body 35 that houses the ultrasound assembly 42. In an exemplary embodiment, an electrically insulating potting material 43 fills the inner core 34 and surrounds the ultrasound assembly 42.

In some embodiments as illustrated in FIG. 9B, at least one light source 200 can be positioned the tubular body 12. The light source 200 can be, for example, a light emitting diode (LED) or fiber optic based source connected to an external light source. In some embodiments, LEDs may be mounted on the catheter 1 in the treatment zone. For a fiber optic based source, the external light source can be a filtered broad band light source, or alternatively, a laser. The wavelength and amplitude of light is selected for its ability to penetrate clot and brain tissue while enhancing performance and survival of mitochondria exposed to free hemoglobin and iron. Light can be delivered in a pulsed, chopped, or continuous manner or a combination of the above, to balance any heat generation with mitochondria stimulation and/or protection.

As illustrated in FIG. 9B and discussed above in the embodiment illustrated in FIG. 9A, a temperature sensor 20 located in the energy delivery section of the catheter 10 can be used to monitor and regulate the temperature of the device.

In some embodiments, a pressure sensor 202 is located in one or more of the radially disposed lumens 30*a-f* and near a port 58*a-f*. For example, in some embodiments one pressure sensor 202 can be located in a fluid delivery lumen 30*a* near a fluid delivery port 58*a*, and a second pressure sensor 202 can be located in a fluid evacuation lumen 30*f* near a fluid evacuation port 58*f*. By calculating the pressure drop across a port, the pressure outside the device, i.e. the intracranial pressure around the catheter, can be determined. In other embodiments, the pressure sensor 202 is exposed to the fluid surrounding the outside of the catheter 10 and can directly measure intracranial pressure around the catheter 10. In some embodiments, the pressure sensor 202 can be located at the distal tip of the catheter 10 or in the distal region 15 of the catheter 10. In some embodiments, the pressure sensor 202 can be based on strain gauge technology, fiber optic technology or a semiconductor piezoresistive technology, for example. In some embodiments, the ultrasound radiating member 40 can also be a pressure sensor 202 or can incorporate a pressure sensor 202. In some embodiments, the pressure sensor 202 is in fluid communication with intracranial fluids via a lumen. A measurement of a drop in intracranial pressure can indicate that the treatment is working to reduce the size of the blood clot, thereby reducing the pressure exerted by the blood clot on brain tissue.

Measuring the pressure within the lumens 30*a-f* and around the catheter 10 can be useful for a variety of reasons. For example, it is generally desirable to provide low negative pressure to the evacuation lumens in order to reduce the risk of sucking solid material, such as brain matter, into the evacuation lumen. Furthermore, because reduction of intracranial pressure is often desirable in treating ICH, it is often desirable to deliver fluids with little pressure differential between the delivery pressure and the intracranial pressure around the catheter. In addition, monitoring the pressure can allow the detection of clogged or obstructed ports which would inhibit fluid delivery and/or fluid evacuation. This pressure data can be used as part of a feedback control system for the fluid delivery and evacuation system.

Figure 10:
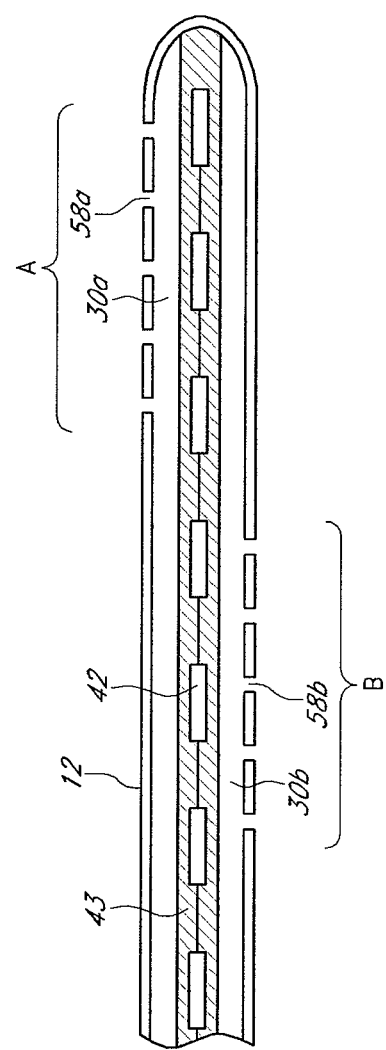
FIG. 10 is a cross-sectional view of the distal end of an ultrasonic catheter having fluid delivery lumens associated with fluid delivery ports along specific axial lengths of the ultrasonic catheter.

FIG. 10 illustrates an embodiment in which the treatment region is divided into treatment sub-regions. In the illustrated exemplary embodiment, the tubular body 12 is subdivided into two sub-regions A and B. Although the sub-regions are illustrated as being approximately the same length in FIG. 10, they need not have the same length in other embodiments. Furthermore, more than or fewer than three treatment sub-regions can be used in other embodiments.

In one embodiment as illustrated in FIG. 10, the catheter is configured such that fluid delivery is controllable between the sub-regions. Fluid control between the sub-regions is accomplished by using the fluid delivery lumens 30*a*, 30*b* incorporated into the interior of the tubular body. In such embodiments, fluid delivery lumen 30*a* has fluid delivery ports 58*a* in region A of the tubular body and fluid delivery lumen B has fluid delivery ports 58*b* in region B of the tubular body. By passing a therapeutic compound along a selected fluid delivery lumen A or B, this configuration allows a therapeutic compound to be delivered along selected axial regions of the tubular body 12.

In a modified embodiment, different therapeutic compounds are passed through different fluid delivery lumens. For example, in one embodiment a first therapeutic compound is delivered to one or more end portions of a blood clot, such as a proximal end and a distal end of the vascular blockage. Similarly, a second therapeutic compound is delivered to an internal portion of the blood clot. Such a configuration is particularly useful where it is determined that the first therapeutic compound is more effective at treating an end portion of the blood clot, and the second therapeutic compound is more effective at treating an internal portion of the blood clot. In another embodiment, the second (or first) therapeutic compound may activate or react with the first (or second) therapeutic compound to create the desired therapeutic effect. In another embodiment, one therapeutic compound can be delivered to provide neuroprotective effects. For example, the neuroprotective compound can be delivered to brain tissue surrounding the clot. Similarly, drugs that counteract cytotoxic compounds in the blood clot can be delivered to the blood clot and/or brain tissue surrounding the clot. In some embodiments, a blood clotting drug can be delivered if bleeding in the brain is detected.

In another modified embodiment, the catheter is configured with more than or fewer than two treatment sub-regions. In such embodiments, the catheter optionally includes more than or fewer than two fluid delivery lumens with the fluid delivery ports of each lumen being associated with a specific sub-region. For example, in one such embodiment, a catheter includes three fluid delivery lumens, each configured to deliver a therapeutic compound to one of three treatment regions.

In yet another modified embodiment, one or more of the fluid delivery lumens is configured to have fluid delivery ports in more than one treatment sub-region. For example, in one such embodiment, a catheter with three delivery lumens and four treatment regions includes a delivery lumen that is configured to deliver therapeutic compound to more than one treatment region.

In yet another modified embodiment, the number of sub-regions along the tubular body is greater than or less than the number of fluid delivery lumens incorporated into the tubular body. For example, in one such embodiment, a catheter has two treatment regions and three delivery lumens. This configuration provides one dedicated delivery lumen for each of the treatment regions, as well as providing a delivery lumen capable of delivering a therapeutic compound to both treatment regions simultaneously.

In the embodiments disclosed herein, the delivery lumens optionally extend to the distal end of the catheter. For example, in one embodiment, a delivery lumen that is configured to deliver a therapeutic compound to a proximal end of the blood clot does not extend to the distal end of the catheter.

In one embodiment, a tubular body has a treatment region of length 3n cm that is divided into three regions, each of length n cm. The tubular body has three fluid delivery lumens incorporated therein. A first fluid delivery lumen contains fluid delivery ports along the first region for a total of n cm of fluid delivery ports. A second fluid delivery lumen contains fluid delivery ports along the first and second regions for a total of 2n cm of fluid delivery ports. A third fluid delivery lumen contains fluid delivery ports along all 3n cm of the tubular body treatment region. Therapeutic compound can be delivered through one, two, or all three of the fluid delivery lumens depending on the length of the blood clot to be treated. In one such embodiment, n=1. In other embodiments n has a value between about zero and about two.

The dimensions of the treatment regions and the fluid delivery lumens provided herein are approximate. Other lengths for fluid delivery lumens and treatment regions can be used in other embodiments.

The ultrasound assembly has a length that may be shorter than, longer than, or equal to a length of one the treatment regions A and B in the tubular body 12. For example, in one embodiment the length of the ultrasound assembly is an integral multiple of length of an ultrasound radiating member group, as illustrated in FIG. 5. In one embodiment, the length of an ultrasound radiating member group is approximately 3 cm, and the length of a treatment region A and B in the tubular body is also about 3 cm. In another embodiment, the length of the tubular body treatment regions is an integral multiple of the length of an ultrasound radiating member group. For example, in one such embodiment the ultrasound radiating member groups are 1 cm long, and the tubular body treatment regions A and B are 2 cm long. In such embodiments, there is optionally more than one ultrasound radiating member group associated with each tubular body treatment region A and B.

An ultrasonic catheter with fluid delivery sub-regions is particularly advantageous in embodiments wherein the blood clot to be treated is elongated. For example, in one application, a therapeutic compound is delivered to a selected sub-region of the blood clot. Thus, if treatment progresses faster in a particular sub-region of the blood clot, the therapeutic compound and ultrasonic energy delivered to that region of the occlusion can be selectively reduced or terminated, and the treatment can move to other regions of the blood clot.

An ultrasonic catheter with fluid delivery sub-regions can be used to treat blood clots having a wide variety of different lengths. For example, to treat a relatively short blood clot, a distal portion of the tubular body is delivered to the treatment site, and therapeutic compound is passed through a fluid delivery lumen having fluid delivery sub-regions in the distal portion of the tubular body. This same catheter can also be used to treat a relatively long blood clot by using more of the flow regions. In this manner, a single tubular body can be used to treat different lengths of blood clots, thereby reducing inventory costs.

Additionally, in some embodiments the ultrasound radiating member groups of the ultrasonic assembly are configured to correspond to the fluid delivery sub-regions. In this manner, ultrasonic energy is selectively applied to the sub-regions that are positioned in or adjacent to the blood clot. Furthermore, such an arrangement ensures that drugs delivered via the fluid delivery ports will be within the effect of the ultrasonic field generated by the ultrasonic assembly. Thus, in such embodiments, a single ultrasonic assembly and a single drug delivery catheter are used to treat blood clots of different lengths.

In one embodiment, the number and lengths of the treatment regions A and B is chosen based upon the observed or calculated distribution of blood clot lengths in the patient population. That is, number and lengths of the sub-region are chosen to correspond to common blood clot lengths in many patients. In a similar manner, the number and lengths of the ultrasound radiating members is also optionally configured to correspond to common blood clot lengths.

In some of the embodiments described above, by controlling flow into the treatment sub-regions, non-uniform flow is delivered to the treatment site in the patient's vasculature. In some embodiments, the amount of flow delivered to each treatment sub-region is configured so as to produce improved treatment results for a given occlusion length. Additionally, the flow within each treatment sub-region is optionally manipulated by configuring the size, location and/or geometry of the fluid delivery ports to achieve uniform or non-uniform flow delivery within the treatment sub-region. Such techniques are optionally combined with selective electronic control of the ultrasound radiating member groups within treatment sub-regions. For example, the ultrasound radiating members can be repeatedly activated in a sequential order in an axial direction to create an acoustic peristaltic pump effect that drives fluid delivered from the fluid delivery ports in both a radial and axial direction.

Figure 11:
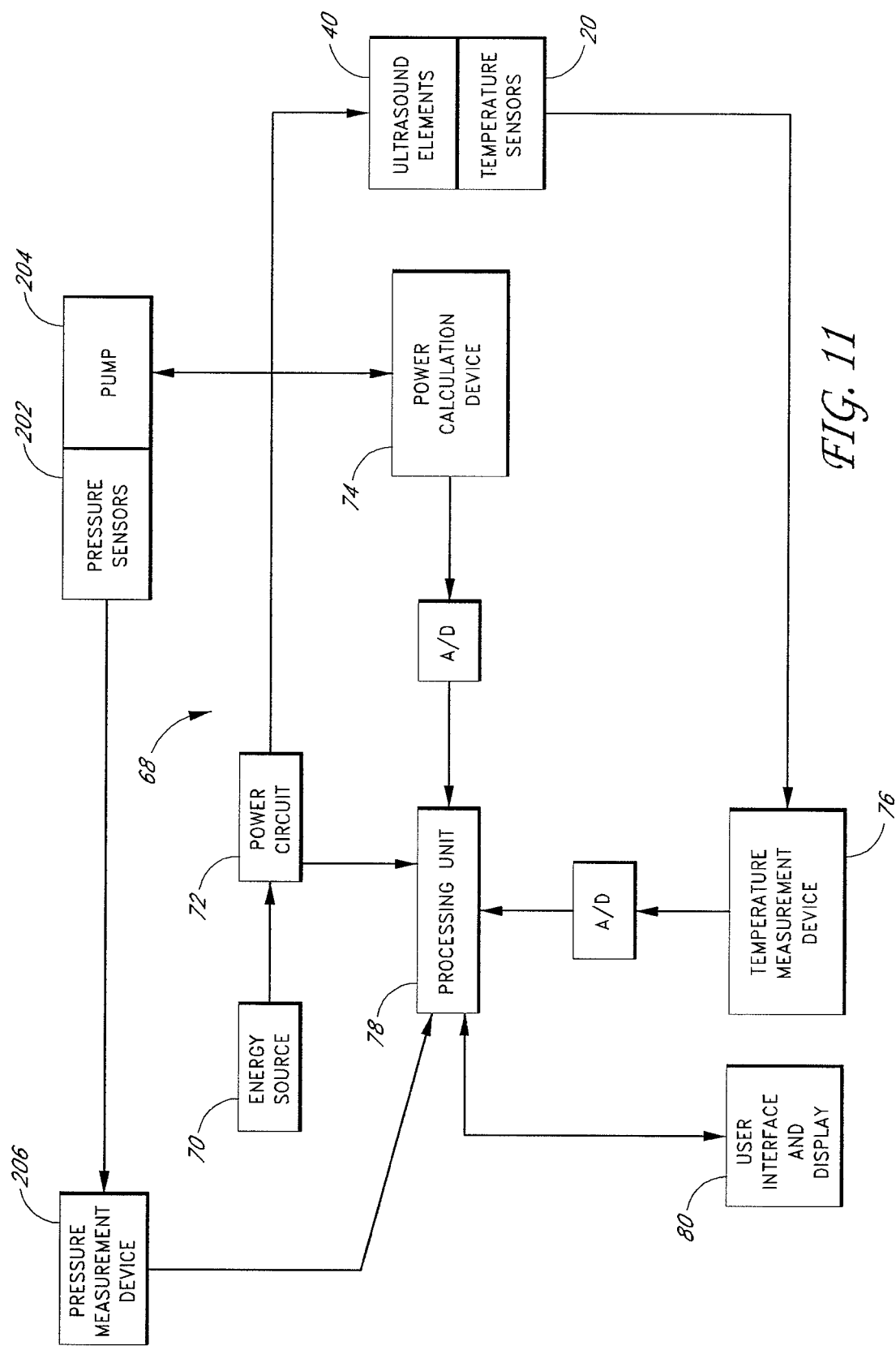
FIG. 11 is a block diagram of a feedback control system for use with an ultrasonic catheter.

FIG. 11 schematically illustrates one embodiment of a feedback control system 68 that can be used with the catheter 10. The feedback control system 68 can be integrated into the control system 100 that is connected to the inner core 34 via cable 45 (as illustrated in FIG. 1). The feedback control system 68 allows the temperature at each temperature sensor 20 to be monitored and allows the output power of the energy source 70 to be adjusted accordingly. In some embodiments, each ultrasound radiating member 40 is associated with a temperature sensor 20 that monitors the temperature of the ultrasound radiating member 40 and allows the feedback control system 68 to control the power delivered to each ultrasound radiating member 40. In some embodiments, the ultrasound radiating member 40 itself is also a temperature sensor 20 and can provide temperature feedback to the feedback control system 68. In addition, the feedback control system 68 allows the pressure at each pressure sensor 202 to be monitored and allows the output power of the energy source 70 to be adjusted accordingly. A physician can, if desired, override the closed or open loop system.

In an exemplary embodiment, the feedback control system 68 includes an energy source 70, power circuits 72 and a power calculation device 74 that is coupled to the ultrasound radiating members 40 and a pump 204. A temperature measurement device 76 is coupled to the temperature sensors 20 in the tubular body 12. A pressure measurement device 206 is coupled to the pressure sensors 202. A processing unit 78 is coupled to the power calculation device 74, the power circuits 72 and a user interface and display 80.

In an exemplary method of operation, the temperature at each temperature sensor 20 is determined by the temperature measurement device 76. The processing unit 78 receives each determined temperature from the temperature measurement device 76. The determined temperature can then be displayed to the user at the user interface and display 80.

In an exemplary embodiment, the processing unit 78 includes logic for generating a temperature control signal. The temperature control signal is proportional to the difference between the measured temperature and a desired temperature. The desired temperature can be determined by the user (as set at the user interface and display 80) or can be preset within the processing unit 78.

In such embodiments, the temperature control signal is received by the power circuits 72. The power circuits 72 are configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is reduced in response to that temperature control signal. Similarly, when the temperature control signal is below a particular level, the power supplied to a particular group of ultrasound radiating members 40 is increased in response to that temperature control signal. After each power adjustment, the processing unit 78 monitors the temperature sensors 20 and produces another temperature control signal which is received by the power circuits 72.

In an exemplary method of operation, the pressure at each pressure sensor 202 is determined by the pressure measurement device 206. The processing unit 78 receives each determined pressure from the pressure measurement device 206. The determined pressure can then be displayed to the user at the user interface and display 80.

In an exemplary embodiment, the processing unit 78 includes logic for generating a pressure control signal. The pressure control signal is proportional to the difference between the measured pressure and a desired pressure. The desired pressure can be determined by the user (as set at the user interface and display 80) or can be preset within the processing unit 78.

As noted above, it is generally desirable to provide low negative pressure to the evacuation lumens in order to reduce the risk of sucking solid material, such as brain matter, into the evacuation lumen. Furthermore, because reduction of intracranial pressure is often desirable in treating ICH, it is often desirable to deliver fluids with little pressure differential between the delivery pressure and the intracranial pressure around the catheter. Accordingly, the processing unit 78 can be configured to monitor the pressure and modify or cease the delivery of fluid and/or increase evacuation of fluid to the treatment site if intracranial pressure increases beyond a specified limit.

In other embodiments, the pressure control signal is received by the power circuits 72. The power circuits 72 are configured to adjust the power level, voltage, phase and/or current of the electrical energy supplied to the pump 204 from the energy source 70. For example, when the pressure control signal is above a particular level, the power supplied to a particular pump 204 is reduced in response to that pressure control signal. Similarly, when the pressure control signal is below a particular level, the power supplied to a particular pump 204 is increased in response to that pressure control signal. After each power adjustment, the processing unit 78 monitors the pressure sensors 202 and produces another pressure control signal which is received by the power circuits 72.

In an exemplary embodiment, the processing unit 78 optionally includes safety control logic. The safety control logic detects when the temperature at a temperature sensor 20 and/or the pressure at a pressure sensor 202 exceeds a safety threshold. In this case, the processing unit 78 can be configured to provide a temperature control signal and/or pressure control signal which causes the power circuits 72 to stop the delivery of energy from the energy source 70 to that particular group of ultrasound radiating members 40 and/or that particular pump 204.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating members 40 can be identically adjusted in certain embodiments. For example, in a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 can also be configured to receive a power signal from the power calculation device 74. The power signal can be used to determine the power being received by each group of ultrasound radiating members 40 and/or pump 204. The determined power can then be displayed to the user on the user interface and display 80.

As described above, the feedback control system 68 can be configured to maintain tissue adjacent to the energy delivery section 18 below a desired temperature. For example, in certain applications, tissue at the treatment site is to have a temperature increase of less than or equal to approximately 6 degrees C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as a computer with software. In embodiments wherein the processing unit 78 is a computer, the computer can include a central processing unit ("CPU") coupled through a system bus. In such embodiments, the user interface and display 80 can include a mouse, a keyboard, a disk drive, a display monitor, a nonvolatile memory system, and/or other computer components. In an exemplary embodiment, program memory and/or data memory is also coupled to the bus.

In another embodiment, in lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 is provided according to the preset profiles.

In an exemplary embodiment, the ultrasound radiating members are operated in a pulsed mode. For example, in one embodiment, the time average power supplied to the ultrasound radiating members is between about 0.1 watts and about 2 watts. In another embodiment, the time average power supplied to the ultrasound radiating members is between about 0.5 watts and about 1.5 watts. In yet another embodiment, the time average power supplied to the ultrasound radiating members is approximately 0.6 watts or approximately 1.2 watts. In an exemplary embodiment, the duty cycle is between about 1% and about 50%. In another embodiment, the duty cycle is between about 5% and about 25%. In yet another embodiment, the duty cycles is approximately 7.5% or approximately 15%. In an exemplary embodiment, the pulse averaged power is between about 0.1 watts and about 20 watts. In another embodiment, the pulse averaged power is between approximately 5 watts and approximately 20 watts. In yet another embodiment, the pulse averaged power is approximately 8 watts or approximately 16 watts. The amplitude during each pulse can be constant or varied.

In an exemplary embodiment, the pulse repetition rate is between about 5 Hz and about 150 Hz. In another embodiment, the pulse repetition rate is between about 10 Hz and about 50 Hz. In yet another embodiment, the pulse repetition rate is approximately 30 Hz. In an exemplary embodiment, the pulse duration is between about 1 millisecond and about 50 milliseconds. In another embodiment, the pulse duration is between about 1 millisecond and about 25 milliseconds. In yet another embodiment, the pulse duration is approximately 2.5 milliseconds or approximately 5 milliseconds.

For example, in one particular embodiment, the ultrasound radiating members are operated at an average power of approximately 0.6 watts, a duty cycle of approximately 7.5%, a pulse repetition rate of approximately 30 Hz, a pulse average electrical power of approximately 8 watts and a pulse duration of approximately 2.5 milliseconds.

In an exemplary embodiment, the ultrasound radiating member used with the electrical parameters described herein has an acoustic efficiency greater than approximately 50%. In another embodiment, the ultrasound radiating member used with the electrical parameters described herein has an acoustic efficiency greater than approximately 75%). As described herein, the ultrasound radiating members can be formed in a variety of shapes, such as, cylindrical (solid or hollow), flat, bar, triangular, and the like. In an exemplary embodiment, the length of the ultrasound radiating member is between about 0.1 cm and about 0.5 cm, and the thickness or diameter of the ultrasound radiating member is between about 0.02 cm and about 0.2 cm.

Figure 12:
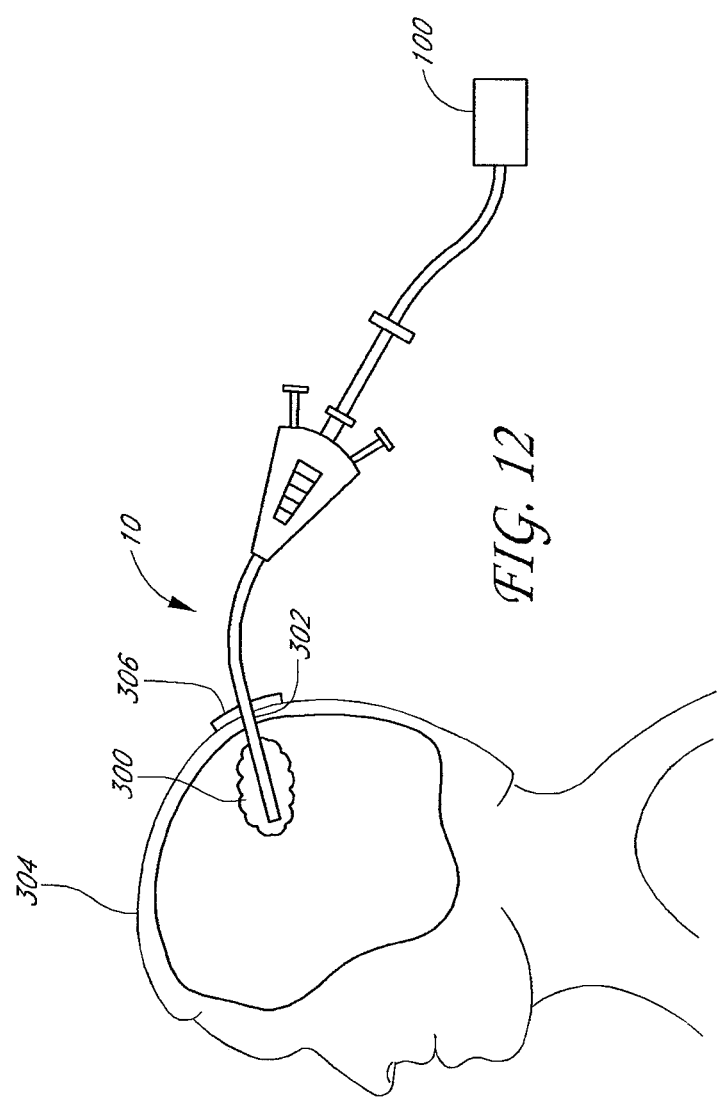
FIG. 12 is a schematic illustration of an ultrasonic catheter inserted into a treatment site through a bore in the patient's skull.
Figure 13:
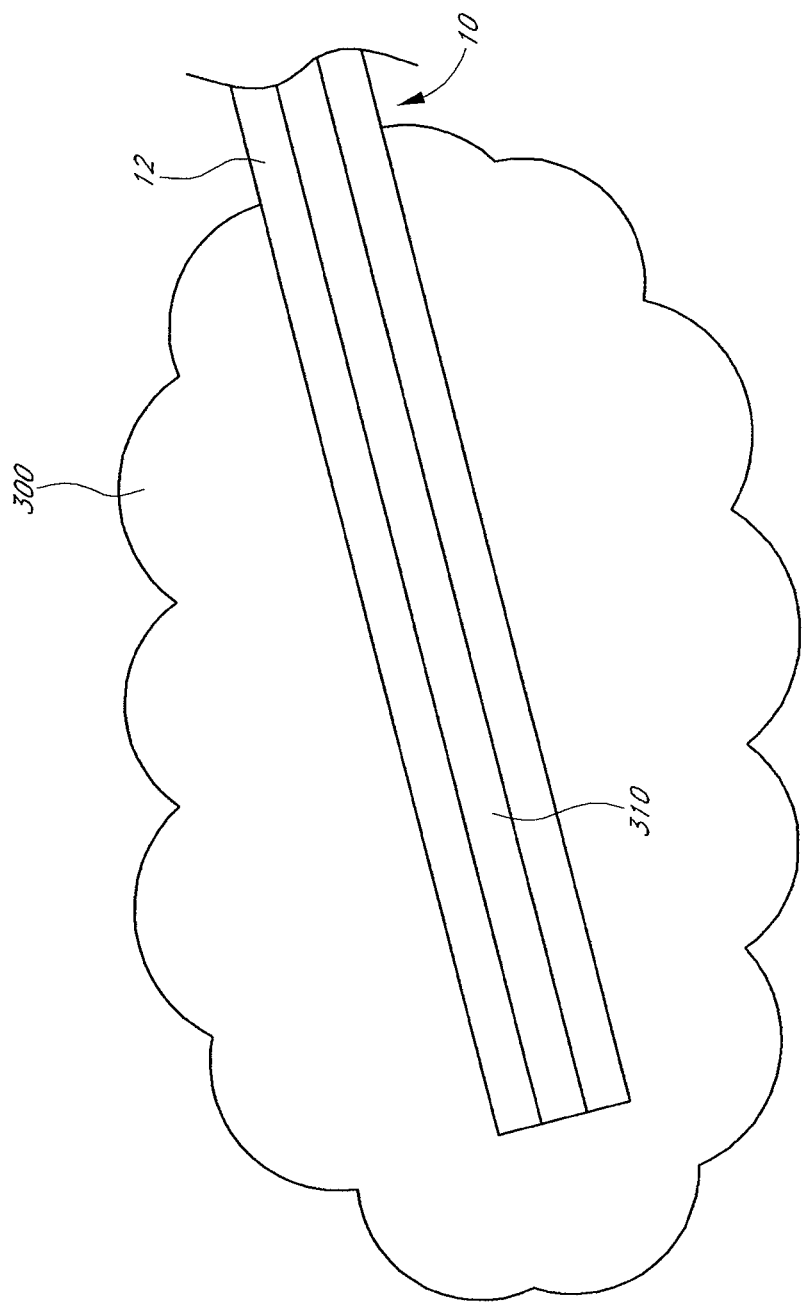
FIG. 13 is a side view of the distal end of an ultrasonic catheter positioned at the treatment site of FIG. 12.

FIG. 12 illustrates an ultrasonic catheter 10 inserted into a blood clot 300 through a bore 302 in the patient's skull 304. Before insertion of the catheter 10, the bore 10 is made by making a very small burr-hole or drill hole in the patient's skull just large enough to permit insertion of the catheter 10. In some embodiments, the burr-hole is larger than a drill hole. In some embodiments, the burr-hole can be located for an occipital approach if the patient has an intraventricular hemorrhage. In some embodiments, the burr-hole can be located for a more frontal approach if the patient has an intracerebral hemorrhage located in the frontal portion of the brain. It should be appreciated that the location of the burr-hole or drill hole can be selected to reduce the path length between the blood clot and the hole in the patient's skull. In addition, it may be desirable in some cases to approach the blood clot from an angle that avoids certain portions of the brain. Next, the dura is dissected by a rigid obturator or by a scalpel. As shown in FIG. 13, the tubular body 12 of the catheter 10 is then mounted over the obturator 310, and the assembly is slid into position within the blood clot 300 with fluoroscopic, magnetic resonance, neuronavigation, and/or computed tomography visualization. The obturator 310 can both plug the end of the catheter 10 and provide the catheter 10 with additional stiffness during insertion into the brain.

After the catheter 10 is in position, a slidable sealing surface 306 on the proximal portion of the catheter 10 can be slid down along the catheter 10 shaft to anchor on the dermis of the patient's head. The slidable sealing surface 306 can have sewing holes and/or an adhesive to form a secure and relatively water-tight seal around the bore and catheter 10. The slidable sealing surface can be formed, for example, from a disk made of two layers. The first layer can have a slit that permits passage of an instrument but is otherwise generally closed. The second layer can be made of an elastic material and have a hole with a diameter slightly less than the diameter of the catheter 10 shaft, so that insertion of the catheter 10 shaft through the hole results in a tight seal.

The obturator 310 can then be removed and replaced with the inner core 34. Drug infusion is then initiated via a constant infusion pump along with a constant evacuation of fluid at a low negative pressure and at a rate equal or approximately equal to the rate of fluid delivery from the drug infusion. As the blood clot 300 is liquefied, it may be desirable in some embodiments to increase the evacuation of fluid to reduce the intracranial pressure. In this situation, the rate of evacuation may be greater than the rate of fluid delivery. Ultrasound is also initiated during drug infusion, so that the thrombolytic drug acts more efficiently on the blood clot 300. Light sources can also be activated after the catheter 10 has been inserted into the blood clot 300.

Examples of thrombolytic drugs include rt-PA and t-PA. In some embodiments, approximately 2,000 IU/mL to 50,000 IU/mL of rt-PA is delivered at a flow rate of approximately 1 mL/hr to 25 mL/hr. In other embodiments, approximately 10,000 IU/mL of rt-PA is delivered at a flow rate of approximately 5 mL/hr.

Because the ICH blood clot 300 is generally displacing brain tissue, as lysis of the blood clot 300 proceeds and liquefied blood clot 300 material is evacuated, the remaining portions of the blood clot 300 will tend to move towards the treatment portion of the catheter. This phenomenon enhances the blood clot 300 lysis process, making it more efficient.

Figure 14:
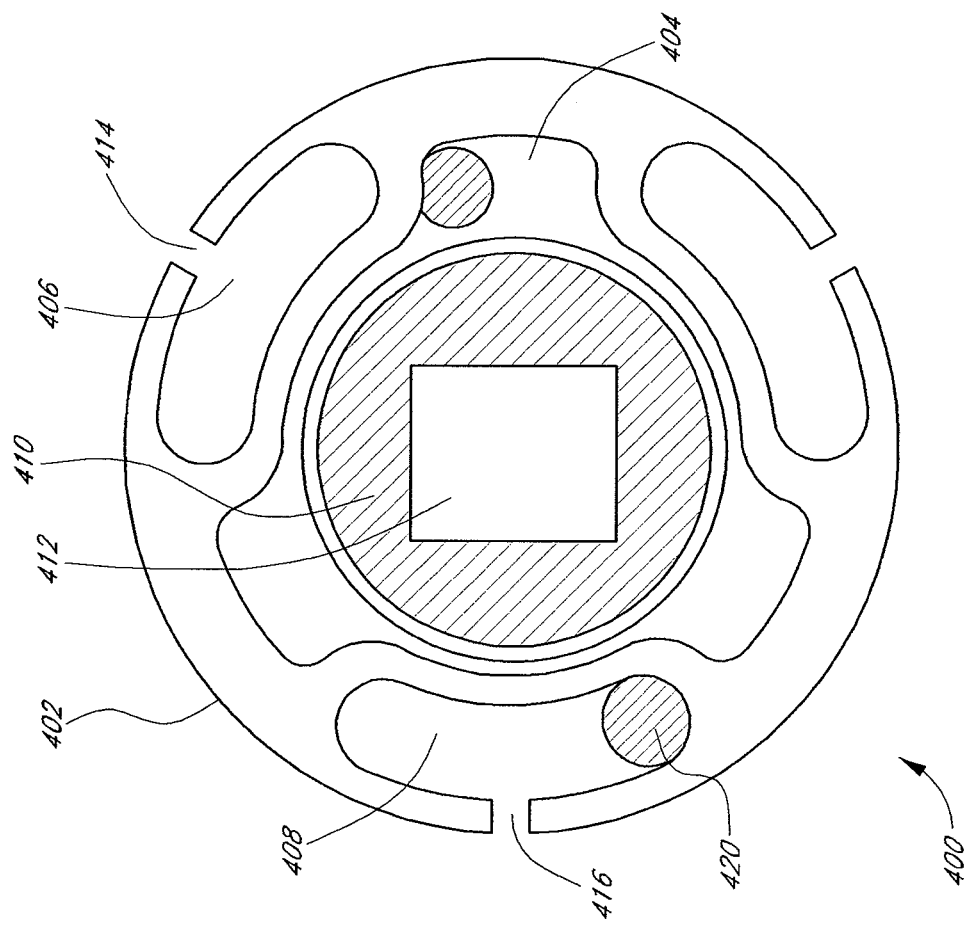
FIG. 14 is a cross-sectional view of the distal end of an ultrasonic catheter having a fluid delivery lumen and a fluid evacuation lumen.

FIG. 14 illustrates one embodiment of an ultrasonic catheter 400 that is suitable for treating an ICH or IVH. The catheter 400 comprises an elongate tubular body 402 with a central lumen 404, a fluid delivery lumen 406 and a fluid evacuation lumen 408, which can be arranged as described above. The central lumen 404 receives an inner core 410 comprising a plurality of ultrasound radiating member 412. A drug, such as a thrombolytic drug, can be delivered from the fluid delivery lumen via fluid delivery ports 414. Fluids surround the catheter 400, such as blood, portions of a dissolved blood clot and/or cerebral spinal fluid can be evacuated into the fluid evacuation lumen 408 via fluid evacuation ports 416. In some embodiments, the fluid evacuation ports 416 are relatively large, and can have a diameter between about 0.005 to about 0.040 inches. In other embodiments, the fluid evacuation ports 416 have a diameter between about 0.01 to about 0.02 inches. In other embodiments, the fluid evacuation ports 416 have a diameter of about 0.01, 0.015 or 0.02 inches. A screen or mesh or filter can be placed over the fluid evacuation ports 416 to reduce the likelihood that brain tissue will be sucked into the fluid evacuation ports 416. In some embodiments, a screen or mesh can be used with an even larger opening for fluid removal. In some embodiments, the catheter 400 can include radiopaque markers in the tubular body 402, and in particular in the distal portion of the tubular body 402, so that the physician can guide the insertion of the catheter 400 to the blood clot using imaging technology, thereby minimizing or reducing brain tissue trauma.

As described above, in some embodiments, the fluid delivery ports 414 are spatially separated from the fluid evacuation ports 416. The fluid delivery ports 414 can be axially and/or radially separated from the fluid evacuation ports 416. In some embodiments, the ultrasound radiating members 412 are located axially between the fluid delivery ports 414 and the fluid evacuation ports 416. Such a configuration would reduce the amount of drug delivered from the fluid delivery ports 414 from being directly evacuated by the fluid evacuation port 416 before the delivered drug can sufficiently act on the blood clot. In other embodiments, the fluid delivery ports 414 are located around the ultrasound radiating members 412 while the fluid evacuation ports 416 are located distally or proximally of the fluid delivery ports 414. Such a configuration allows the ultrasound energy to act upon and/or with the drug delivered from the fluid delivery ports 414 on the blood clot. This configuration tends to push the drug radially away from the catheter 400 and the fluid delivery ports 414.

In some embodiments, it is desirable to maintain or reduce intracranial pressure below a threshold or target pressure while delivering a thrombolytic drug to the blood clot. As described above, in some embodiments, intracranial pressure can be monitored using a pressure sensor 420 located near the fluid evacuation port 416, or alternatively, near the fluid delivery port 414. In some embodiments, intracranial pressure is controlled by delivery of fluid under a positive pressure in the fluid delivery lumen 406 with respect to intracranial pressure, while maintaining a negative pressure in the fluid evacuation lumen 408. The pressures can be adjusted so that fluid is removed at a rate that is equal or greater than the rate fluid is being delivered. If intracranial pressure should be reduced, the negative pressure in the fluid evacuation lumen 408 can be increased so that more fluid is removed, or alternatively, the pressure in the fluid delivery lumen 406 can be reduced so that less fluid is delivered.

In some embodiments, fluid and drug delivery can be accomplished separately and/or intermittently from fluid evacuation to allow the drug an adequate dwell time to act on the clot before evacuation. For example, fluid can be first evacuated from around the blood clot, then drug can be delivered to the blood clot and allowed to act on the blood clot for a predetermined amount of time, and then the cycle of fluid evacuation and drug delivery can be repeated.

Because the blood clot may be under compression by brain tissue surrounding the clot, by continuously or periodically draining fluid from the blood clot, the remaining unlysed portions of the clot tends to be pushed towards the catheter 400, thereby enhancing ultrasound and drug mediated clot lysis. In addition, removal of the lysed portions of the clot removes toxic blood components that can be harmful to brain tissue.

Figure 15:
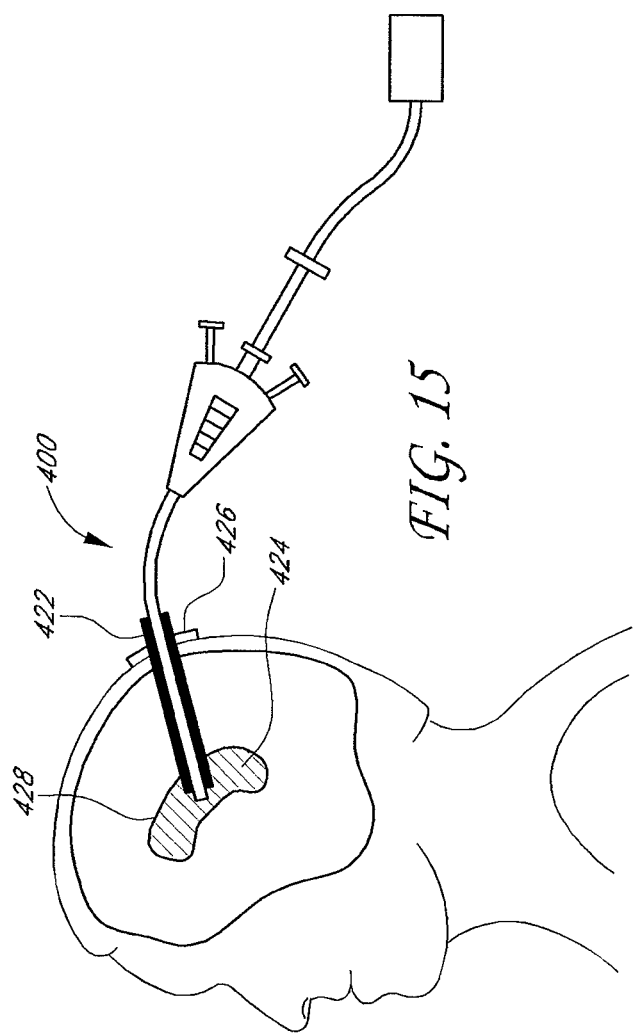
FIG. 15 is schematic illustration of an ultrasonic catheter inserted into a treatment site through an external ventricular drainage catheter.

As illustrated in FIG. 15, in some embodiments, the ultrasound catheter 400 can be used with an external ventricular drain or drainage catheter (EVD) 422 which can be inserted to the blood clot 424 via the burr-hole or drill hole 426 that is formed in the patient's skull as described above. In some embodiments, before the EVD 422 is inserted into the brain, an introducer sheath is inserted through the burr-hole 426 and through brain tissue until it reaches the blood clot 424, which can be located in the ventricles 428 of the brain. In some embodiments, the introducer sheath is about one centimeter to about nine centimeters in length. In other embodiments, the introducer sheath is about five centimeters to about eight centimeters in length. Once the introducer sheath is inserted to the blood clot, the EVD can be inserted into the introducer sheath and guided to the blood clot. In some embodiments, the introducer sheath can then be removed.

The EVD 422 can comprise a lumen for both draining fluid from the blood clot and for receiving the ultrasound catheter 400. The catheter 400 can be inserted into the EVD 422 to the blood clot 424, where the ultrasound catheter 400 can deliver ultrasound energy and/or drugs to enhance clot lysis. In some embodiments, the ultrasound catheter 400 can be inserted alongside the EVD 422. In some embodiments, the EVD 422 can comprise an external groove to accommodate the ultrasound catheter 400. In some embodiments, the ultrasound catheter 400 can be inserted into the blood clot 424 such that the ultrasound radiating members 412 in the catheter 400 extend past the distal tip of the EVD 422 and into the blood clot 424. In other embodiments, the distal portion of the EVD 422 can be made to be ultrasound transparent so that ultrasound energy can be transmitted through the walls of the EVD 422 to the blood clot. In embodiments where the EVD 422 is ultrasound transparent, the ultrasound radiating members 412 of the ultrasound catheter 400 can remain within or alongside the EVD 422.

In some embodiments, ultrasound radiating members 412 can be incorporated into the EVD 422. For example, the ultrasound radiating members 412 can be formed into a cylindrical shape and integrated into the EVD 422 such that the outer surface of the ultrasound radiating members 412 are externally exposed on the EVD 422, thereby enhancing ultrasound radiation from the EVD 422. In other embodiments, ultrasound radiating members 412, such as sandwich type ultrasound radiating members 412, can be incorporated into one lumen of a multi-lumen, ultrasound transparent EVD 422, where the other lumens of the EVD 422 are used for drainage and/or drug delivery. In some embodiments, drugs can be delivered to the blood clot via the ultrasound catheter 400, a separate drug delivery catheter or the EVD 422 itself. Where the catheter 400 is used in conjunction with the EVD 422, the catheter 400 can optionally include the fluid evacuation lumen 408 since fluid can alternatively be evacuated via the EVD 422. In other embodiments, fluid can be evacuated by both the EVD 422 and ultrasound catheter 400.

In some embodiments, an introducer sheath is not used or is optionally used to access the blood clot. In these embodiments, a stylet can be used to provide the ultrasound catheter 400 and/or the EVD 422 with enough column strength to push through the brain tissue and access the blood clot within the brain. For example, the inner core 410 of the ultrasound catheter 400 can be removed and the stylet can be inserted into the central lumen 404 during insertion of the ultrasound catheter 400 into the patient's brain. Similarly, the stylet can be inserted into the lumen of the EVD 422 during insertion of the EVD 422 into the patient's brain. After the ultrasound catheter 400 and/or EVD 422 has been inserted, the stylet can be removed to reduce damage to brain tissue.

In other embodiments, a flexible and/or floppy tip guidewire is used to initially access the blood clot within the patient's brain. The ultrasound catheter 400 and/or EVD 422 can then be introduced over the guidewire and threaded to the blood clot. After the ultrasound catheter 400 and/or EVD 422 has been inserted to the blood clot, the guidewire can be removed. In other embodiments, the guidewire can be left in place with the flexible and/or floppy tip extending beyond the distal end of the ultrasound catheter 400 or EVD 422 so that the flexible and/or floppy tip provides a relatively atraumatic structure to reduce further tissue damage.

In other embodiments, the ultrasound catheter 400 can be delivered to the blood clot in the patient's brain through the vasculature. A portion of a blood vessel large enough to accommodate the ultrasound catheter 400 and near the blood clot can be selected as a delivery zone. The blood vessel can be sealed proximally and distally around the delivery zone using, for example, an adhesive or an occlusion device such as an inflatable balloon. After the vessel has been sealed, the vessel can be perforated and the ultrasound catheter 400 can be passed through the perforation and into the blood clot, where ultrasound energy and drugs can be delivered to the clot while fluid is evacuated. Alternatively, instead of perforating the vessel, the ultrasound catheter 400 can remain within the vessel and radiate ultrasound energy through the vessel wall and to the blood clot. Because the vessel is not perforated, the vessel does not need to be sealed around the delivery zone. Also, in this embodiment, drug can be delivered to the blood clot and fluid can be evacuated from the blood clot by a needle, an EVD 422 or other catheter.

Ultrasound energy can be delivered for a duration sufficient to enable adequate drug distribution in and/or around the blood clot. This can be accomplished by either intermittent or continuous delivery of ultrasound energy. For example, ultrasound energy can be delivered for a set time period to adequately distribute the drug to the blood clot, and then turned off to allow the drug to act on the blood clot. Alternatively, ultrasound energy can be delivered substantially continuously after the drug has been delivered to the blood clot to continuously redistribute the drug into the blood clot as the blood clot is successfully lysed. In addition, ultrasound energy can be delivered intermittently to reduce heating. Also, as described in U.S. application Ser. No. 11/971,172, filed Jan. 8, 2008, which is hereby incorporated by reference herein in its entirety, the power parameters controlling the delivery of ultrasound energy can be randomized or varied according to complex non-linear algorithms in order to enhance the efficacy of the ultrasound treatment.

Drug delivery can be controlled by monitoring, for example, lysis byproducts such as D-dimer in the effluent evacuated from the blood clot. A high and/or increasing concentration of D-dimer in the effluent can indicate that lysis of the blood clot is proceeding adequately, and therefore drug delivery can be maintained, reduced or stopped. A low or decreasing concentration of D-dimer in the effluent can indicate that lysis of the blood clot is inadequate or slowing or that the clot is nearly dissolved, and therefore drug delivery can be increased if the clot is not nearly dissolved, and reduced or stopped if lysis is almost complete. Alternatively, lytic concentration can be monitored to determine whether more drug should be delivered and whether lysis is complete. In some embodiments, as lysis of the blood clot proceeds, lytic is freed from the lysed clot, thereby increasing the concentration of lytic in the effluent. Therefore, increased lytic concentration can correlate to lysis completion. One way of determining the concentration of lytic and/or D-dimer in the effluent is to measure the color of the effluent that is evacuated from the blood clot. The redder the effluent, the greater the concentration of lytic and/or D-dimer in the effluent.

In some embodiments, endoscopic delivery of the ultrasound catheter 400 to the blood clot can be used to correctly place the ultrasound radiating members into the blood clot in the absence of fluoroscopy.

In some embodiments, a laser can be used to ablate or disrupt the clot, and the resulting effluent can be drained away. In this embodiment, the wavelength of the laser is selected so that absorption by neuronal or glial tissues is reduced, thereby reducing tissue damage. In addition, the laser beam should avoid being focused on blood circulating in vessels within the brain and supplying the neuronal or glial tissues with nutrients, since the blood can be heated by the laser and cause tissue damage.

In some embodiments, ultrasound can be transmitted from an ultrasound radiating member located outside the patient to the blood clot within the patient's brain through an elongate ultrasound transmission member, which can be a vibrating wire, for example. The proximal end of the vibrating wire can be attached to or in communication with the ultrasound radiating member while the distal end of the vibrating wire can be configured to deliver ultrasound energy to the blood clot. The vibrating wire can be inserted into the brain and to the clot through a catheter, an EVD or other access device. Drug delivery and fluid evacuation can be accomplished with the catheter, the EVD or the other access device.

In some embodiments, the ultrasound catheter 400 can be used to deliver oncological drugs, especially sonodynamic drugs, to tumors and gliomas in the brain. The methods and apparatus described above can be used to treat tumors and gliomas instead of blood clots.

In some embodiments, the methods and apparatus described above can be used to treat a blood clot in a fistula.

In some embodiments, neuroprotective drugs or agents that assist in the functional recovery and/or the reduction of cell and tissue damage in the brain can also be delivered to the brain and blood clot with the methods and apparatus described above. These neuroprotective drugs or agents can be delivered before, with, or after the delivery of the thrombolytic drugs. Delivery of these drugs using the methods and apparatus described above is particularly useful where the drug delivery through the blood brain barrier is enhanced with ultrasound treatment, or where ultrasound enhances cell penetration by the drug, or where the drug is sonodynamic.

In some embodiments, the ultrasound radiating member is not inserted into the brain. Instead, after the bore hole is made and the dura is optionally removed to expose the brain, an ultrasound radiating member can be placed within the bore hole and on the surface of the brain or dura to radiate ultrasound energy through the brain and to the blood clot. In some embodiments, the ultrasound radiating member can be disk shaped that closely matches the size of the bore hole in the patient's skull. The disk shaped ultrasound radiating member can be a relatively large air-backed flat cylinder with external cooling. The large size enables the ultrasound radiating member to operate at a relatively low frequency. In some embodiments, a plurality of ultrasound radiating members can be used to form a focused array to increase the accuracy and safety of the ultrasound targeting. In some embodiments, the disk shaped ultrasound radiating member can have a port or hole to allow the passage of a drug deliver and/or drainage catheter through the ultrasound radiating member.

After the ultrasound catheter 400 is inserted into the brain and to the blood clot, a passage in the brain to the blood clot is created. Liquid can travel up this passage and along the exterior of the ultrasound catheter 400. In addition, the formation of the passage in the brain tissue can cause capillary bleeding. As lytic drug is delivered from the catheter 400 through the fluid delivery ports 414, some of the lytic can move proximally in the passage over the elongate tubular body 402 of the catheter 400 and inhibit the clotting of the bleeding capillaries, thereby furthering the bleeding into the brain. Accordingly, in some embodiments, as illustrated in FIGS. 16A-C, the ultrasound catheter 400 further comprises an occluder 430 located on the elongate tubular body 402 proximally of the fluid delivery ports 414. The occluder 430 can be a low pressure balloon wrapped around the elongate tubular body 402 as shown in FIG. 16A. The low pressure balloon is designed to be inflated at low pressures until the passage in the brain is occluded by the balloon, thereby reducing the flow of fluids, and lytic drug in particular, proximally of the occluder 430. The balloon is inflated at low pressure to reduce the force exerted against brain tissue, thereby reducing the damage to brain tissue. In some embodiments, the balloon can be elongate, toroidal or cuff-like.

In some embodiments, the occluder 430 can be a collar or cuff around elongate tubular body 402 as illustrated in FIG. 16B. The collar of cuff provides the same or similar functions as the elongate low pressure balloon described above by occluding the passage in the brain. The collar or cuff can be made of an elastic, resilient and deformable material that reversibly conforms to the shape of the passage while exerting low levels of force against the brain tissue. The force exerted by the collar or cuff against the brain tissue is sufficient to form an adequate seal while minimizing and/or reducing the damage to brain tissue.

In some embodiments, the occluder 430 can be a flap or series of flaps attached to the elongate tubular body 402 as shown in FIG. 16C. The flaps can be oriented either towards the proximal end or the distal end of the ultrasound catheter 400. The flaps have the same or similar function as the elongate low pressure balloon described above. The flaps can be designed to extend axially at a shallow angle. In some embodiments, the flap can be generally frustoconical in shape. In some embodiments, one end of the flap is attached to the elongate tubular body 402 while the free end is inwardly curved to provide an atraumatic surface. In some embodiments, both ends of the flaps are attached to the elongate tubular body 402 to form a collar or cuff-like structure. The flap or flaps can be flexible, elastic and resilient so that the flaps can press against the brain tissue and form a seal while minimizing and/or reducing the damage to brain tissue.

While the foregoing detailed description has set forth several exemplary embodiments of the apparatus and methods of the present invention, it should be understood that the above description is illustrative only and is not limiting of the disclosed invention. It will be appreciated that the specific dimensions and configurations disclosed can differ from those described above, and that the methods described can be used within any biological conduit within the body.

What is claimed is:

1. A method for treating a blood clot resulting from an intracranial hemorrhage in a brain of a patient, the method comprising:

advancing a tubular body through a patient's skull and into the blood clot in the brain, the tubular body including a central lumen and a fluid delivery lumen and including a distal portion configured for advancement into a patient's brain;

advancing an inner core comprising an ultrasound radiating element into the central lumen of the tubular body;

delivering a therapeutic compound through the fluid delivery lumen of the tubular body and to the blood clot positioned outside the tubular body;

transmitting ultrasound energy with the inner core to the blood clot; and evacuating clot material from the brain through the tubular body, wherein the tubular body further includes an evacuation lumen separate from the central lumen, and evacuating clot material occurs through the evacuation lumen.

2. The method of claim 1, further including monitoring intracranial pressure using a pressure sensor.

3. The method of claim 2, wherein the pressure sensor is disposed on the tubular member.

4. The method of claim 3, wherein the pressure sensor is exposed to fluid surrounding the tubular member, and can directly measure intracranial pressure.

5. The method of claim 3, wherein the pressure sensor is disposed in the fluid delivery lumen.

6. The method of claim 2, wherein the tubular body further includes an evacuation lumen, and the pressure sensor includes a first pressure sensor in the fluid delivery lumen, and a second pressure sensor in the fluid evacuation lumen.

7. The method of claim 6, further including measuring intracranial pressure by calculating the pressure drop across the first and second pressure sensors.

8. The method of claim 2, wherein the pressure sensor includes a first pressure sensor in the fluid delivery lumen, and a second pressure sensor in the central lumen.

9. The method of claim 2, wherein if the monitored intracranial pressure rises above a predetermined threshold, reducing the intracranial pressure below the threshold by increasing the evacuating, reducing the delivering, or both.

10. The method of claim 1, wherein evacuating of clot material occurs through the central lumen.

11. The method of claim 1, wherein advancing the tubular body through the patient's skull includes inserting a device configured to provide additional stiffness to the tubular body within the central lumen, and then removing the device from the central lumen after the tubular member is advanced into the patient's skull.

12. The method of claim 1, comprising transmitting ultrasound energy at a frequency between about 20 kHz and about 20 MHz.

13. The method of claim 1, further including maintaining an intracranial pressure below a threshold pressure while delivering the therapeutic compound.

14. The method of claim 1, wherein the therapeutic compound includes a thrombolytic compound.

15. The method of claim 14, wherein the therapeutic compound includes one or more of a neuroprotective agent, an anti-apoptotic agent, and a neurotoxin scavenging agent.

16. The method of claim 1, wherein the ultrasound catheter has multiple ultrasound elements configured for use in the brain.

17. The method of claim 1, wherein the light source is configured to emit a wavelength and amplitude of light selected for its ability to penetrate clot and brain tissue.

18. A method for treating a blood clot resulting from an intracranial hemorrhage in a brain of a patient, the method comprising:
- advancing a tubular body through a patient's skull and into the blood clot in the brain, the tubular body including a central lumen and a fluid delivery lumen and including a distal portion configured for advancement into a patient's brain;
- advancing an inner core comprising an ultrasound radiating element into the central lumen of the tubular body;
- delivering a therapeutic compound through the fluid delivery lumen of the tubular body and to the blood clot positioned outside the tubular body;
- transmitting ultrasound energy with the inner core to the blood clot;
- evacuating clot material from the brain through the tubular body;
- further including monitoring intracranial pressure using a pressure sensor; and
- wherein the tubular body further includes an evacuation lumen, and the pressure sensors is disposed in the fluid evacuation lumen.

19. A method for treating a blood clot resulting from an intracranial hemorrhage in a brain of a patient, the method comprising:
- advancing a tubular body through a patient's skull and into the blood clot in the brain, the tubular body including a central lumen and a fluid delivery lumen and including a distal portion configured for advancement into a patient's brain;
- advancing an inner core comprising an ultrasound radiating element into the central lumen of the tubular body;
- delivering a therapeutic compound through the fluid delivery lumen of the tubular body and to the blood clot positioned outside the tubular body;
- transmitting ultrasound energy with the inner core to the blood clot;
- evacuating clot material from the brain through the tubular body; and
- further including activating a light source located on the tubular body or inner core.

* * * * *